(12) United States Patent
Fischer et al.

(10) Patent No.: US 7,420,062 B2
(45) Date of Patent: Sep. 2, 2008

(54) HETARYL-SUBSTITUTED PYRAZOLIDINDIONE DERIVATIVES WITH PESTICIDAL CHARACTERISTICS

(75) Inventors: Reiner Fischer, Monheim (DE); Lutz Aβmann, Langenfeld (DE); Stefan Lehr, Liederbach (DE); Mark Wilhelm Drewes, Langenfeld (DE); Dieter Feucht, Eschborn (DE); Olga Malsam, Rösrath (DE); Guido Bojack, Wiesbaden (DE); Thomas Auler, Leichlingen (DE); Martin Jeffrey Hills, Idstein (DE); Heinz Kehne, Hofheim (DE); Christian Arnold, Langenfeld (DE)

(73) Assignee: Bayer CropScience, AG, Monheim (DE)

( * ) Notice: Subject to any disclaimer, the term of this patent is extended or adjusted under 35 U.S.C. 154(b) by 0 days.

(21) Appl. No.: 10/564,511

(22) PCT Filed: Jul. 12, 2004

(86) PCT No.: PCT/EP2004/007665

§ 371 (c)(1),
(2), (4) Date: Jul. 3, 2006

(87) PCT Pub. No.: WO2005/005428

PCT Pub. Date: Jan. 20, 2005

(65) Prior Publication Data

US 2007/0066488 A1   Mar. 22, 2007

(30) Foreign Application Priority Data

Jul. 14, 2003   (DE) ................. 103 31 675

(51) Int. Cl.
*C07D 231/54*   (2006.01)
(52) U.S. Cl. .................. 548/363.1
(58) Field of Classification Search ........ 548/363.1
See application file for complete search history.

(56) References Cited

U.S. PATENT DOCUMENTS

| | | | | |
|---|---|---|---|---|
| 2,759,944 | A * | 8/1956 | Logemann | 546/324 |
| 4,146,721 | A | 3/1979 | Rainer | |
| 5,332,720 | A * | 7/1994 | Kruger et al. | 504/281 |
| 6,008,230 | A * | 12/1999 | Oku et al. | 514/311 |
| 6,221,810 | B1 * | 4/2001 | Kruger et al. | 504/282 |
| 6,235,680 | B1 | 5/2001 | Ziemer et al. | |
| 6,251,827 | B1 | 6/2001 | Ziemer et al. | |

FOREIGN PATENT DOCUMENTS

| | | |
|---|---|---|
| DE | 1 945 703 | 7/1970 |
| DE | 1 946 370 | 4/1971 |
| DE | 2 218 097 | 11/1972 |
| DE | 2 350 547 | 4/1974 |
| DE | 196 21 522 A1 | 12/1997 |
| DE | 101 52 005 A1 | 4/2003 |
| EP | 0 086 750 A2 | 8/1983 |
| EP | 0 094 349 A2 | 11/1983 |
| EP | 0 174 562 A2 | 3/1986 |
| EP | 0 177 353 A2 | 4/1986 |
| EP | 0 191 736 A2 | 8/1986 |
| EP | 0 269 806 A1 | 6/1988 |
| EP | 0 333 131 A1 | 9/1989 |
| EP | 0 346 620 A1 | 12/1989 |
| EP | 0 368 592 A1 | 5/1990 |
| EP | 0 389 699 A1 | 10/1990 |
| EP | 0 492 366 A2 | 7/1992 |
| EP | 0 508 126 A1 | 10/1992 |
| EP | 0 528 156 A1 | 2/1993 |
| EP | 0 582 198 A2 | 2/1994 |
| EP | 0 613 618 A1 | 9/1994 |
| NL | 6614130 | 4/1967 |
| WO | WO 87/03807 A1 | 7/1987 |
| WO | WO 91/07874 A1 | 6/1991 |
| WO | WO 91/08202 A1 | 6/1991 |
| WO | WO 92/16510 A1 | 10/1992 |
| WO | WO 94/29268 A1 | 12/1994 |
| WO | WO 95/07897 A1 | 3/1995 |
| WO | WO 95/18125 A1 | 7/1995 |
| WO | WO 96/11574 A1 | 4/1996 |
| WO | WO 96/21652 A1 | 7/1996 |
| WO | WO 96/35664 A1 | 11/1996 |
| WO | WO 96/37494 A1 | 11/1996 |

(Continued)

OTHER PUBLICATIONS

Alberola, A., et al., "Reaccion de β-Aminoenonas con Derivados de Hidrazina. Sintesis Regioselectiva de Pirazoles," *An. Quim., Ser. C.* 83:55-61, La Sociedad (1987).

(Continued)

*Primary Examiner*—Rebecca L Anderson
*Assistant Examiner*—Robert Havlin
(74) *Attorney, Agent, or Firm*—Sterne, Kessler, Goldstein & Fox PLLC

(57) ABSTRACT

The present invention relates to hetaryl-substituted pyrazolidine derivatives of the formula (I)

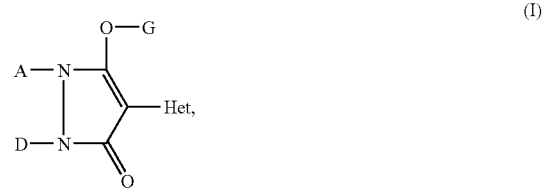

in which
Het, A, D and G are as defined above,
to a plurality of processes for their preparation and to their use as pesticides and/or herbicides.

Moreover, the invention relates to selective herbicidal compositions comprising both the hetaryl-substituted pyrazolidinedione derivatives and a crop plant compatibility-improving compound.

12 Claims, No Drawings

FOREIGN PATENT DOCUMENTS

| WO | WO 97/01535 A1 | 1/1997 |
|---|---|---|
| WO | WO 97/02243 A1 | 1/1997 |
| WO | WO 97/36868 A1 | 10/1997 |
| WO | WO 98/05638 A2 | 2/1998 |
| WO | WO 98/25923 A1 | 6/1998 |
| WO | WO 99/47525 A1 | 9/1999 |
| WO | WO 99/66795 A1 | 12/1999 |
| WO | WO 01/17351 A1 | 3/2001 |
| WO | WO 01/17352 A1 | 3/2001 |
| WO | WO 01/17353 A1 | 3/2001 |
| WO | WO 01/17972 A2 | 3/2001 |
| WO | WO 01/17973 A2 | 3/2001 |
| WO | WO 03/028466 A2 | 4/2003 |
| WO | WO 2005/007897 A1 | 1/2005 |
| WO | WO 2005/092897 A2 | 10/2005 |

OTHER PUBLICATIONS

STNEasy Database, Accession No. 1988:150363, English language abstract for Alberola, A., "Reaction of beta-aminoenones with hydrazine derivatives. Regioselective synthesis of pyrazoles," *An. Quim., Ser. C.* 83:55-61, (1987).

Asakani, R., "Zur Reaktion von Cyclohexadien-(1.3) mit Azodicarbonsäure-diäthylester," *Chem. Ber.* 98:2551-2555, Verlag Chemie (1965).

STNEasy Database, Accession No. 1965:463036, English language abstract for Askani, R., "Reaction of 1,3-cyclohexadiene with azodicarboxylic acid diethyl ester," *Chem. Berichte.* 98:2551-2555, Verlag Chemie (1965).

Baciocchi, E., Dimethyl Arylmalonates from Cerium (IV) Ammonium Nitrate Promoted Reactions of Dimethyl Malonate with Aromatic Compounds in Methanol, *Tetrahedron Lett.* 27:2763-2766, Elsevier (1986).

Collins, J.L., et al., "N-(2-Benzolyphenyl)-L-tyrosine PPAR$_\gamma$ Agonists. 2. Sructure—Activity Relationship and Optimization of the Phenyl Alkyl Ether Moiety," *J. Med. Chem.* 41:5037-5054, American Chemical Society (1998).

Dannenberg, V.H. and Dannenberg-von Dresler, D., "Verusche zur Synthese des Steranthrens III," *Justus Liebigs Ann. Chem.* 585:1-15, Verlag Chemie (1954).

STNEasy Database, Accession No. 1955:56638, English language abstract for Dannenberg, H. and Dannenberg-Von Dresler, D., "Synthesis of steranthrenes. III. 3,4-Aceperinaphthane and 6,7-aceperinaphthane," *Ann. Chem.* 585:1-15, Verla Chemie (1954).

Diels, V.O., et al., "Über das aus Cyclopentadien und Azoester entestehende Endomethylen-piperidazin und seine Überführung in 1,3-Diamino-cyclopentan," *Justus Liebigs Ann. Chem.* 443:242-262, Verlag Chemie (1925).

STNEasy Database, Accession No. 1925:19216, English language abstract for Diels, O., et al., "The endo-methylenepiperidazine resulting from cyclopendadiene and azo ester and its transformation diaminocyclopentane," *Ann. Chem.* 443:242-262, Verlag Chemie (1925).

Ebeid, M.Y., et al., "Synthesis and Biological Activity of Some New 5-Nitrothiazole Derivatives," *Egypt. J. Pharm. Sci.* 33:99-110, National Information and Documentation Centre Ohio (1992).

Hulin, B., et al., "Novel Thiazolidine-2,4-diones as Potent Euglycemic Agents," *J. Med. Chem.* 35:1853-1864. American Chemical Society (1992).

Ikeda, Y., et al., "Syntheses and Biological Activities of Some Dithiolanylidenemalonate Derivatives and Related Compounds," *J. Fac. Agr. Kyushu Univ.* 37:81-92, Faculty of Agric Publications—Kyushu University (1992).

Kandeel, M. M., "Synthesis of 4-substituted 3-methyl-1-phenyl-2-pyrazoline-5-thiones by heterocylces," *Bull. Soc. Chim. Fr., Issue* 6:1005-1008, Societe Francaise De Chimie (1988).

Kulikova, L.K. and Cherkesova, L.V., "Antimicrobial Activity of Compounds in the Series of 5(3)-(2-thienyl) Pyrazole," *Khim.-Farm. Zh.* 8:18-21, Folium Publishing Company (1974).

STNEasy Database, Accession No. 1974:437505, English language abstract for Kulikova, L.K. and Cherkesova, L.V., "Antimicrobial Activity of Compounds in the Series of 5(3)-(2-thienyl) Pyrazole," *Khim.-Farm. Zh.* 8:18-21, Folium Publishing Company (1974).

Malamas, M.S., et al., "Azole Phenoxy Hydroxyureas as Selective and Orally Active Inhibitors of 5-Lipoxygenase," *J. Med. Chem.* 39:237-245, American Chemical Society (1996).

Meguro, K., "Studies on Antidiabetic Agents. VII. Synthesis and Hypoglycemic Activity of 4-Oxazoleacetic Acid Derivatives," *Chem. Pharm. Bull.* 34:2840-2851, Pharmaceutical Society of Japan (1986).

Nakanishi, S. and Butler, K., "Synthesis of Chlorocarbonyl Ketenes," *Org. Prep. Proced. Int.* 7:155-158, Organic Preparations and Procedures, Inc. (1975).

Nam, N.L., et al., "Simple Method for the Synthesis of 3,5-Dimethylpyrazolyl-1-Acetic Acid," *Chemistry of Heterocyclic Compounds 34*:382, Plenum Publishing Corporation (1998).

Rooney, C.S., et al., "Inhibitors of Glycolic Oxidase. 4-Substited 3-Hydroxy-1H-pyrrole-2,5-dione Derivatives," *J. Med. Chem.* 26:700-714, American Chemical Society (1983).

Scheiblich, S., et al., "Bis-pyrimidylpyrazolinones—a new class of acetohydroxy-acid synthase (AHAS) inhibitor," *Pestic. Sci.* 55:633-675, Wiley And Sons (1999).

Seki, M., et al., "Synthesis of 5-Alkyl-4-oxazoleacetic Acid Derivatives with Hypolipidemic Activities," *Chem. Pharm Bull.* 36:4435-4440, Pharmaceutical Society of Japan (1988).

Youssef, M.S.K., "Synthesis of 1-(2,4-Dinitrophenyl)-3-methyl4-substituted Heterocycles-2-pyrazolin-5-one," *Z. Naturforcsch. B 39*:86-89, Verlag Der Zeitschrift Fur Naturforschung (1983).

International Search Report for International Application No. PCT/EP2004/007665, European Patent Office, Netherlands, mailed on Dec. 28, 2004.

Dialog File 351, Accession No. 124723, Derwent WPI English language abstract for NL 6,614,130 (listed on accompanying PTO/SB/08A as document FP1).

Dialog File 351, Accession No. 288927, Derwent WPI English language abstract for DE 1 945 703 A1 (listed on accompanying PTO/SB/08A as document FP2).

Dialog File 351, Accession No. 369741, Derwent WPI English language abstract for DE 1 946 370 (listed on accompanying PTO/SB/08A as document FP3).

Dialog File 351, Accession No. 502720, Derwent WPI English language abstract for DE 2 218 097 A1 (listed on accompanying PTO/SB/08A as document FP4).

Dialog File 351, Accession No. 629712, Derwent WPI English language abstract for DE 2 350 547 A1 (listed on accompanying PTO/SB/08A as document FP6).

Dialog File 351, Accession No. 2714950, Derwent WPI English language abstract for EP 0 086 750 A2 (listed on accompanying PTO/SB/08A as document FP7).

Dialog File 351, Accession No. 2777922, Derwent WPI English language abstract for EP 0 094 349 A2 (listed on accompanying PTO/SB/08A as document FP8).

Dialog File 351, Accession No. 3892231, Derwent WPI English language abstract for EP 0 174 562 A2 (listed on accompanying PTO/SB/08A as document FP9).

Dialog File 351, Accession No. 3770049, Derwent WPI English language abstract for EP 0 191 736 A2 (listed on accompanying PTO/SB/08A as document FP10).

Dialog File 351, Accession No. 4372286, Derwent WPI English language abstract for EP 0 269 806 A1 (listed on accompanying PTO/SB/08A as document FP13).

Dialog File 351, Accession No. 4889149, Derwent WPI English language abstract for EP 0 333 131 A1 (listed on accompanying PTO/SB/08A as document FP14).

Dialog File 351, Accession No. 4963457, Derwent WPI English language abstract for EP 0 346 620 A1 (listed on accompanying PTO/SB/08A as document FP15).

Dialog File 351, Accession No. 5984812, Derwent WPI English language abstract for EP 0 492 366 A2 (listed on accompanying PTO/SB/08A as document FP20).

Dialog File 351, Accession No. 6602040, Derwent WPI English language abstract for EP 0 528 156 (listed on accompanying PTO/SB/08A as document FP23).

Dialog File 351, Accession No. 6665683, Derwent WPI English language abstract for EP 0 582 198 A2 (listed on accompanying PTO/SB/08A as document FP24).

Dialog File 351, Accession No. 8440872, Derwent WPI English language abstract for WO 96/35664(listed on accompanying PTO/SB/08A as document FP31).

Dialog File 351, Accession No. 9053979, Derwent WPI English language abstract for DE 196 21 522 A1 (listed on accompanying PTO/SB/08A as document FP36).

Dialog File 351, Accession No. 9060886, Derwent WPI English language abstract for WO 98/05638 (listed on accompanying PTO/SB/08A as document FP37).

Dialog File 351, Accession No. 13822137, Derwent WPI English language abstract for DE 101 52 005 (listed on accompanying PTO/SB/08A as document FP47).

* cited by examiner

HETARYL-SUBSTITUTED PYRAZOLIDINDIONE DERIVATIVES WITH PESTICIDAL CHARACTERISTICS

This application is a 35 U.S.C. §371 U.S. National Phase filing of International Application No. PCT/EP04/07665, filed Jul. 12, 2004, which claims the benefit of German Patent Application No. 103 31 675.2, filed Jul. 14, 2003.

The present invention relates to novel hetaryl-substituted pyrazolidinedione derivatives, to a plurality of processes for their preparation and to their use as pesticides and/or herbicides. Moreover, the invention relates to novel selective herbicidal active compound combinations comprising both the hetaryl-substituted pyrazolidinedione derivatives and at least one crop plant compatibility-improving compound, which combinations can be used with particularly good results for the selective control of weeds in various crops of useful plants.

It is known that certain substituted 4-arylpyrazolidine-3,4-diones have acaricidal, insecticidal and herbicidal properties (cf., for example, WO 92/16510, EP-A 508 126, WO 96/11574, WO 96/21652, WO 99/47525; WO 01/17351, WO 01/17352, WO 01/17353, WO01/17972, WO 01/17973, WO 03/028466).

This invention now provides novel compounds of the formula (I)

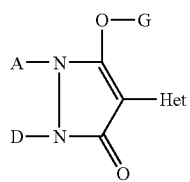

in which

Het represents in each case optionally substituted thiazolyl (A), oxazolyl (B) or pyrazolyl (C), A represents hydrogen, in each case optionally halogen-substituted alkyl, alkenyl or alkoxyalkyl, D represents hydrogen or an optionally substituted radical from the group consisting of alkyl, alkenyl, alkynyl, alkoxyalkyl, polyalkoxyalkyl, alkylthioalkyl, saturated or unsaturated cycloalkyl in which optionally one or more ring members are replaced by heteroatoms, arylalkyl, aryl, hetarylalkyl or hetaryl, or A and D together with the atoms to which they are attached represent a saturated or unsaturated cycle which is unsubstituted or substituted in the A, D moiety and optionally contains at least one heteroatom G represents hydrogen (a) or represents one of the groups

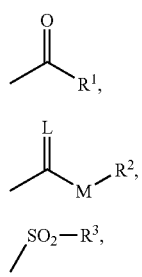

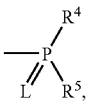

E or

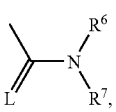

in which

E represents a metal ion equivalent or an ammonium ion,

L represents oxygen or sulfur,

M represents oxygen or sulfur, $R^1$ represents in each case optionally cyano- or halogen-substituted alkyl, alkenyl, alkoxyalkyl, alkylthioalkyl, polyalkoxyalkyl or optionally halogen-, alkyl- or alkoxy-substituted cycloalkyl which may be interrupted by at least one heteroatom, represents in each case optionally substituted phenylalkyl, hetaryl, phenoxyalkyl or hetaryloxyalkyl, $R^2$ represents in each case optionally halogen-substituted alkyl, alkenyl, alkoxyalkyl, polyalkoxyalkyl or represents in each case optionally substituted cycloalkyl, phenyl or benzyl, $R^3$ represents alkyl, haloalkyl or represents in each case optionally substituted phenyl or benzyl, $R^4$ and $R^5$ independently of one another represent in each case optionally halogen-substituted alkyl, alkoxy, alkylamino, dialkylamino, alkylthio, alkenylthio, cycloalkylthio and represent in each case optionally substituted phenyl, benzyl, phenoxy or phenylthio, $R^6$ and $R^7$ independently of one another represent hydrogen, in each case optionally halogen-substituted alkyl, cycloalkyl, alkenyl, alkoxy, alkoxyalkyl, represent optionally substituted phenyl, represent optionally substituted benzyl, or together with the nitrogen atom to which they are attached represent a cycle which is optionally interrupted by oxygen or sulfur.

Depending entirely on the nature of the substituents, the compounds of the formula (I) can be present as regioisomers, as geometrical and/or optical isomers or as isomer mixtures of varying composition which, if appropriate, can be separated in a customary manner. The present invention provides both the pure isomers and the isomer mixtures, their preparation and use and compositions comprising them. However, hereinbelow, for the sake of simplicity, only compounds of the formula (I) are referred to, although what is meant are both the pure compounds and if appropriate, also mixtures having varying proportions of isomeric compounds.

Taking into consideration the meanings (A) to (C) of the group Het the following general structures (I-A) to (I-C) result:

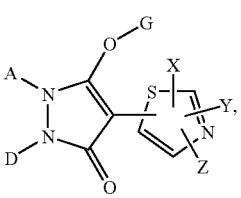

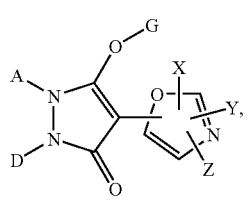

(I-B)

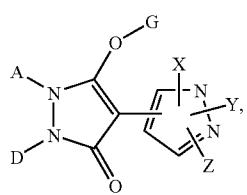

(I-C)

in which
A, D and G are as defined above and
X represents alkyl, halogen, haloalkyl or represents optionally substituted phenyl,
Y represents hydrogen, alkyl or halogen,
Z represents alkyl, hydroxyl, alkoxy, haloalkoxy, in each case optionally substituted phenyl-alkyloxy, heterarylalkyloxy or cycloalkyl.

Taking into account the general structures (I-A) to (I-C) and taking into consideration the possible attachment positions on the pyrazolyl radical, the following principle structures (I-1) to (I-4) result:

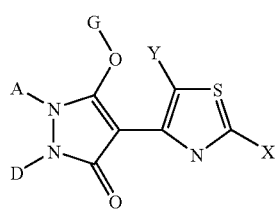

(I-1)

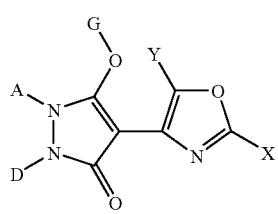

(I-2)

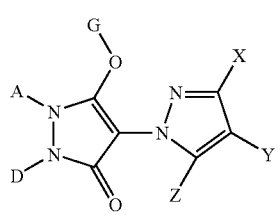

(I-3)

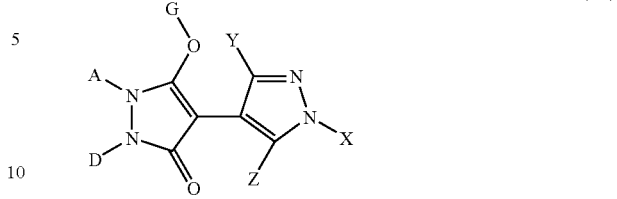

(I-4)

in which
A, D, G, X, Y and Z are as defined above.

Taking into account the different meanings (a), (b), (c), (d), (e), (f) and (g) of group G, the following principle structures (I-1-a) to (I-1-g) result if Het represents the group (A),

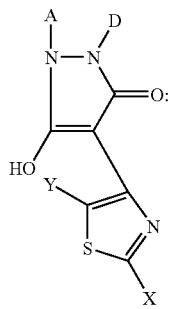

(I-1-a)

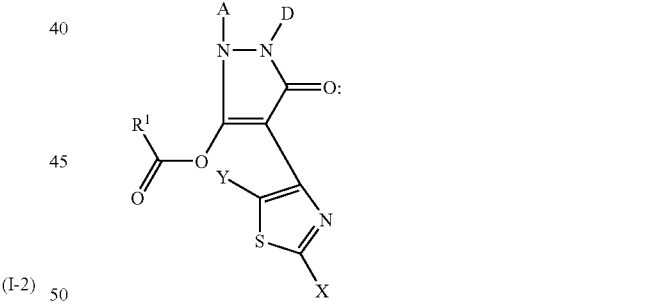

(I-1-b)

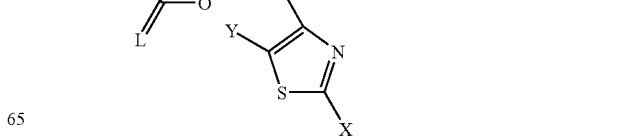

(I-1-c)

-continued
(I-1-d)
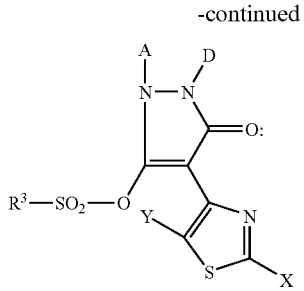
(I-1-e)
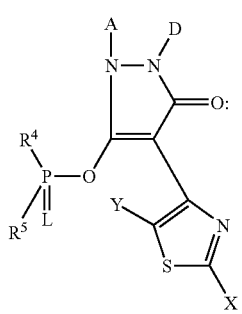
(I-1-f)
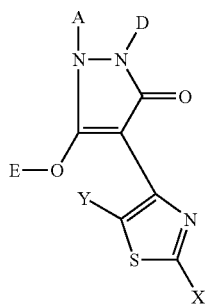
(I-1-g)
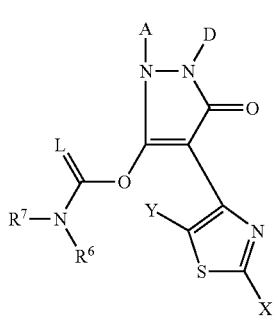
in which
A, D, E, L, M, X, Y, $R^1$, $R^2$, $R^3$, $R^4$, $R^5$, $R^6$ and $R^7$ are as defined above.
Taking into account the different meanings (a), (b), (c), (d), (e), (f) and (g) of the group G, the following principle structures (I-2-a) to (I-2-g) result if Het represents the group (B)
(I-2-a):
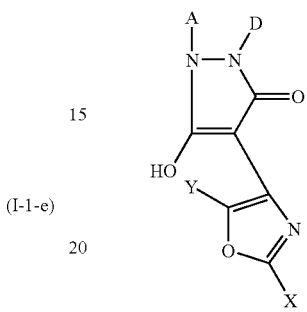
(I-2-b):
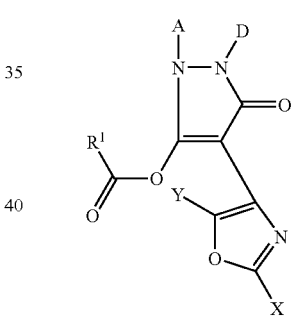
(I-2-c):
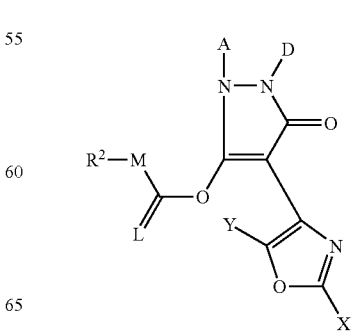

-continued
(I-2-d):
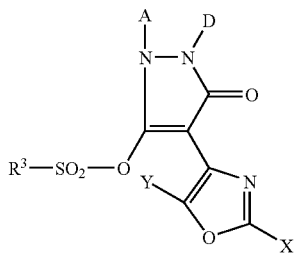
(I-2-e):
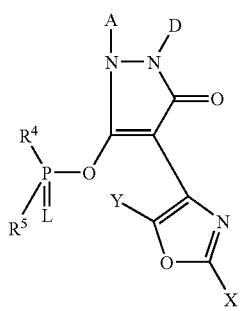
(I-2-f):
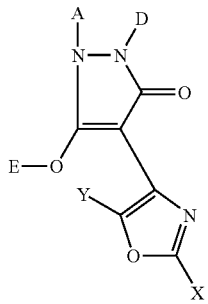
(I-2-g):
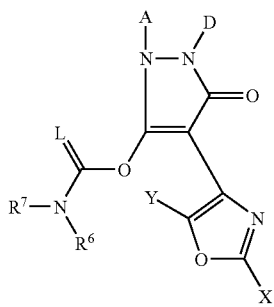
in which
A, D, E, L, M, X, Y, $R^1$, $R^2$, $R^3$, $R^4$, $R^5$, $R^6$ and $R^7$ are as defined above.
Taking into account the different meanings (a), (b), (c), (d), (e), (f) and (g) of the group G, the following principle structures (I-3-a) to (I-3-g) result if Het represents the group (C)
(I-3-a):
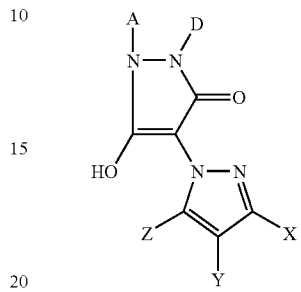
(I-3-b):
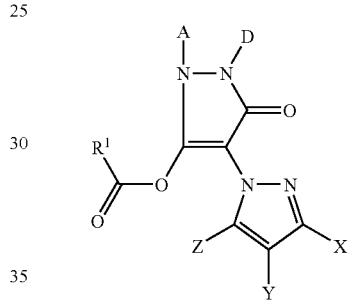
(I-3-c):
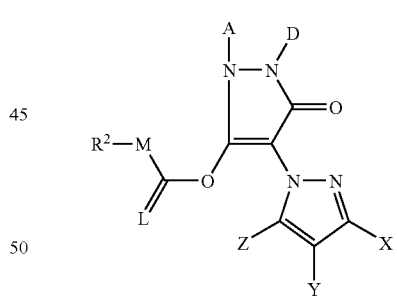
(I-3-d):
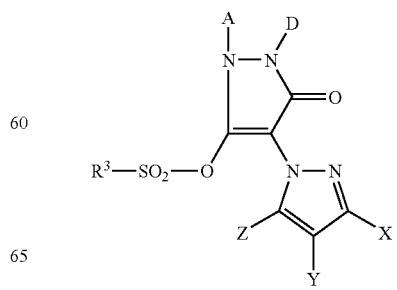

-continued
(I-3-e):
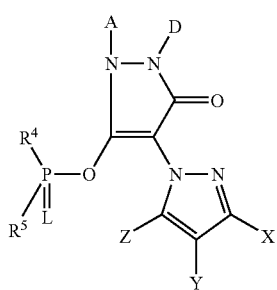
(I-3-f):
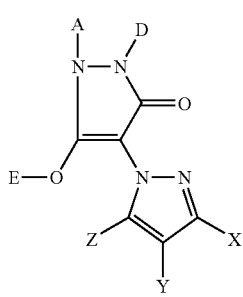
(I-3-g):
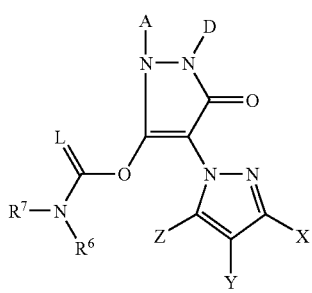
in which
A, D, E, L, M, X, Y, Z, R¹, R², R³, R⁴, R⁵, R⁶ and R⁷ are as defined above.
Taking into account the different meanings (a), (b), (c), (d), (e), (f) and (g) of the group G, the following principle structures (I-4-a) to (I-4-g) result if Het represents the group (C)
(I-4-a):
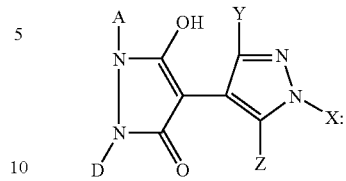
(I-4-b):
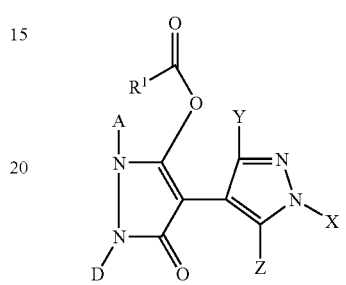
(I-4-c):
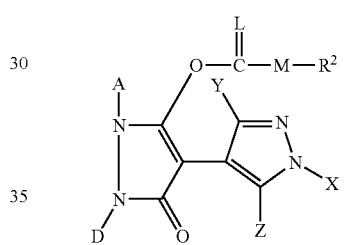
(I-4-d):
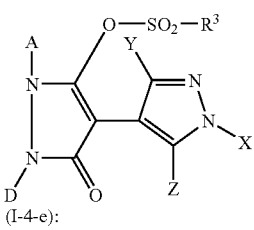
(I-4-e):
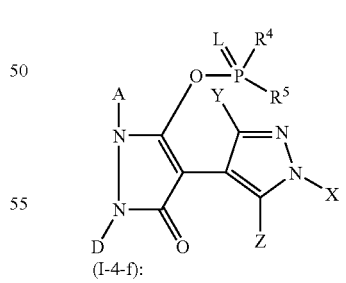
(I-4-f):
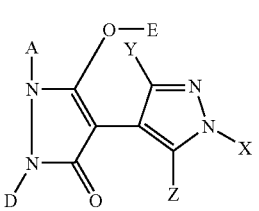

-continued (I-4-g):

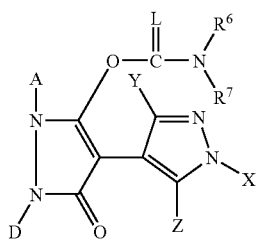

in which
A, D, E, L, M, X, Y, Z, $R^1$, $R^2$, $R^3$, $R^4$, $R^5$, $R^6$ and $R^7$ are as defined above.

Furthermore, it has been found that the novel compounds of the formula (I) are obtained by one of the processes described below:

(A) substituted 3-hetarylpyrrolidine-2,4-diones or enols thereof of the formulae (I-1-a) to (I-4-a)

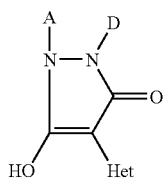 (I-1-a) to (I-4-a)

in which
A, D and Het are as defined above
are obtained when
compounds of the formula (II)

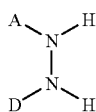 (II)

in which
A and D are as defined above
α) are reacted with compounds of the formula (III)

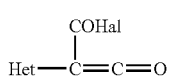 (III)

in which
Het is as defined above,
if appropriate in the presence of a diluent and if appropriate in the presence of an acid acceptor, or β) are reacted with compounds of the formula (IV)

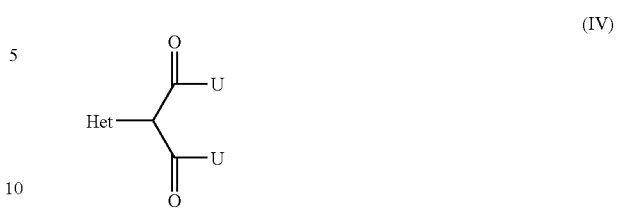 (IV)

in which
Het is as defined above
and U represents O—$R^8$, where $R^8$=$C_1$-$C_8$-alkyl,
if appropriate in the presence of a diluent and if appropriate in the presence of a base, or γ) are reacted with compounds of the formula (V)

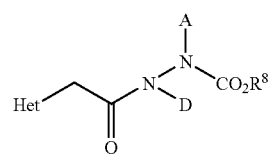 (V)

in which
A, D, Het and $R^8$ are as defined above,
if appropriate in the presence of a diluent and if appropriate in the presence of a base.

Moreover, it has been found
(B) that the compounds of the formulae (I-1-b) to (I-4-b) shown above in which A, D, $R^1$ and Het are as defined above are obtained when compounds of the formulae (I-1-a) to (I-4-a) shown above in which A, D and Het are as defined above are in each case reacted
(α) with acid halides of the formula (VI)

 (VI)

in which
$R^1$ is as defined above and
Hal represents halogen (in particular chlorine or bromine) or
(β) with carboxylic anhydrides of the formula (VII)

$R^1$—CO—O—CO—$R^1$ (VII)

in which
$R^1$ is as defined above,
if appropriate in the presence of a diluent and if appropriate in the presence of an acid binder;

(C) that the compounds of the formulae (I-1-c) to (I-4-c) shown above in which A, D, $R^2$, M and Het are as defined above and L represents oxygen are obtained when compounds of the formulae (I-1-a) to (I-4-a) shown above in which A, D and Het are as defined above are in each case reacted with chloroformic esters or chloroformic thioesters of the formula (VIII)

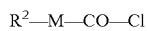
(VIII)

in which
R² and M are as defined above,
if appropriate in the presence of a diluent and if appropriate in the presence of an acid binder;

(D) that compounds of the formulae (I-1-c) to (I-4-c) shown above in which A, D, R², M and Het are as defined above and L represents sulfur are obtained when compounds of the formulae (I-1-a) to (I-4-a) shown above in which A, D and Het are as defined above are in each case
reacted with chloromonothioformic esters or chlorodithioformic esters of the formula (XI)

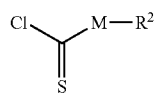
(IX)

in which
M and R² are as defined above,
if appropriate in the presence of a diluent and if appropriate in the presence of an acid binder,
and (E) that compounds of the formulae (I-1-d) to (I-4-d) shown above in which A, D, R³ and Het are as defined above are obtained when compounds of the formulae (I-1-a) to (I-4-a) shown above in which A, D and Het are as defined above are in each case
reacted with sulfonyl chlorides of the formula (X)

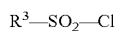
(X)

in which
R³ is as defined above,
if appropriate in the presence of a diluent and if appropriate in the presence of an acid binder, (F) that compounds of the formulae (I-1-e) to (I-4-e) shown above in which A, D, L, R⁴, R⁵ and Het are as defined above are obtained when compounds of the formulae (I-1-a) to (I-4-a) shown above in which A, D and Het are as defined above are in each case
reacted with phosphorus compounds of the formula (XI)

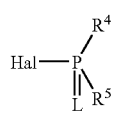
(XI)

in which
L, R⁴ and R⁵ are as defined above and
Hal represents halogen (in particular chlorine or bromine),
if appropriate in the presence of a diluent and if appropriate in the presence of an acid binder, (G) that compounds of the formulae (I-1-f) to (I-4-f) shown above in which A, D. E and Het are as defined above are obtained when compounds of the formulae (I-1-a) to (I-4-a) in which A, D and Het are as defined above are in each case
reacted with metal compounds or amines of the formulae (XII) and (XIII), respectively,

(XII)

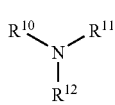
(XIII)

in which
Me represents a mono- or divalent metal (preferably an alkali metal or alkaline earth metal, such as lithium, sodium, potassium, magnesium or calcium),
t represents the number 1 or 2 and
R¹⁰, R¹¹, R¹² independently of one another represents hydrogen or alkyl (preferably C₁-C₈-alkyl),
if appropriate in the presence of a diluent, (H) that compounds of the formulae (I-1-g) to (I-4-g) shown above in which A, D, L, R⁶, R⁷ and Het are as defined above are obtained when compounds of the formulae (I-1-a) to (I-4-a) shown above in which A, D and Het are as defined above are in each case (α) reacted with isocyanates or isothiocyanates of the formula (XIV)

(XIV)

in which
R⁶ and L are as defined above,
if appropriate in the presence of a diluent and if appropriate in the presence of a catalyst, or (β) are reacted with carbamoyl chlorides or thiocarbamoyl chlorides of the formula (XV)

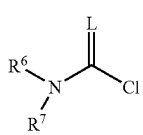
(XV)

in which
L, R⁶ and R⁷ are as defined above,
if appropriate in the presence of a diluent and if appropriate in the presence of an acid binder.

Furthermore, it has been found that the novel compounds of the formula (I) are highly active as pesticides, preferably as insecticides and/or acaricides and/or herbicides.

Surprisingly, it has now also been found that certain hetaryl-substituted pyrazolidinedione derivatives, when used jointly with the compounds which improve crop plant tolerance (safeners/antidotes) described hereinbelow, are extremely effective in preventing damage of the crop plants and can be used especially advantageously as combination products with a broad range of activity for the selective control of unwanted plants in crops of useful plants, such as, for example, in cereals, but also in corn, soybeans and rice.

The invention also provides selective-herbicidal compositions comprising an effective amount of an active compound combination comprising, as components, (a') at least one hetaryl-substituted pyrazolidinedione derivative of the formula (I) in which A, D, G and Het are as defined above
and
(b') at least one crop plant compatibility-improving compound from the following group of compounds:
4-dichloroacetyl-1-oxa-4-azaspiro[4.5]decane (AD-67, MON-4660), 1-dichloro-acetylhexahydro-3,3,8a-trimethylpyrrolo[1,2-a]pyrimidin-6(2H)-one (dicyclonon, BAS-145138), 4-dichloroacetyl-3,4-dihydro-3-methyl-2H1,4-benzoxazine(benoxacor), 1-methylhexyl 5-chloroquinoline-8-oxyacetate(cloquintocet-mexyl—cf. also related compounds in EP-A-86750, EP-A-94349, EP-A-191736. EP-A-492366), 3-(2-chlorobenzyl)-1-(1-methyl-1-phenylethyl)urea (cumyluron), α-(cyanomethoximino)phenylacetonitrile (cyometrinil), 2,4-dichlorophenoxyacetic acid (2,4-D), 4-(2,4-dichlorophenoxy)butyric acid (2,4-DB), 1-(1-methyl-1-phenylethyl)-3-(4-methylphenyl)urea (daimuron, dymron), 3,6-dichloro-2-methoxybenzoic acid (dicamba), S-1-methyl 1-phenylethyl piperidine-1-thiocarboxylate (dimepiperate) 2.2-dichloro-N-(2-oxo-2-(2-propenylaminoi)ethyl)-N-(2-propenyl)acetamide (DKA-24), 2,2-dichloro-N,N-di-2-propenylacetamide (dichlormid), 4,6-dichloro-2-phenylpyrimidine (fenclorim), ethyl 1-(2,4-dichlorophenyl)-5-trichloromethyl-1H-1,2,4-triazole-3-carboxylate (fenchlorazole-ethyl—cf. also related compounds in EP-A-174562 and EP-A-346620), phenylmethyl 2-chloro-4-trifluoromethylthiazole-5-carboxylate (flurazole), 4-chloro-N-(1.3-dioxolan-2-ylmethoxy)-α-trifluoroacetophenone oxime (fluxofenim), 3-dichloroacetyl-5-(2-furanyl)-2,2-dimethyloxazolidine (furilazole, MON-13900), ethyl 4,5-dihydro-5,5-diphenyl-3-isoxazolecarboxylate(isoxadifen-ethyl—cf. also related compounds in WO-A-95/07897), 1-(ethoxycarbonyl)ethyl 3,6-dichloro-2-methoxybenzoate (lactidichlor), (4-chloro-o-tolyloxy)acetic acid (MCPA), 2-(4-chloro-o-tolyloxy) propionic acid (mecoprop), diethyl 1-(2,4-dichlorophenyl)-4,5-dihydro-5-methyl-1H-pyrazole-3,5-dicarboxylate (mefenpyr-diethyl—cf. also related compounds in WO-A-91/07874), 2-dichloromethyl-2-methyl-1,3-dioxolane (MG-191), 2-propenyl 1-oxa-4-azaspiro[4.5]decane-4-carbodithioate (MG-838), 1,8-naphthalic anhydride, α-(1,3-dioxolan-2-ylmethoximino) phenylacetonitrile (oxabetrinil), 2,2-dichloro-N-(1,3-dioxolan-2-ylmethyl)-N-(2-propenyl)acetamide (PPG-1292), 3-dichloroacetyl-2,2-dimethyloxazolidine (R-28725), 3-dichloroacetyl-2,2,5-trimethyloxazolidine (R-29148), 4-(4-chloro-o-tolyl)butyric acid, 4-(4-chlorophenoxy)butyric acid, diphenylmethoxyacetic acid, methyl diphenylmethoxyacetate, ethyl diphenylmethoxyacetate, methyl 1-(2-chlorophenyl)-5-phenyl-1H-pyrazole-3-carboxylate, ethyl 1-(2,4-dichlorophenyl)-5-methyl-1H-pyrazole-3-carboxylate, ethyl 1-(2,4-dichlorophenyl)-5-isopropyl-1H-pyrazole-3-carboxylate, ethyl 1-(2,4-dichlorophenyl)-5-(1,1-dimethylethyl)-1H-pyrazole-3-carboxylate, ethyl 1-(2,4-dichlorophenyl)-5-phenyl-1H-pyrazole-3-carboxylate (cf. also related compounds in EP-A-269806 and EP-A-333131), ethyl 5-(2,4-dichlorobenzyl)-2-isoxazoline-3-carboxylate, ethyl 5-phenyl-2-isoxazoline-3-carboxylate, ethyl 5-(4-fluorophenyl)-5-phenyl-2-isoxazoline-3-carboxylate (cf. also related compounds in WO-A-91/08202), 1,3-dimethylbut-1-yl 5-chloroquinoline-8-oxyacetate, 4-allyloxybutyl 5-chloroquinoline-8-oxyacetate, 1-allyloxyprop-2-yl 5-chloroquinoline-8-oxyacetate, methyl 5-chloroquinoxaline-8-oxyacetate, ethyl 5-chloroquinoline-8-oxyacetate, allyl 5-chloroquinoxaline-8-oxyacetate, 2-oxoprop-1-yl 5-chloroquinoline-8-oxyacetate, diethyl 5-chloroquinoline-8-oxymalonate, diallyl 5-chloroquinoxaline-8-oxymalonate, diethyl 5-chloroquinoline-8-oxymalonate (cf. also related compounds in EP-A-582198), 4-carboxychroman-4-ylacetic acid (AC-304415, cf. EP-A-613618), 4-chlorophenoxyacetic acid, 3,3'-dimethyl-4-methoxybenzophenone, 1-bromo-4-chloromethylsulfonylbenzene, 1-[4-(N-2-methoxybenzoylsulfamoyl)phenyl]-3-methylurea (also known as N-(2-methoxybenzoyl)-4-[(methylaminocarbonyl)-amino]benzenesulfonamide), 1-[4-(N-2-methoxybenzoylsulfamoyl)phenyl]-3,3-dimethylurea, 1-[4-(N-4,5-dimethylbenzoylsulfamoyl)phenyl]-3-methylurea, 1-[4-(N-naphthylsulfamoyl)phenyl]-3,3-dimethylurea, N-(2-methoxy-5-methylbenzoyl)-4-(cyclopropylaminocarbonyl)benzenesulfonamide, and/or one of the following compounds, defined by general formulae, of the general formula (IIa)

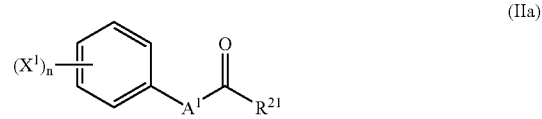

or of the general formula (IIb)

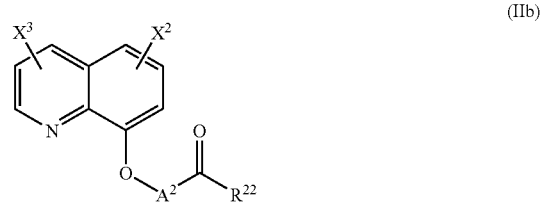

or of the formula (IIc)

where
n represents a number between 0 and 5,
A¹ represents one of the divalent heterocyclic groupings shown below,

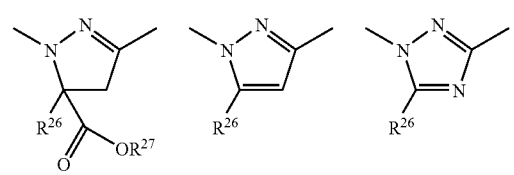

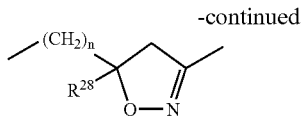

-continued n represents a number between 0 and 5, $A^2$ represents optionally $C_1$-$C_4$-alkyl- and/or $C_1$-$C_4$-alkoxy-carbonyl-substituted alkanediyl having 1 or 2 carbon atoms, $R^{21}$ represents hydroxyl, mercapto amino, $C_1$-$C_6$-alkoxy, $C_1$-$C_6$-alkylthio, $C_1$-$C_6$-alkylamino or di-($C_1$-$C_4$-alkyl) amino, $R^{22}$ represents hydroxyl, mercapto, amino, $C_1$-$C_6$-alkoxy, $C_1$-$C_6$-alkylthio, $C_1$-$C_6$-alkylamino or di-($C_1$-$C_4$-alkyl) amino, $R^{23}$ represents in each case optionally fluorine-, chlorine- and/or bromine-substituted $C_1$-$C_4$-alkyl, $R^{24}$ represents hydrogen, in each case optionally fluorine-, chlorine- and/or bromine-4 substituted $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, or optionally fluorine-, chlorine- and/or bromine- or $C_1$-$C_4$-alkyl-substituted phenyl, $R^{25}$ represents hydrogen, in each case optionally fluorine-, chlorine- and/or bromine-substituted $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, or optionally fluorine-, chlorine- and/or bromine- or $C_1$-$C_4$-alkyl-substituted phenyl, or together with $R^{24}$ represents $C_3$-$C_6$-alkanediyl or $C_2$-$C_5$-oxaalkanediyl, each of which is optionally substituted by $C_1$-$C_4$-alkyl, phenyl, furyl, a fused benzene ring or by two substituents which, together with the C atom to which they are attached, form a 5- or 6-membered carbocycle, $R^{26}$ represents hydrogen, cyano, halogen, or represents in each case optionally fluorine-, chlorine- and/or bromine-substituted $C_1$-$C_4$-alkyl, $C_3$-$C_6$-cycloalkyl or phenyl.

$R^{27}$ represents hydrogen or in each case optionally hydroxyl-, cyano-, halogen- or $C_1$-$C_4$-alkoxy-substituted $C_1$-$C_6$-alkyl, $C_3$-$C_6$-cycloalkyl or tri($C_1$-$C_4$-alkyl)silyl, $R^{28}$ represents hydrogen, cyano, halogen, or represents in each case optionally fluorine-, chlorine- and/or bromine-substituted $C_1$-$C_4$-alkyl, $C_3$-$C_6$-cycloalkyl or phenyl, $X^1$ represents nitro, cyano, halogen, $C_1$-$C_4$-alkyl, $C_1$-$C_4$-haloalkyl, $C_1$-$C_4$-alkoxy or $C_1$-$C_4$-haloalkoxy, $X^2$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, $X^3$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, and/or the following compounds, defined by general formulae, of the general formula (IId)

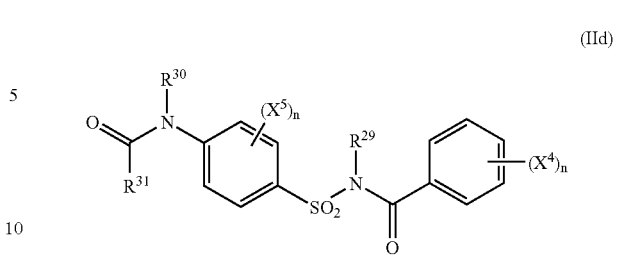

or of the general formula (IIe)

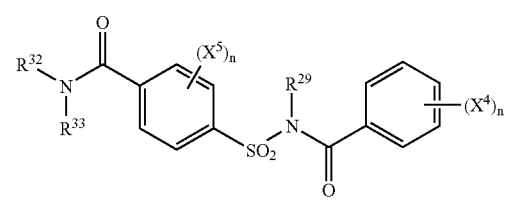

where n represents a number between 0 and 5, $R^{29}$ represents hydrogen or $C_1$-$C_4$-alkyl, $R^{30}$ represents hydrogen or $C_1$-$C_4$-alkyl, $R^{31}$ represents hydrogen, in each case optionally cyano-, halogen- or $C_1$-$C_4$-alkoxy-substituted $C_1$-$C_6$-alkyl, $C_1$-$C_6$-alkoxy, $C_1$-$C_6$-alkylthio, $C_1$-$C_6$-alkylamino or di-($C_1$-$C_4$-alkyl)amino, or in each case optionally cyano-, halogen- or $C_1$-$C_4$-alkyl-substituted $C_3$-$C_6$-cycloalkyl, $C_3$-$C_6$-cycloalkyloxy, $C_3$-$C_6$-cycloalkylthio or $C_3$-$C_6$-cycloalkylamino, $R^{32}$ represents hydrogen, optionally cyano-, hydroxyl-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, or optionally cyano-, halogen- or $C_1$-$C_4$-alkyl-substituted $C_3$-$C_6$-cycloalkyl, $R^{33}$ represents hydrogen, optionally cyano-, hydroxyl-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, optionally cyano-, halogen- or $C_1$-$C_4$-alkyl-substituted $C_3$-$C_6$-cycloalkyl, or optionally nitro-, cyano-, halogen-, $C_1$-$C_4$-alkyl-, $C_1$-$C_4$-halo-alkyl-, $C_1$-$C_4$-alkoxy- or $C_1$-$C_4$-haloalkoxy-substituted phenyl, or together with $R^{32}$ represents in each case optionally $C_1$-$C_4$-alkyl-substituted $C_2$-$C_6$-alkanediyl or $C_2$-$C_5$-oxaalkanediyl, $X^4$ represents nitro, cyano, carboxyl, carbamoyl, formyl, sulfamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy, and $X^5$ represents nitro, cyano, carboxyl, carbamoyl, formyl, sulfamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy.

The formula (I) provides a general definition of the compounds according to the invention. Preferred substituents or ranges of the radicals given in the formulae mentioned above and below are illustrated below:

Het represents

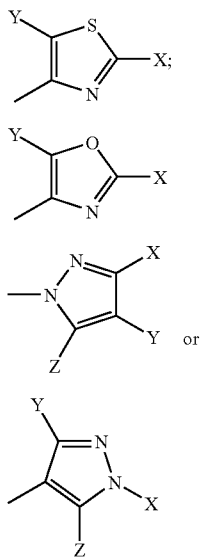

(I-1)

(I-2)

(I-3)

(I-4)

X preferably represents $C_1$-$C_6$-alkyl, $C_1$-$C_4$-haloalkyl, represents optionally halogen-, $C_1$-$C_6$-alkyl-, $C_1$-$C_6$-alkoxy-, $C_1$-$C_4$-haloalkyl-, $C_1$-$C_4$-haloalkoxy-, nitro- or cyano-substituted phenyl, Y preferably represents hydrogen, $C_1$-$C_6$-alkyl, chlorine or bromine, Z preferably represents $C_1$-$C_6$-alkyl, hydroxyl, $C_1$-$C_6$-alkoxy, $C_1$-$C_6$-haloalkoxy or in each case optionally $C_1$-$C_6$-alkyl-, $C_1$-$C_6$-alkoxy-, halogen-, $C_1$-$C_4$-haloalkyl-, $C_1$-$C_6$-haloalkoxy-, cyano- or nitro-substituted phenyl-$C_1$-$C_2$-alkyloxy or hetaryl-$C_1$-$C_2$-alkyloxy or optionally $C_1$-$C_2$-alkyl- or halogen-substituted $C_3$-$C_6$-cycloalkyl, A preferably represents hydrogen, in each case optionally halogen-substituted $C_1$-$C_6$-alkyl, $C_1$-$C_6$-alkenyl or $C_1$-$C_4$-alkoxy-$C_1$-$C_3$-alkyl, D preferably represents hydrogen, in each case optionally halogen-substituted $C_1$-$C_{12}$-alkyl, $C_3$-$C_8$-alkenyl, $C_3$-$C_8$-alkynyl, $C_1$-$C_{10}$-alkoxy-$C_1$-$C_8$-alkyl, poly-$C_1$-$C_8$-alkoxy-$C_1$-$C_8$-alkyl, $C_1$-$C_{10}$-alkylthio-$C_2$-$C_8$-alkyl, optionally halogen-, $C_1$-$C_4$-alkyl-, $C_1$-$C_4$-haloalkyl-, $C_1$-$C_4$-alkoxy- or $C_1$-$C_4$-haloalkyl-substituted $C_3$-$C_8$-cycloalkyl in which optionally one ring member is replaced by oxygen or sulfur, or represents in each case optionally halogen-, $C_1$-$C_6$-alkyl-, $C_1$-$C_6$-haloalkyl-, $C_1$-$C_6$-alkoxy-, $C_1$-$C_6$-haloalkoxy-, cyano- or nitro-substituted phenyl, hetaryl having 5 or 6 ring atoms (for example furanyl, imidazolyl, pyridyl, thiazolyl, pyrazolyl, pyrimidyl, pyrrolyl, thienyl or triazolyl), phenyl-$C_1$-$C_6$-alkyl or hetaryl-$C_1$-$C_6$-alkyl having 5 or 6 ring atoms (for example furanyl, imidazolyl, pyridyl, thiazolyl, pyrazolyl, pyrimidyl, pyrrolyl, thienyl or triazolyl) or A and D preferably together represent in each case optionally substituted $C_3$-$C_6$-alkanediyl or $C_3$-$C_6$-alkenediyl in which optionally one methylene group is replaced by nitrogen, oxygen or sulfur, possible substituents being in each case:
halogen, hydroxyl, mercapto or in each case optionally halogen-substituted $C_1$-$C_{10}$-alkyl. $C_1$-$C_6$-alkoxy, $C_1$-$C_6$-alkylthio, $C_3$-$C_7$-cycloalkyl, phenyl or benzyloxy, or a further $C_3$-$C_6$-alkanediyl grouping, $C_3$-$C_6$-alkenediyl grouping or a butadienyl grouping which is optionally substituted by $C_1$-$C_6$-alkyl or which optionally contains one of the following groups

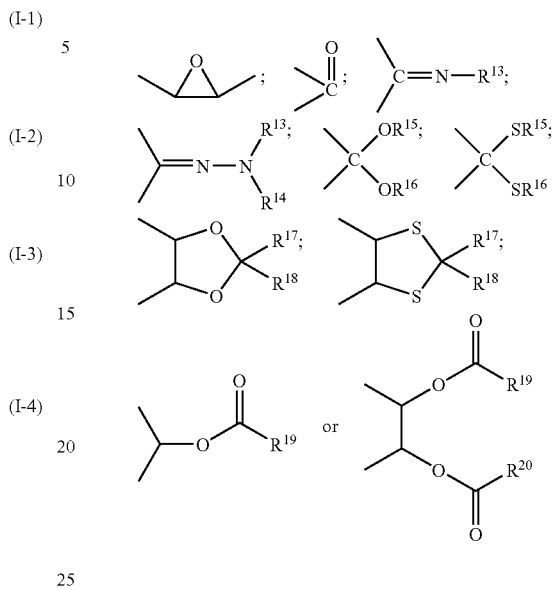

G preferably represents hydrogen (a) or represents one of the groups

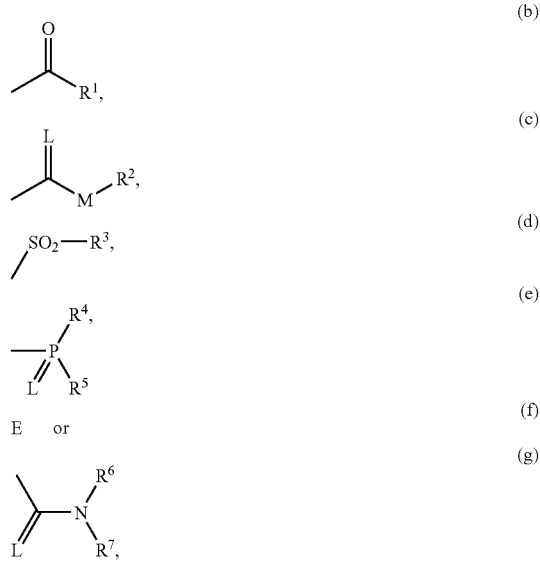

(b)

(c)

(d)

(e)

(f)

(g)

, in particular (a), (b), (c) or (g), in which

E represents a metal ion equivalent or an ammonium ion,

L represents oxygen or sulfur and

M represents oxygen or sulfur, $R^1$ preferably represents in each case optionally halogen-substituted $C_1$-$C_{20}$-alkyl, $C_2$-$C_{20}$-alkenyl, $C_1$-$C_8$-alkoxy-$C_1$-$C_8$-alkyl, $C_1$-$C_8$-alkylthio-$C_1$-$C_8$-alkyl, poly-$C_1$-$C_8$-alkoxy-$C_1$-$C_8$-alkyl or optionally halogen-, $C_1$-$C_6$-alkyl- or $C_1$-$C_6$-alkoxy-substituted $C_3$-$C_8$-cycloalkyl in which optionally one or more (preferably not more than two) not directly adjacent ring members are replaced by oxygen and/or sulfur, preferably represents optionally halogen-, cyano-, nitro-, $C_1$-$C_6$-alkyl-, $C_1$-$C_6$-alkoxy-, $C_1$-$C_6$-haloalkyl-, $C_1$-$C_6$-haloalkoxy-, $C_1$-$C_6$-alkylthio- or $C_1$-$C_6$-alkylsulfonyl-substituted phenyl, preferably represents optionally halogen-, nitro-, cyano-, $C_1$-$C_6$-alkyl-, $C_1$-$C_6$-alkoxy-, $C_1$-$C_6$-haloalkyl- or $C_1$-$C_6$-haloalkoxy-substituted phenyl-$C_1$-$C_6$-alkyl, preferably represents optionally halogen-, $C_1$-$C_6$-alkyl-, $C_1$-$C_2$-haloalkyl- or $C_1$-$C_4$-alkoxy-substituted 5- or 6-membered hetaryl (for example pyrazolyl, thiazolyl, pyridyl, pyrimidyl, furanyl or thienyl), preferably represents optionally halogen- or $C_1$-$C_6$-alkyl-substituted phenoxy-$C_1$-$C_6$-alkyl or preferably represents optionally halogen-, amino- or $C_1$-$C_6$-alkyl-substituted 5- or 6-membered hetaryloxy-$C_1$-$C_6$-alkyl (for example pyridyloxy-$C_1$-$C_6$-alkyl, pyrimidyloxy-$C_1$-$C_6$-alkyl or thiazolyloxy-$C_1$-$C_6$-alkyl), $R^2$ preferably represents in each case optionally halogen-substituted $C_1$-$C_{20}$-alkyl, $C_2$-$C_{20}$-alkenyl, $C_1$-$C_8$-alkoxy-$C_2$-$C_8$-alkyl, poly-$C_1$-$C_8$-alkoxy-$C_2$-$C_8$-alkyl, preferably represents optionally halogen-, $C_1$-$C_6$-alkyl- or $C_1$-$C_6$-alkoxy-substituted $C_3$-$C_8$-cycloalkyl in which optionally one ring atom is replaced by oxygen, or preferably represents in each case optionally halogen-, cyano-, nitro-, $C_1$-$C_6$-alkyl-, $C_1$-$C_6$-alkoxy-, $C_1$-$C_6$-haloalkyl- or $C_1$-$C_6$-haloalkoxy-substituted phenyl or benzyl, $R^3$ preferably represents optionally halogen-substituted $C_1$-$C_8$-alkyl or represents in each case optionally halogen-, $C_1$-$C_6$-alkyl-, $C_1$-$C_6$-alkoxy-, $C_1$-$C_4$-haloalkyl-, $C_1$-$C_4$-haloalkoxy-, cyano- or nitro-substituted phenyl or benzyl, $R^4$ and $R^5$ independently of one another preferably represent in each case optionally halogen-substituted $C_1$-$C_8$-alkyl, $C_1$-$C_8$-alkoxy, $C_1$-$C_8$-alkylamino, di-($C_1$-$C_8$-alkyl)amino, $C_1$-$C_8$-alkylthio, $C_2$-$C_8$-alkenylthio, $C_3$-$C_7$-cycloalkylthio or represent in each case optionally halogen-, nitro-, cyano-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkyl- or $C_1$-$C_4$-haloalkyl-substituted phenyl, phenoxy or phenylthio, $R^6$ and $R^7$ independently of one another preferably represent hydrogen, represent in each case optionally halogen-substituted $C_1$-$C_8$-alkyl, $C_3$-$C_8$-cycloalkyl, $C_1$-$C_8$-alkoxy, $C_3$-$C_8$-alkenyl, $C_1$-$C_8$-alkoxy-$C_1$-$C_8$-alkyl, represent optionally halogen-, $C_1$-$C_8$-haloalkyl-, $C_1$-$C_8$-alkyl- or $C_1$-$C_8$-alkoxy-substituted phenyl, optionally halogen-, $C_1$-$C_8$-alkyl-, $C_1$-$C_8$-haloalkyl- or $C_1$-$C_8$-alkoxy-substituted benzyl or together represent an optionally $C_1$-$C_4$-alkyl-substituted $C_3$-$C_6$-alkylene radical in which optionally one carbon atom is replaced by oxygen or sulfur, $R^{13}$ preferably represents in each case optionally halogen-substituted $C_1$-$C_4$-alkyl or $C_1$-$C_4$-alkoxy or represents in each case optionally $C_1$-$C_2$-alkyl- or $C_1$-$C_2$-alkoxy-substituted cyclopropyl or cyclohexyl, or $R^{14}$ preferably represents hydrogen or $C_1$-$C_8$-alkyl, or $R^{13}$ and $R^{14}$ together preferably represent $C_4$-$C_6$-alkanediyl, $R^{15}$ and $R^{16}$ are identical or different and preferably represent $C_1$-$C_4$-alkyl, or $R^{15}$ and $R^{16}$ together preferably represent a $C_2$-$C_4$-alkanediyl radical which is optionally mono- or disubstituted by $C_1$-$C_4$-alkyl, $R^{17}$ and $R^{18}$ independently of one another preferably represent hydrogen, represent optionally halogen-substituted $C_1$-$C_6$-alkyl or represent optionally halogen-, $C_1$-$C_6$-alkyl-, $C_1$-$C_6$-alkoxy-, $C_1$-$C_4$-haloalkyl-, $C_1$-$C_4$-haloalkoxy-, nitro- or cyano-substituted phenyl, or $R^{17}$ and $R^{18}$ together with the carbon atom to which they are attached preferably represent a carbonyl group or represent optionally $C_1$-$C_2$-alkyl- or $C_1$-$C_2$-alkoxy-substituted $C_5$-$C_7$-cycloalkyl in which optionally one methylene group is replaced by oxygen or sulfur, $R^{19}$ and $R^{20}$ independently of one another preferably represent $C_1$-$C_4$-alkyl, $C_2$-$C_4$-alkenyl, $C_1$-$C_4$-alkoxy, $C_1$-$C_4$-alkylamino, $C_3$-$C_4$-alkenylamino, di-($C_1$-$C_4$-alkyl)amino or di-($C_3$-$C_4$-alkenyl)amino.

In the radical definitions mentioned as being preferred, halogen represents fluorine, chlorine, bromine and iodine, in particular fluorine, chlorine and bromine.

Het particularly preferably represents

(I-1)

(I-2)

(I-3)

(I-4)

X particularly preferably $C_1$-$C_4$-alkyl, $C_1$-$C_2$-haloalkyl, represents phenyl which is optionally-mono- to trisubstituted by fluorine, chlorine, bromine, $C_1$-$C_4$-alkyl, $C_1$-$C_4$-alkoxy, $C_1$-$C_2$-haloalkyl, $C_1$-$C_2$-haloalkoxy, nitro or cyano, Y particularly preferably represents hydrogen, $C_1$-$C_4$-alkyl or, in the case of Het (I-1) and (I-3), also represents chlorine or bromine, Z particularly preferably represents $C_1$-$C_4$-alkyl, $C_1$-$C_4$-alkoxy, $C_1$-$C_4$-haloalkoxy or represents benzyloxy or hetarylmethyloxy having 5 or 6 ring atoms (for example furanyl, pyridyl, pyrimidyl, thiazolyl and thienyl), each of which radicals is optionally mono- or disubstituted by $C_1$-$C_4$-alkyl, $C_1$-$C_4$-alkoxy, fluorine, chlorine, bromine, $C_1$-$C_2$-haloalkyl, $C_1$-$C_2$-haloalkoxy, cyano or nitro, A particularly preferably represents hydrogen or represents $C_1$-$C_4$-alkyl, $C_1$-$C_4$-alkenyl or $C_1$-$C_3$-alkoxy-$C_1$-$C_2$-alkyl, each of which is optionally mono- to trisubstituted by fluorine, D particularly preferably represents hydrogen, represents $C_1$-$C_{10}$-alkyl, $C_3$-$C_6$-alkenyl, $C_1$-$C_6$-alkoxy-$C_1$-$C_4$-alkyl or $C_1$-$C_6$-alkylthio-$C_1$-$C_4$-alkyl, each of which is optionally mono- to trisubstituted by fluorine, represents $C_3$-$C_7$-cycloalkyl in which optionally one methylene group is replaced by oxygen or sulfur and which is optionally monosubstituted by fluorine, $C_1$-$C_4$-alkyl, $C_1$-$C_4$-alkoxy or $C_1$-$C_2$-haloalkyl, or represents in each case optionally fluorine-, chlorine-, bromine-, $C_1$-$C_4$-alkyl-, $C_1$-$C_2$-haloalkyl-, $C_1$-$C_4$-alkoxy- or $C_1$-$C_2$-haloalkoxy-substituted phenyl or phenyl-$C_1$-$C_4$-alkyl, or A and D together particularly preferably represent optionally mono- or disubstituted $C_3$-$C_5$-alkanediyl or $C_3$-$C_5$-alkenediyl in which optionally one methylene group may be replaced by a carbonyl group, oxygen or sulfur, possible substituents being hydroxyl, $C_1$-$C_6$-alkyl or $C_1$-$C_4$-alkoxy, G particularly preferably represents hydrogen (a) or represents one of the groups

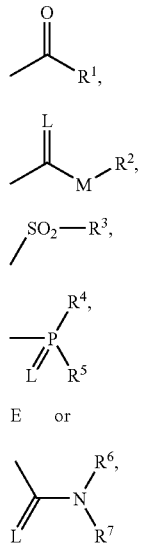

in particular (a), (b), (c) or (g),
in which
E represents a metal ion equivalent or an ammonium ion,
L represents oxygen or sulfur and
M represents oxygen or sulfur, $R^1$ particularly preferably represents $C_1$-$C_{16}$-alkyl, $C_2$-$C_{16}$-alkenyl, $C_1$-$C_6$-alkoxy-$C_1$-$C_4$-alkyl, $C_1$-$C_6$-alkylthio-$C_1$-$C_4$-alkyl, each of which is optionally mono- to pentasubstituted by fluorine or chlorine, or represents $C_3$-$C_7$-cycloalkyl in which optionally one or two not directly adjacent ring members are replaced by oxygen and/or sulfur and which is optionally mono- or disubstituted by fluorine, chlorine, $C_1$-$C_5$-alkyl or $C_1$-$C_5$-alkoxy, particularly preferably represents phenyl which is optionally mono- or disubstituted by fluorine chlorine, bromine, cyano, nitro, $C_1$-$C_4$-alkyl, $C_1$-$C_4$-alkoxy, $C_1$-$C_3$-haloalkyl, $C_1$-$C_3$-haloalkoxy, $C_1$-$C_4$-alkylthio or $C_1$-$C_4$-alkylsulfonyl, particularly preferably represents phenyl-$C_1$-$C_4$-alkyl which is optionally mono- or disubstituted by fluorine, chlorine, bromine, $C_1$-$C_4$-alkyl, $C_1$-$C_4$-alkoxy, $C_1$-$C_3$-haloalkyl or $C_1$-$C_3$-haloalkoxy, particularly preferably represents pyrazolyl, thiazolyl, pyridyl, pyrimidyl, furanyl or thienyl, each of which is optionally mono- or disubstituted by fluorine, chlorine, bromine, $C_1$-$C_4$-alkyl, trifluoromethyl or $C_1$-$C_2$-alkoxy, $R^2$ particularly preferably represents $C_1$-$C_{16}$-alkyl, $C_2$-$C_{16}$-alkenyl or $C_1$-$C_6$-alkoxy-$C_2$-$C_6$-alkyl, each of which is optionally mono- to pentasubstituted by fluorine, particularly preferably represents $C_3$-$C_7$-cycloalkyl which is optionally mono- or disubstituted by fluorine, chlorine, $C_1$-$C_4$-alkyl or $C_1$-$C_4$-alkoxy, or particularly preferably represents phenyl or benzyl, each of which is optionally mono- or disubstituted by fluorine, chlorine, bromine, cyano, nitro, $C_1$-$C_4$-alkyl, $C_1$-$C_3$-alkoxy, $C_1$-$C_2$-haloalkyl or $C_1$-$C_2$-haloalkoxy, $R^3$ particularly preferably represents $C_1$-$C_6$-alkyl which is optionally mono- to pentasubstituted by fluorine or represents phenyl which is optionally mono- or disubstituted by fluorine, chlorine, bromine, $C_1$-$C_4$-alkyl, $C_1$-$C_4$-alkoxy, $C_1$-$C_3$-haloalkyl, $C_1$-$C_3$-haloalkoxy, cyano or nitro, $R^4$ particularly preferably represents $C_1$-$C_6$-alkyl, $C_1$-$C_6$-alkoxy, $C_1$-$C_6$-alkylamino, di-($C_1$-$C_6$-alkyl)amino, $C_1$-$C_6$-alkylthio, $C_3$-$C_4$-alkenylthio, $C_3$-$C_6$-cycloalkylthio, each of which is optionally mono- to trisubstituted by fluorine, or represents phenyl, phenoxy or phenylthio, each of which is optionally mono- or disubstituted by fluorine, chlorine, bromine, nitro, cyano, $C_1$-$C_3$-alkoxy, $C_1$-$C_3$-haloalkoxy, $C_1$-$C_3$-alkylthio, $C_1$-$C_3$-haloalkylthio, $C_1$-$C_3$-alkyl or $C_1$-$C_3$-haloalkyl $R^5$ particularly preferably represents $C_1$-$C_6$-alkoxy or $C_1$-$C_6$-alkylthio, $R^6$ particularly preferably represents $C_1$-$C_6$-alkyl, $C_3$-$C_6$-cycloalkyl, $C_1$-$C_6$-alkoxy, $C_3$-$C_6$-alkenyl, $C_1$-$C_6$-alkoxy-$C_1$-$C_6$-alkyl, each of which is mono- to trisubstituted by fluorine, represents phenyl which is optionally mono- or disubstituted by fluorine, chlorine, bromine, $C_1$-$C_3$-haloalkyl, $C_1$-$C_4$-alkyl or $C_1$-$C_4$-alkoxy, represents benzyl which is optionally mono- or disubstituted by fluorine, chlorine, bromine, $C_1$-$C_4$-alkyl, $C_1$-$C_3$-haloalkyl or $C_1$-$C_4$-alkoxy, $R^7$ particularly preferably represents hydrogen, $C_1$$C_6$-alkyl, $C_3$-$C_6$-alkenyl, or $R^6$ and $R^7$ together particularly preferably represent a $C_4$-$C_5$-alkylene radical in which optionally one methylene group is replaced by oxygen or sulfur and which is optionally mono- or disubstituted by methyl or ethyl.

In the radical definitions mentioned as being particularly preferred, halogen represents fluorine, chlorine, bromine and iodine, in particular fluorine, chlorine and bromine.

Het very particularly preferably represents

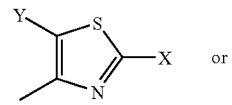

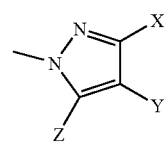

X very particularly preferably represents methyl, ethyl, propyl, trifluoromethyl, represents phenyl which is optionally mono- or disubstituted by fluorine, chlorine, bromine, methyl, ethyl, trifluoromethyl, isopropyl, tert-butyl, trifluoromethoxy, isopropoxy, tert-butoxy, cyano or nitro, Y very particularly preferably represents hydrogen in the case of Het (I-3) or represents methyl, ethyl, propyl, chlorine or bromine in the case of Het (I-1), Z very particularly preferably represents methyl, ethyl, propyl, isopropyl, methoxy, propoxy, isopropoxy, difluoromethoxy or trifluoroethoxy, A very particularly preferably represents hydrogen, methyl or ethyl, D very particularly preferably represents hydrogen, represents methyl, ethyl, allyl, each of which is optionally mono- to trisubstituted by fluorine, or represents phenyl which is optionally mono- or disubstituted by fluorine, chlorine, methyl, ethyl, n-propyl, isopropyl, methoxy, trifluoromethyl or trifluoromethoxy, or A and D together very particularly preferably represent optionally substituted $C_3$-$C_5$-alkanediyl in which optionally one carbon atom is replaced by oxygen and which is optionally mono- or disubstituted by methyl, ethyl, methoxy or ethoxy, G very particularly preferably represents hydrogen (a) or represents one of the groups

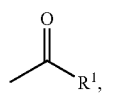
(b)

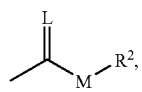
(c)

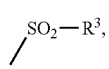
(d)

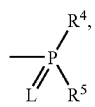
(e)

E or
(f)

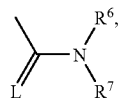
(g)

in particular (a), (b) or (c), in which

E represents a metal ion equivalent or an ammonium ion,

L represents oxygen or sulfur,

M represents oxygen or sulfur, $R^1$ very particularly preferably represents $C_1$-$C_8$-alkyl, $C_2$-$C_8$-alkenyl, $C_1$-$C_2$-alkoxy-$C_1$-$C_2$-alkyl, $C_1$-$C_2$-alkylthio-$C_1$-$C_2$-alkyl, each of which is optionally mono- to trisubstituted by fluorine, or represents cyclopropyl, cyclopentyl or cyclohexyl, each of which is optionally monosubstituted by fluorine, chlorine, methyl, ethyl or methoxy, very particularly preferably represents phenyl which is optionally mono- or disubstituted by fluorine, chlorine, bromine, cyano, nitro, methyl, ethyl, tert-butyl, methoxy, trifluoromethyl or trifluoromethoxy, very particularly preferably represents thienyl or pyridyl, each of which is optionally monosubstituted by fluorine, chlorine, bromine or methyl, $R^2$ very particularly preferably represents $C_1$-$C_8$-alkyl, $C_2$-$C_8$-alkenyl or $C_1$-$C_4$-alkoxy-$C_2$-$C_3$-alkyl, each of which is optionally mono- to trisubstituted by fluorine, very particularly preferably represents cyclohexyl which is optionally monosubstituted by fluorine, chlorine, methyl, ethyl, n-propyl, isopropyl or methoxy, or very particularly preferably represents phenyl or benzyl, each of which is optionally monosubstituted by fluorine, chlorine, cyano, nitro, methyl, ethyl, methoxy, trifluoromethyl or trifluoromethoxy, $R^3$ very particularly preferably represents methyl, ethyl, n-propyl or represents phenyl which is optionally monosubstituted by fluorine, chlorine, bromine, methyl, tert-butyl, methoxy, trifluoromethyl, trifluoromethoxy, cyano or nitro.

$R^4$ very particularly preferably represents $C_1$-$C_4$-alkyl, $C_1$-$C_4$-alkoxy, $C_1$-$C_4$-alkylamino, di-($C_1$-$C_4$-alkyl)amino, $C_1$-$C_4$-alkylthio, each of which is optionally mono- to trisubstituted by fluorine, or represents phenyl, phenoxy or phenylthio, each of which is optionally monosubstituted by fluorine, chlorine, bromine, nitro, cyano, $C_1$-$C_2$-alkoxy, $C_1$-$C_2$-fluoroalkoxy, $C_1$-$C_2$-alkylthio, $C_1$-$C_2$-fluoroalkylthio or $C_1$-$C_3$-alkyl, $R^5$ very particularly preferably represents methoxy, methylthio or ethylthio, $R^6$ very particularly preferably represents $C_1$-$C_4$-alkyl, $C_3$-$C_6$-cycloalkyl, $C_1$-$C_4$-alkoxy, $C_3$-$C_4$-alkenyl, $C_1$-$C_4$-alkoxy-$C_1$-$C_4$-alkyl, each of which is optionally mono- to trisubstituted by fluorine, represents phenyl which is optionally monosubstituted by fluorine, chlorine, bromine, trifluoromethyl, methyl or methoxy, represents benzyl which is optionally monosubstituted by fluorine, chlorine, bromine, methyl, trifluoromethyl or methoxy, $R^7$ very particularly preferably represents hydrogen, methyl, ethyl, propyl or allyl, or $R^6$ and $R^7$ together very particularly preferably represent a $C_5$-$C_6$-alkylene radical in which optionally one methylene group is replaced by oxygen or sulfur.

Het with emphasis represents

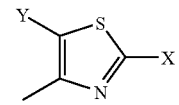
(I-1)

or

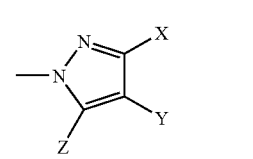
(I-3)

X with emphasis represents phenyl which is optionally mono- or disubstituted by fluorine, chlorine, bromine, methyl, trifluoromethyl, methoxy or trifluoromethoxy, Y with emphasis represents hydrogen in the case of Het (I-3) or methyl, ethyl or propyl in the case of Het (I-1), Z with emphasis represents methyl, ethyl, propyl or isopropyl, A with emphasis represents methyl or ethyl, D with emphasis represents methyl or ethyl, A and D with emphasis represent $C_3$-$C_5$-alkanediyl in which optionally one carbon atom is replaced by an oxygen atom, G with emphasis represents hydrogen (a) or represents one of the groups

(b)

-continued

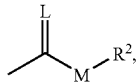
(c)

in which
L represents oxygen and
M represents oxygen,
R¹ with emphasis represents $C_1$-$C_8$-alkyl, $C_2$-$C_4$-alkenyl, $C_1$-$C_2$-alkoxy-$C_1$-$C_2$-alkyl, $C_1$-$C_2$-alkylthio-$C_1$-$C_2$-alkyl, cyclopropyl or cyclohexyl,
  with emphasis represents phenyl which is optionally monosubstituted by fluorine, chlorine, bromine, cyano, nitro, methyl, ethyl, tert-butyl, methoxy, tert-butoxy, trifluoromethyl or trifluoromethoxy,
  with emphasis represents pyridyl which is optionally monosubstituted by chlorine or methyl,
R² with emphasis represents $C_1$-$C_8$-alkyl, $C_2$-$C_4$-alkenyl or $C_1$-$C_4$-alkoxy-$C_2$-$C_3$-alkyl,
  or with emphasis represents phenyl or benzyl, each of which is optionally monosubstituted by fluorine, chlorine, cyano, nitro, methyl, ethyl, methoxy, trifluoromethyl or trifluoromethoxy.
Het in particular represents

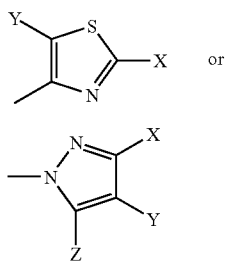

X in particular represents phenyl which is optionally monosubstituted by chlorine,
Y in particular represents hydrogen in the case of Het (I-3) or methyl or propyl in the case of Het (I-1),
Z in particular represents methyl,
A and D in particular represent $C_3$-$C_5$-alkanediyl in which optionally one carbon atom is replaced by an oxygen atom,
G in particular represents hydrogen (a) or represents one of the groups

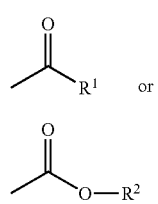

R¹ in particular represents $C_1$-$C_8$-alkyl,
R² in particular represents $C_1$-$C_8$-alkyl.
The general or preferred radical definitions or illustrations listed above can be combined with one another as desired, i.e. including combinations between the respective ranges and preferred ranges. They apply to the end products and, correspondingly, to the precursors and intermediates.

Preference according to the invention is given to the compounds of the formula (I) which contain a combination of the meanings listed above as being preferred (preferable).

Particular preference according to the invention is given to the compounds of the formula (I) which contain a combination of the meanings listed above as being particularly preferred.

Very particular preference according to the invention is given to the compounds of the formula (I) which contain a combination of the meanings listed above as being very particularly preferred.

Emphasis according to the invention is given to the compounds of the formula (I) which contain a combination of the meanings listed above as being emphasized.

Saturated or unsaturated hydrocarbon radicals, such as alkyl or alkenyl, can in each case be straight-chain or branched as far as this is possible, including in combination with heteroatoms, such as, for example, in alkoxy.

Unless indicated otherwise, optionally substituted radicals can be mono- or polysubstituted, where in the case of polysubstitutions the substituents can be identical or different, In addition to the compounds mentioned in the Preparation Examples, the compounds of the formula (I-1-a) below may be specifically mentioned.

TABLE 1

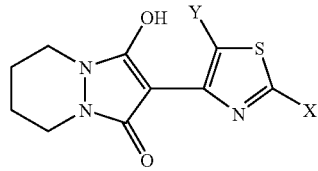

| Y | X |
|---|---|
| CH₃ | 4-F—Ph |
| CH₃ | 3-F—Ph |
| CH₃ | 3,4-F₂—Ph |
| CH₃ | 4-Cl—Ph |
| CH₃ | 3-Cl—Ph |
| CH₃ | 3,4-Cl₂—Ph |
| CH₃ | 3-F, 4-Cl—Ph |
| CH₃ | 4-F, 3-Cl—Ph |
| CH₃ | 4-CF₃—Ph |
| CH₃ | 3-CF₃—Ph |
| CH₃ | 4-CF₃, 3-F—Ph |
| CH₃ | 3-CF₃, 4-F—Ph |
| CH₃ | 4-CF₃-3-Cl—Ph |
| CH₃ | 3-CF₃-4-Cl—Ph |
| CH₃ | 4-Br—Ph |
| CH₃ | 3-Br—Ph |

TABLE 2

| X | as stated in table 1 |
|---|---|
| Y = | C₂H₅ |
| X | as stated in table 1 |
| Y = | C₃H₇ |

TABLE 3

| X | as stated in table 1 |
|---|---|
| Y = | C₃H₇ |

TABLE 4

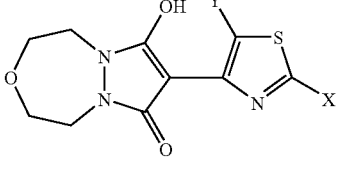

| Y | X |
|---|---|
| CH₃ | 4-F—Ph |
| CH₃ | 3-F—Ph |
| CH₃ | 3,4-F₂—Ph |
| CH₃ | 4-Cl—Ph |
| CH₃ | 3-Cl—Ph |
| CH₃ | 3,4-Cl₂—Ph |
| CH₃ | 3-F, 4-Cl—Ph |
| CH₃ | 4-F, 3-Cl—Ph |
| CH₃ | 4-CF₃—Ph |
| CH₃ | 3-CF₃—Ph |
| CH₃ | 4-CF₃, 3-F—Ph |
| CH₃ | 3-CF₃, 4-F—Ph |
| CH₃ | 4-CF₃-3-Cl—Ph |
| CH₃ | 3-CF₃-4-Cl—Ph |
| CH₃ | 4-Br—Ph |
| CH₃ | 3-Br—Ph |

TABLE 5

| X | as stated in table 4 |
|---|---|
| Y = | C₂H₅ |

TABLE 6

| X | as stated in table 4 |
|---|---|
| Y = | C₃H₇ |

In addition to the compounds mentioned in the Preparation Examples, the following compounds of the formula (I-3-a) may be specifically mentioned:

TABLE 7

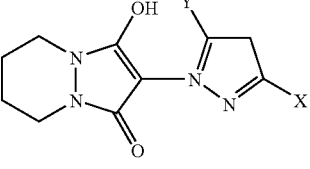

| Z | X |
|---|---|
| CH₃ | 4-F—Ph |
| CH₃ | 3-F—Ph |
| CH₃ | 3,4-F₂—Ph |
| CH₃ | 4-Cl—Ph |
| CH₃ | 3-Cl—Ph |
| CH₃ | 3,4-Cl₂—Ph |
| CH₃ | 3-F, 4-Cl—Ph |
| CH₃ | 4-F, 3-Cl—Ph |
| CH₃ | 4-CF₃—Ph |
| CH₃ | 3-CF₃—Ph |
| CH₃ | 4-CF₃, 3-F—Ph |
| CH₃ | 3-CF₃, 4-F—Ph |
| CH₃ | 4-CF₃-3-Cl—Ph |
| CH₃ | 3-CF₃-4-Cl—Ph |
| CH₃ | 4-Br—Ph |
| CH₃ | 3-Br—Ph |

TABLE 8

| X | as stated in table 7 |
|---|---|
| Z = | C₂H₅ |

TABLE 9

| X | as stated in table 7 |
|---|---|
| Z = | C₃H₇ |

TABLE 10

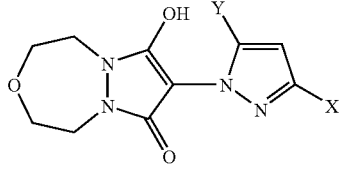

| Z | X |
|---|---|
| CH₃ | 4-F—Ph |
| CH₃ | 3-F—Ph |
| CH₃ | 3,4-F₂—Ph |
| CH₃ | 4-Cl—Ph |
| CH₃ | 3-Cl—Ph |
| CH₃ | 3,4-Cl₂—Ph |
| CH₃ | 3-F, 4-Cl—Ph |
| CH₃ | 4-F, 3-Cl—Ph |
| CH₃ | 4-CF₃—Ph |
| CH₃ | 3-CF₃—Ph |
| CH₃ | 4-CF₃, 3-F—Ph |
| CH₃ | 3-CF₃, 4-F—Ph |
| CH₃ | 4-CF₃-3-Cl—Ph |
| CH₃ | 3-CF₃-4-Cl—Ph |
| CH₃ | 4-Br—Ph |
| CH₃ | 3-Br—Ph |

TABLE 11

| X | as stated in table 10 |
|---|---|
| Z = | C₂H₅ |

TABLE 12

| X | as stated in table 10 |
|---|---|
| Z = | C₃H₇ |

Preferred meanings of the groups listed above in connection with the crop plant compatibility-improving compounds ("herbicide safeners") of the formulae (IIa), (IIb), (IIc), (IId) and (IIe) are defined below.

n preferably represents the numbers 0, 1, 2, 3 or 4.

$A^1$ preferably represents one of the divalent heterocyclic groupings shown below

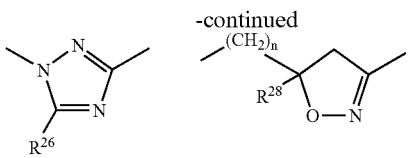

A² preferably represents in each case optionally methyl-, ethyl-, methoxycarbonyl- or ethoxycarbonyl-substituted methylene or ethylene.

R²¹ preferably represents hydroxyl, mercapto, amino, methoxy, n- or i-propoxy, n-, i-, s- or t-butoxy, methylthio, n- or i-propylthio, n-, i-, s- or t-butylthio, methylamino, ethylamino, n- or i-propylamino, n-, i-, s- or t-butylamino, dimethylamino or diethylamino.

R²² preferably represents hydroxyl, mercapto, amino, methoxy, n- or i-propoxy, n-, i-, s- or t-butoxy, methylthio, n- or i-propylthio, n-, i-, s- or t-butylthio, methylamino, ethylamino, n- or i-propylamino, n-, i-, s- or t-butylamino, dimethylamino or diethylamino.

R²³ preferably represents in each case optionally fluorine-, chlorine- and/or bromine-substituted methyl, ethyl, n- or i-propyl.

R²⁴ preferably represents hydrogen, in each case optionally fluorine- and/or chlorine-substituted methyl, ethyl, n- or i-propyl, n-, i-, s- or t-butyl, propenyl, butenyl, propynyl or butynyl, methoxymethyl, ethoxymethyl, methoxyethyl, ethoxyethyl, dioxolanylmethyl, furyl, furylmethyl, thienyl, thiazolyl, piperidinyl, or optionally fluorine-, chlorine-, methyl-, ethyl-, n- or i-propyl-, n-, i-, s- or t-butyl-substituted phenyl.

R²⁵ preferably represents hydrogen, in each case optionally fluorine- and/or chlorine-substituted methyl, ethyl, n- or i-propyl, n-, i-, s- or t-butyl, propenyl, butenyl, propynyl or butynyl, methoxymethyl, ethoxymethyl, methoxyethyl, ethoxyethyl, dioxolanylmethyl, furyl, furylmethyl, thienyl, thiazolyl, piperidinyl, or optionally fluorine-, chlorine-, methyl-, ethyl-, n- or i-propyl-, n-, i-, s- or t-butyl-substituted phenyl, or together with R²⁴ represents one of the radicals —CH₂—O—CH₂—CH₂— and —CH₂—CH₂—O—CH₂—CH₂— which are optionally substituted by methyl, ethyl, furyl, phenyl, a fused benzene ring or by two substituents which, together with the C atom to which they are attached, form a 5- or 6-membered carbocycle.

R²⁶ preferably represents hydrogen, cyano, fluorine, chlorine, bromine, or represents in each case optionally fluorine-, chlorine- and/or bromine-substituted methyl, ethyl, n- or i-propyl, cyclopropyl, cyclobutyl, cyclopentyl, cyclohexyl or phenyl.

R²⁷ preferably represents hydrogen, in each case optionally hydroxyl-, cyano-, fluorine-, chlorine-, methoxy-, ethoxy-, n- or i-propoxy-substituted methyl, ethyl, n- or i-propyl, n-, i-, s- or t-butyl.

R²⁸ preferably represents hydrogen, cyano, fluorine, chlorine, bromine, or represents in each case optionally fluorine-, chlorine- and/or bromine-substituted methyl, ethyl, n- or i-propyl, n-, i-, s- or t-butyl, cyclopropyl, cyclobutyl, cyclopentyl, cyclohexyl or phenyl.

X¹ preferably represents nitro, cyano, fluorine, chlorine, bromine, methyl, ethyl, n- or i- propyl, n-, i-, s- or t-butyl, difluoromethyl, dichloromethyl, trifluoromethyl, trichloromethyl, chlorodifluoromethyl, fluorodichloromethyl, methoxy, n- or i-propoxy, difluoromethoxy or trifluoromethoxy.

X² preferably represents hydrogen, nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, n- or i-propoxy, difluoromethoxy or trifluoromethoxy.

X³ preferably represents hydrogen, nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, n- or i-propoxy, difluoromethoxy or trifluoromethoxy.

R²⁹ preferably represents hydrogen, methyl, ethyl, n- or i-propyl.

R³⁰ preferably represents hydrogen, methyl, ethyl, n- or i-propyl.

R³¹ preferably represents hydrogen, in each case optionally cyano-, fluorine-, chlorine-, methoxy-, ethoxy-, n- or i-propoxy-substituted methyl, ethyl, n- or i-propyl, n-, i-, s- or t-butyl, methoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino, or in each case optionally cyano-, fluorine-, chlorine-, bromine-, methyl-, ethyl-, n- or i-propyl-substituted cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino or cyclohexylamino.

R³² preferably represents hydrogen, in each case optionally cyano-, hydroxyl-, fluorine-, chlorine-, methoxy-, ethoxy-, n- or i-propoxy-substituted methyl, ethyl, n- or i-propyl, n-, i- or s-butyl, in each case optionally cyano-, fluorine-, chlorine- or bromine-substituted propenyl, butenyl, propynyl or butynyl, or in each case optionally cyano-, fluorine-, chlorine-, bromine-, methyl-, ethyl-, n- or i-propyl-substituted cyclopropyl, cyclobutyl, cyclopentyl or cyclohexyl.

R³³ preferably represents hydrogen, in each case optionally cyano-, hydroxyl-, fluorine-, chlorine-, methoxy-, ethoxy-, n- or i-propoxy-substituted methyl, ethyl, n- or i-propyl, n-, i- or s-butyl, in each case optionally cyano-, fluorine-, chlorine- or bromine-substituted propenyl, butenyl, propynyl or butynyl, in each case optionally cyano-, fluorine-, chlorine-, bromine-, methyl-, ethyl-, n- or i-propyl-substituted cyclopropyl, cyclobutyl, cyclopentyl or cyclohexyl, or optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted phenyl, or together with R³² represents in each case optionally, methyl- or ethyl-substituted butane-1,4-diyl(trimethylene), pentane-1,5-diyl, 1-oxabutane-1,4-diyl or 3-oxapentane-1,5-diyl.

X⁴ preferably represents nitro, cyano, carboxyl, carbamoyl, formyl, sulfamoyl, hydroxyl, amino, fluorine, chlorine, bromine, methyl, ethyl, n- or i-propyl, n-, i-, s- or t-butyl, trifluoromethyl, methoxy, n- or i-propoxy, difluoromethoxy or trifluoromethoxy.

X⁵ preferably represents nitro, cyano, carboxyl, carbamoyl, formyl, sulfamoyl, hydroxyl, amino, fluorine, chlorine, bromine, methyl, ethyl, n- or i-propyl, n-, i-, s- or t-butyl, trifluoromethyl, methoxy, n- or i-propoxy, difluoromethoxy or trifluoromethoxy.

Examples of the compounds of the formula (IIa) which are very particularly preferred as herbicide safeners according to the invention are listed in table 13 below.

TABLE 13

Examples of the compounds of the formula (IIa)

(IIa)

Structure: $(X^1)_n$-phenyl-$A^1$-C(=O)-$R^{21}$ (positions 2, 3, 4 on phenyl)

| Example No. | (positions) $(X^1)_n$ | $A^1$ | $R^{21}$ |
|---|---|---|---|
| IIa-1 | (2) Cl, (4) Cl | 1-methyl-3-methyl-5-(methoxycarbonyl)-5-methyl-4,5-dihydropyrazol-5-yl | OCH$_3$ |
| IIa-2 | (2) Cl, (4) Cl | 1-methyl-3-methyl-5-(ethoxycarbonyl)-5-methyl-4,5-dihydropyrazol-5-yl | OCH$_3$ |
| IIa-3 | (2) Cl, (4) Cl | 1-methyl-3-methyl-5-(methoxycarbonyl)-5-methyl-4,5-dihydropyrazol-5-yl | OC$_2$H$_5$ |
| IIa-4 | (2) Cl, (4) Cl | 1-methyl-3-methyl-5-(ethoxycarbonyl)-5-methyl-4,5-dihydropyrazol-5-yl | OC$_2$H$_5$ |
| IIa-5 | (2) Cl | 1-methyl-3-methyl-5-phenyl-pyrazol-5-yl | OCH$_3$ |
| IIa-6 | (2) Cl, (4) Cl | 1-methyl-3-methyl-5-phenyl-pyrazol-5-yl | OCH$_3$ |
| IIa-7 | (2) F | 1-methyl-3-methyl-5-phenyl-pyrazol-5-yl | OCH$_3$ |
| IIa-8 | (2) F | 1-methyl-3-methyl-5-(2-chlorophenyl)-pyrazol-5-yl | OCH$_3$ |
| IIa-9 | (2) Cl, (4) Cl | 1-methyl-3-methyl-5-(trichloromethyl)-1,2,4-triazol-5-yl | OC$_2$H$_5$ |
| IIa-10 | (2) Cl, (4) CF$_3$ | 1-methyl-3-methyl-5-phenyl-1,2,4-triazol-5-yl | OCH$_3$ |
| IIa-11 | (2) Cl | 1-methyl-3-methyl-5-(2-fluorophenyl)-pyrazol-5-yl | OCH$_3$ |
| IIa-12 | — | 3-methyl-5-methyl-5-phenyl-4,5-dihydroisoxazol-3-yl | OC$_2$H$_5$ |
| IIa-13 | (2) Cl, (4) Cl | 1,3-dimethyl-5-methyl-pyrazol-5-yl | OC$_2$H$_5$ |
| IIa-14 | (2) Cl, (4) Cl | 1,3-dimethyl-5-isopropyl-pyrazol-5-yl | OC$_2$H$_5$ |
| IIa-15 | (2) Cl, (4) Cl | 1,3-dimethyl-5-tert-butyl-pyrazol-5-yl | OC$_2$H$_5$ |

TABLE 13-continued

Examples of the compounds of the formula (IIa)

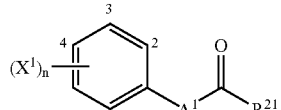

(IIa)

| Example No. | (positions) $(X^1)_n$ | $A^1$ | $R^{21}$ |
|---|---|---|---|
| IIa-16 | (2) Cl, (4) Cl | [CH2-(3-methyl-4,5-dihydroisoxazol-5-yl)] | $OC_2H_5$ |
| IIa-17 | (2) Cl, (4) Cl | [3,5-dimethyl-4,5-dihydroisoxazol-5-yl] | $OC_2H_5$ |
| IIa-18 | — | [3,5-dimethyl-5-phenyl-4,5-dihydroisoxazole] | OH |

Examples of the compounds of the formula (IIb) which are very particularly preferred as herbicide safeners according to the invention are listed in table 14 below.

TABLE 14

Examples of the compounds of the formula (IIb)

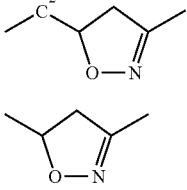

(IIb)

| Example No. | (position) $X^2$ | (position) $X^3$ | $A^2$ | $R^{22}$ |
|---|---|---|---|---|
| IIb-1 | (5) Cl | — | $CH_2$ | OH |
| IIb-2 | (5) Cl | — | $CH_2$ | $OCH_3$ |
| IIb-3 | (5) Cl | — | $CH_2$ | $OC_2H_5$ |
| IIb-4 | (5) Cl | — | $CH_2$ | $OC_3H_7$-n |
| IIb-5 | (5) Cl | — | $CH_2$ | $OC_3H_7$-i |
| IIb-6 | (5) Cl | — | $CH_2$ | $OC_4H_9$-n |
| IIb-7 | (5) Cl | — | $CH_2$ | $OCH(CH_3)C_5H_{11}$-n |
| IIb-8 | (5) Cl | (2) F | $CH_2$ | OH |
| IIb-9 | (5) Cl | (2) Cl | $CH_2$ | OH |
| IIb-10 | (5) Cl | — | $CH_2$ | $OCH_2CH=CH_2$ |
| IIb-11 | (5) Cl | — | $CH_2$ | $OC_4H_9$-i |
| IIb-12 | (5) Cl | — | $CH_2$ | [CH2=CH-CH2-O-CH2-CH(OCH3)CH3] |

TABLE 14-continued

Examples of the compounds of the formula (IIb)

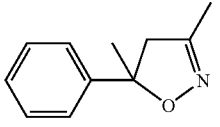

(IIb)

| Example No. | (position) $X^2$ | (position) $X^3$ | $A^2$ | $R^{22}$ |
|---|---|---|---|---|
| IIb-13 | (5) Cl | — | [CH(CH2CH=CH2)] | $OCH_2CH=CH_2$ |
| IIb-14 | (5) Cl | — | [CH(C2H5)] | $OC_2H_5$ |
| IIb-15 | (5) Cl | — | [CH(CH3)] | $OCH_3$ |

Examples of the compounds of the formula (IIc) which are very particularly preferred as herbicide safeners according to the invention are listed in table 15 below.

TABLE 15

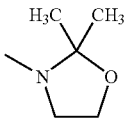

(IIc)

Examples of the compounds of the formula (IIc)

| Example No. | $R^{23}$ | $N(R^{24}, R^{25})$ |
|---|---|---|
| IIc-1 | $CHCl_2$ | $N(CH_2CH=CH_2)_2$ |
| IIc-2 | $CHCl_2$ | [2,2-dimethyl-3-methyl-1,3-oxazolidine] |

TABLE 15-continued

Examples of the compounds of the formula (IIc)

(IIc)

| Example No. | $R^{23}$ | $N(R^{24}, R^{25})$ |
|---|---|---|
| IIc-3 | $CHCl_2$ | 2,2,4-trimethyl-N-methyl-oxazolidine |
| IIc-4 | $CHCl_2$ | N-methyl-1-oxa-4-azaspiro[4.5]decane |
| IIc-5 | $CHCl_2$ | 2,2-dimethyl-5-phenyl-N-methyl-oxazolidine |
| IIc-6 | $CHCl_2$ | 3,4-dihydro-3,4-dimethyl-2H-1,4-benzoxazine |
| IIc-7 | $CHCl_2$ | 2,2-dimethyl-5-(2-furyl)-N-methyl-oxazolidine |

Examples of the compounds of the formula (IId) which are very particularly preferred as herbicide safeners according to the invention are listed in table 16 below.

TABLE 16

Examples of the compounds of the formula (IId)

(IId)

| Example No. | $R^{29}$ | $R^{30}$ | $R^{31}$ | (positions) $(X^4)_n$ | (positions) $(X^5)_n$ |
|---|---|---|---|---|---|
| IId-1 | H | H | $CH_3$ | (2) $OCH_3$ | — |
| IId-2 | H | H | $C_2H_5$ | (2) $OCH_3$ | — |
| IId-3 | H | H | $C_3H_7$-n | (2) $OCH_3$ | — |
| IId-4 | H | H | $C_3H_7$-i | (2) $OCH_3$ | — |
| IId-5 | H | H | cyclopropyl | (2) $OCH_3$ | — |
| IId-6 | H | H | $CH_3$ | (2) $OCH_3$ | (5) $CH_3$ |
| IId-7 | H | H | $C_2H_5$ | (2) $OCH_3$ | (5) $CH_3$ |
| IId-8 | H | H | $C_3H_7$-n | (2) $OCH_3$ | (5) $CH_3$ |
| IId-9 | H | H | $C_3H_7$-i | (2) $OCH_3$ | (5) $CH_3$ |
| IId-10 | H | H | cyclopropyl | (2) $OCH_3$ | (5) $CH_3$ |
| IId-11 | H | H | $OCH_3$ | (2) $OCH_3$ | (5) $CH_3$ |
| IId-12 | H | H | $OC_2H_5$ | (2) $OCH_3$ | (5) $CH_3$ |
| IId-13 | H | H | $OC_3H_7$-i | (2) $OCH_3$ | (5) $CH_3$ |
| IId-14 | H | H | $SCH_3$ | (2) $OCH_3$ | (5) $CH_3$ |
| IId-15 | H | H | $SC_2H_5$ | (2) $OCH_3$ | (5) $CH_3$ |
| IId-16 | H | H | $SC_3H_7$-i | (2) $OCH_3$ | (5) $CH_3$ |
| IId-17 | H | H | $NHCH_3$ | (2) $OCH_3$ | (5) $CH_3$ |
| IId-18 | H | H | $NHC_2H_5$ | (2) $OCH_3$ | (5) $CH_3$ |
| IId-19 | H | H | $NHC_3H_7$-i | (2) $OCH_3$ | (5) $CH_3$ |
| IId-20 | H | H | NH-cyclopropyl | (2) $OCH_3$ | (5) $CH_3$ |
| IId-21 | H | H | $NHCH_3$ | (2) $OCH_3$ | — |
| IId-22 | H | H | $NHC_3H_7$-i | (2) $OCH_3$ | — |
| IId-23 | H | H | $N(CH_3)_2$ | (2) $OCH_3$ | — |
| IId-24 | H | H | $N(CH_3)_2$ | (3) $CH_3$ (4) $CH_3$ | — |
| IId-25 | H | H | $CH_2$—O—$CH_3$ | (2) $OCH_3$ | — |

Examples of the compounds of the formula (IIe) which are very particularly preferred as herbicide safeners according to the invention are listed in table 17 below.

TABLE 17

Examples of the compounds of the formula (IIe)

(IIe)

[Structure: R$^{32}$R$^{33}$N-C(O)-phenyl(X$^5$)$_n$-SO$_2$-N(R$^{29}$)-C(O)-phenyl(X$^4$)$_n$]

| Example No. | R$^{29}$ | R$^{32}$ | R$^{33}$ | (positions) (X$^4$)$_n$ | (positions) (X$^5$)$_n$ |
|---|---|---|---|---|---|
| IIe-1 | H | H | CH$_3$ | (2) OCH$_3$ | — |
| IIe-2 | H | H | C$_2$H$_5$ | (2) OCH$_3$ | — |
| IIe-3 | H | H | C$_3$H$_7$-n | (2) OCH$_3$ | — |
| IIe-4 | H | H | C$_3$H$_7$-i | (2) OCH$_3$ | — |
| IIe-5 | H | H | cyclopropyl | (2) OCH$_3$ | — |
| IIe-6 | H | CH$_3$ | CH$_3$ | (2) OCH$_3$ | — |
| IIe-7 | H | H | CH$_3$ | (2) OCH$_3$ (5) CH$_3$ | — |
| IIe-8 | H | H | C$_2$H$_5$ | (2) OCH$_3$ (5) CH$_3$ | — |
| IIe-9 | H | H | C$_3$H$_7$-n | (2) OCH$_3$ (5) CH$_3$ | — |
| IIe-10 | H | H | C$_3$H$_7$-i | (2) OCH$_3$ (5) CH$_3$ | — |
| IIe-11 | H | H | cyclopropyl | (2) OCH$_3$ (5) CH$_3$ | — |
| IIe-12 | H | CH$_3$ | CH$_3$ | (2) OCH$_3$ (5) CH$_3$ | — |

Most preferred as crop plant compatibility-improving compounds [component (b')] are cloquintocet-mexyl, fenchlorazole-ethyl, isoxadifen-ethyl, mefenpyr-diethyl, furilazole, fenclorim, cumyluron, dymron, dimepiperate and the compounds IIe-5 and IIe-11, and particular emphasis is given to cloquintocet-mexyl and mefenpyr-diethyl.

The compounds of the general formula (IIa) to be used as safeners according to the invention are known and/or can be prepared by processes known per se (cf. WO-A-91/07874, WO-A-95/07897).

The compounds of the general formula (IIb) to be used as safeners according to the invention are known and/or can be prepared by processes known per se (cf. EP-A-191 736).

The compounds of the general formula (IIc) to be used as safeners according to the invention are known and/or can be prepared by processes known per se (cf. DE-A-2 218 097, DE-A-2 350 547).

The compounds of the general formula (IId) to be used as safeners according to the invention are known and/or can be prepared by processes known per se (cf. DE-A-19 621 522/ U.S. Pat. No. 6,235,680).

The compounds of the general formula (IIe) to be used as safeners according to the invention are known and/or can be prepared by processes known per se (cf. WO-A-99/66 795/ U.S. Pat. No. 6,251,827).

Examples of the selective herbicidal combinations according to the invention comprising in each case one active compound of the formula (I) and in each case one of the safeners defined above are listed in the table below.

TABLE

Examples of the combinations according to the invention

| Active compounds of the formula (I) | Safeners |
|---|---|
| I-a | cloquintocet-mexyl |
| I-a | fenchlorazole-ethyl |
| I-a | isoxadifen-ethyl |
| I-a | mefenpyr-diethyl |
| I-a | furilazole |
| I-a | fenclorim |
| I-a | cumyluron |
| I-a | daimuron/dymron |
| I-a | dimepiperate |
| I-a | IIe-11 |
| I-a | IIe-5 |
| I-b | cloquintocet-mexyl |
| I-b | fenchlorazole-ethyl |
| I-b | isoxadifen-ethyl |
| I-b | mefenpyr-diethyl |
| I-b | furilazole |
| I-b | fenclorim |
| I-b | cumyluron |
| I-b | daimuron/dymron |
| I-b | dimepiperate |
| I-b | IIe-11 |
| I-b | II-5 |
| I-c | cloquintocet-mexyl |
| I-c | fenchlorazole-ethyl |
| I-c | isoxadifen-ethyl |
| I-c | mefenpyr-diethyl |
| I-c | furilazole |
| I-c | fenclorim |
| I-c | cumyluron |
| I-c | daimuron/dymron |
| I-c | dimepiperate |
| I-c | IIe-5 |
| I-c | IIe-11 |
| I-d | cloquintocet-mexyl |
| I-d | fenchlorazole-ethyl |
| I-d | isoxadifen-ethyl |
| I-d | mefenpyr-diethyl |
| I-d | furilazole |
| I-d | fenclorim |
| I-d | cumyluron |
| I-d | daimuron/dymron |
| I-d | dimepiperate |
| I-d | IIe-11 |
| I-d | IIe-5 |
| I-e | cloquintocet-mexyl |
| I-e | fenchlorazole-ethyl |
| I-e | isoxadifen-ethyl |
| I-e | mefenpyr-diethyl |
| I-e | furilazole |
| I-e | fenclorim |
| I-e | cumyluron |
| I-e | daimuron/dymron |
| I-e | dimepiperate |
| I-e | IIe-5 |
| I-e | IIe-11 |
| I-f | cloquintocet-mexyl |
| I-f | fenchlorazole-ethyl |
| I-f | isoxadifen-ethyl |
| I-f | mefenpyr-diethyl |
| I-f | furilazole |
| I-f | fenclorim |
| I-f | cumyluron |

TABLE-continued

Examples of the combinations according to the invention

| Active compounds of the formula (I) | Safeners |
|---|---|
| I-f | daimuron/dymron |
| I-f | dimepiperate |
| I-f | IIe-5 |
| I-f | IIe-11 |
| I-g | cloquintocet-mexyl |
| I-g | fenchlorazole-ethyl |
| I-g | isoxadifen-ethyl |
| I-g | mefenpyr-diethyl |
| I-g | furilazole |
| I-g | fenclorim |
| I-g | cumyluron |
| I-g | daimuron/dymron |
| I-g | dimepiperate |
| I-g | IIe-5 |
| I-g | IIe-11 |

Surprisingly, it has now been found that the active compound combinations defined above of hetaryl-substituted pyrazolidinedione derivatives of the general formula (I) and safeners (antidotes) from the group (b') listed above, while having very good compatibility with useful plants, have a particularly high herbicidal activity and can be used in various crops in particular in cereals (especially wheat), but also in soybeans, potatoes, corn and rice, for the selective control of weeds.

Here, it has to be considered surprising that, from a large number of known safeners or antidotes capable of antagonizing the damaging effect of a herbicide on the crop plants it is in particular the compounds of group (b') listed above which are suitable for compensating the damaging effect of hetaryl-substituted pyrazolidinedione derivatives on the crop plants almost completely, without negatively affecting the herbicidal activity against the weeds to any considerable extent.

Emphasis may be given here to the particularly advantageous effect of the particularly preferred and most preferred combination partners made from group (b'), in particular with respect to sparing cereal plants, such as, for example, wheat, barley and rye, but also corn and rice, as crop plants.

Using, for example, according to process (A-α) hexahydropyridazine and (chlorocarbonyl)-2-[4-(2-(4-chlorophenyl)-5-methyl)thiazolyl]ketene as starting materials, the course of the reaction of the process can be represented by the reaction scheme below:

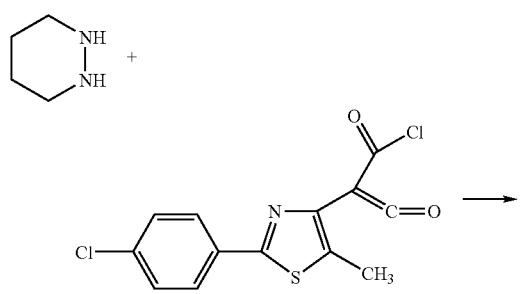

Using, for example, according to process (A-β) hexahydropyridazine and dimethyl 4-[2-(4-chlorophenyl)-5-methyl]thiazolylmalonate as starting materials, the course of the process according to the invention can be represented by the reaction scheme below:

Using, for example, according to process A (γ) 1-ethoxycarbonyl-2-[1-(3-(4-chlorophenyl)-5-methyl)pyrazolylmethyl]hexahydropyridazine as starting material, the course of the process according to the invention can be represented by the reaction scheme below:

Using, for example, according to process (Bα) 4-[4-(5-methyl-2-(3-chlorophenyl)thiazolyl]1,2-dimethylpyrazolidine-3,5-dione and pivaloyl chloride as starting materials, the course of the process according to the invention can be represented by the reaction scheme below:

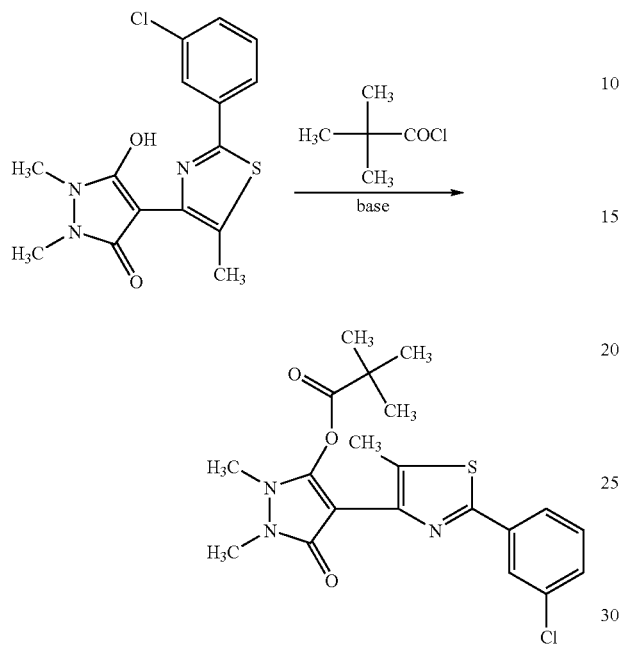

Using, for example, according to process (Bβ) 4-[4-(5-ethyl-2-(4-methoxyphenyl))thiazolyl]-1,2-tetramethylenepyrazolidine-3,5-dione and acetic anhydride as starting materials, the course of the process according to the invention can be represented by the reaction scheme below:

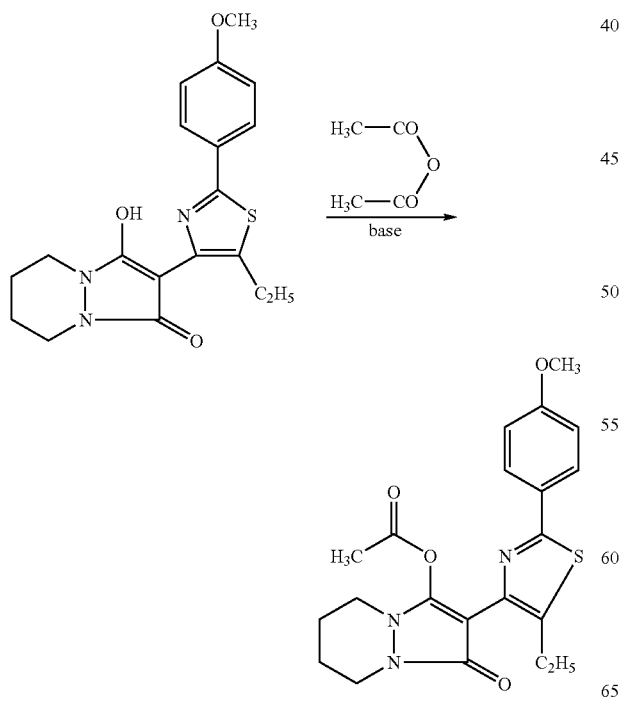

Using, for example, according to process (C) 4-[4-(5-methyl-2-(4-chlorophenyl))thiazolyl]-1,2-tetramethylenepyrazolidine-3,5-dione and ethoxy ethyl chloroformate as starting materials, the course of the process according to the invention can be represented by the reaction scheme below:

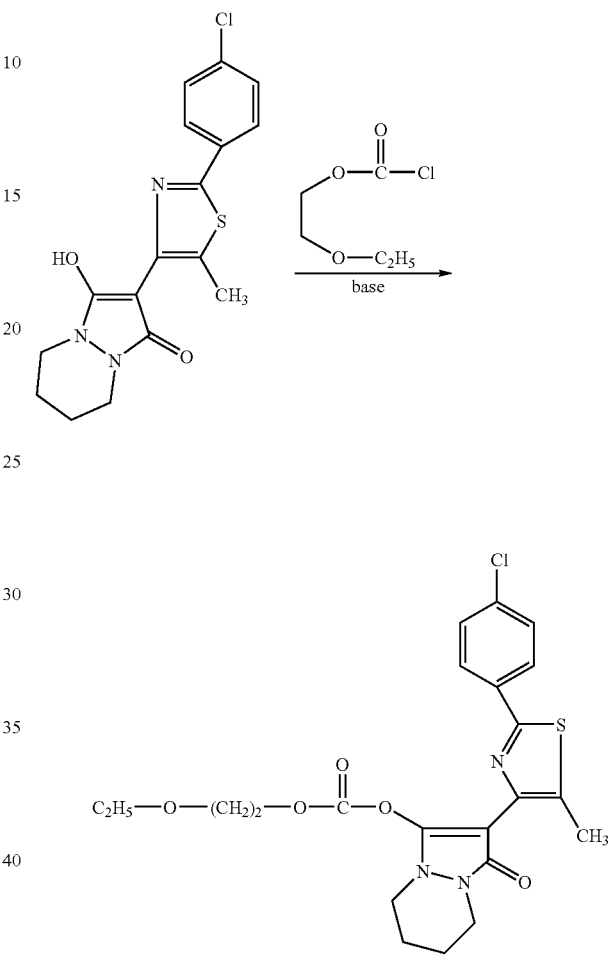

Using, for example, according to process (D), 4-[1-(5-methyl-3-(4-chlorophenyl))pyrazolyl]-1,2-dimethylpyrazolidine-3,5-dione and methyl chloromonothioformate as starting materials, the course of the reaction can be represented as follows:

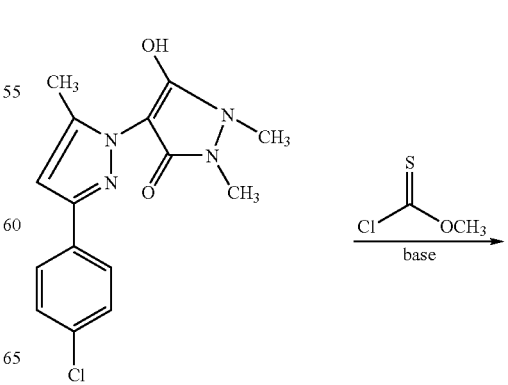

-continued

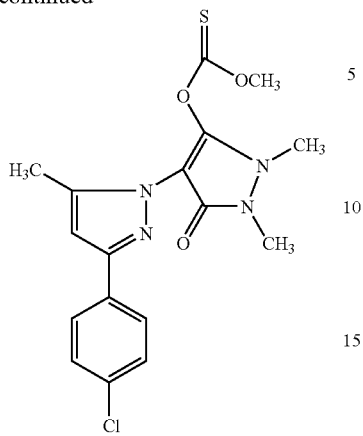

Using according to process (E) 4-[1-(5-methyl-3-(4-trifluoromethylphenyl))pyrazolyl]-1,2-penta-methylenepyrazolidine-3,5-dione and methanesulfonyl chloride as starting materials, the course of the reaction can be represented by the reaction scheme below:

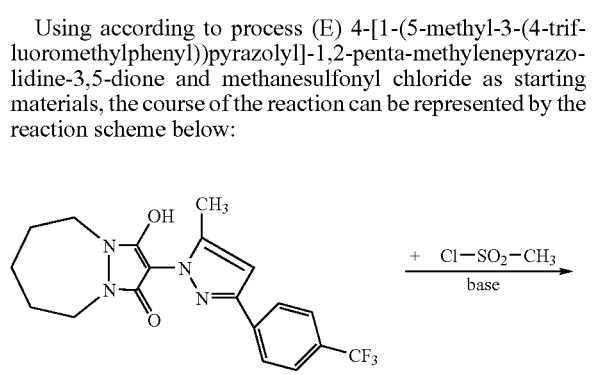

Using according to process (F) 4-[1-(5-methyl-3-(4-chlorophenyl))pyrazolyl]-1,2-tetramethylene-pyrazolidine-3,5-dione and 2,2,2-trifluoroethyl methanethiophosphonyl chloride as starting materials, the course of the reaction can be represented by the reaction scheme below:

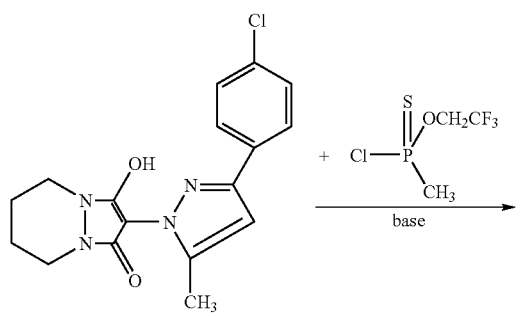

-continued

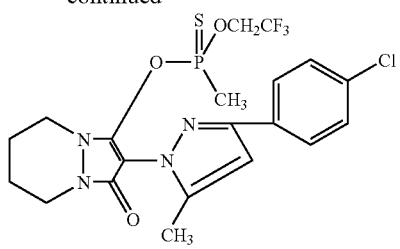

Using according to process (G) 4-[4-(5-methyl-2-(4-trifluoromethylphenyl))thiazolyl]-1,2-ethyloxamethylpyrazolidine-3,5-dione and NaOH as components, the course of the process according to the invention can be represented by the reaction scheme below:

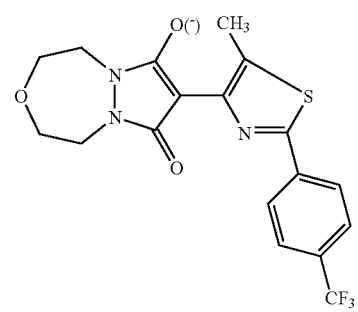

Using according to process (Hα) 4-[4-(5-methyl-2-(4-trifluoromethylphenyl))thiazolyl]-1,2-tetra-methylenepyrazolidine-3,5-dione and ethyl isocyanate as starting materials, the course of the reaction can be represented by the reaction scheme below:

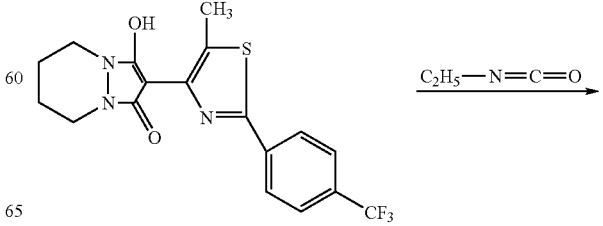

-continued

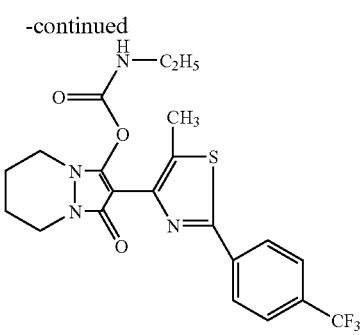

Using according to process (Hβ) 3-[4-(5-methyl-2-(4-chlorophenyl))thiazolyl]-1,2-dimethyl-pyrazolidine-3,5-dione and dimethylcarbamoyl chloride as starting materials, the course of the reaction can be represented by the scheme below:

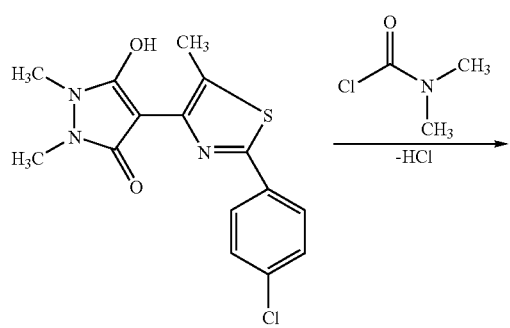

The halocarbonyl ketenes of the formula (III) required as starting materials in the above processes (A-α) are novel. They can be prepared in a simple manner by methods know in principle (cf., for example, Org. Prep. Proced. Int., 7, (4), 155-158, 1975, WO 96/35664, WO 97/02243, WO 97/36868 and DE 1 945 703). Thus, for example, the compounds of the formula (III)

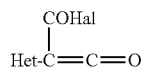
(III)

in which
Het is as defined above and
Hal represents chlorine or bromine, are obtained when
substituted phenylmalonic acids of the formula (IV-a)

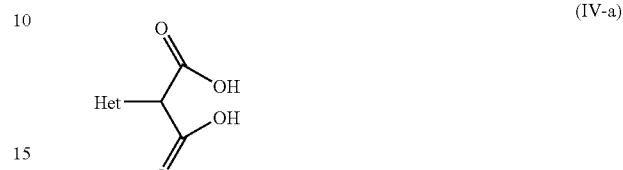
(IV-a)

in which
Het is as defined above are reacted with acid halides, such as, for example, thionyl chloride, phosphorus (V) chloride, phosphorus (III) chloride, oxalyl chloride, phosgene or thionyl bromide, if appropriate in the presence of catalysts, such as, for example, diethylformamide, methylsterylformamide or triphenylphosphine, and, if appropriate, in the presence of bases, such as, for example, pyridine or triethylamine.

The substituted phenylmalonic acids of the formula (IV-a) are novel. They can be prepared in a simple manner by known processes (cf., for example, Organikum, VEB Deutscher Verlag der Wissenschaften, Berlin 1977, p. 517 ff, EP-A-528 156, WO 96/35 664, WO 97/02 243, WO 97/01535, WO 97/36868 and WO 98/05638).

Thus, phenylmalonic acids of the formula (IV-a)

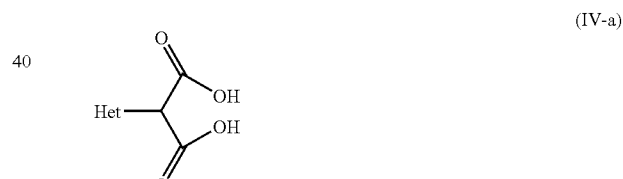
(IV-a)

in which
Het is as defined above are obtained when phenylmalonic esters of the formula (IV)

(IV)

in which
Het is as defined above,
U represents OR$^8$
and $R^8$ represents alkyl are initially hydrolyzed in the presence of a base and a solvent and then carefully acidified (EP-A-528 156, WO 96/35 664, WO 97/02 243).

The malonic esters of the formula (IV) where $U=OR^8$

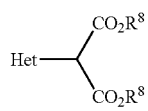
(IV)

in which
Het and $R^8$ are as defined above are novel, except for diethyl (1,3,5-trimethyl-1H-pyrazolyl) malonate and diethyl [1-(2.4-dinitrophenyl)-3,5-dimethyl-1H-pyrazol-4-yl]malonate (Alberola et. al., Anales de Quimica, Srie C: Quimica Organica y Bioquimica, 83, 55-61, 1987).

They can be prepared by generally known methods of organic chemistry (cf., for example, Tetrahedron Lett. 27, 2763 (1986), Organikum VEB Deutscher Verlag der Wissenschaften, Berlin 1977, p. 587 ff., WO 96/35664, WO 97/02243, WO 97/01535, WO 97/36868, WO 98/05638 and WO 99/47525) from hetarylacetic esters of the formula (XVI)

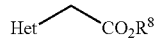
(XVI)

in which
Het and $R^8$ are as defined above.

Some of the hetaryl acid esters of the formula (XVI) are commercially available, some are known, or they can be prepared by processes known in principle
a) Thiazolylacetic esters: C. S. Rooney et al. J. Med. Chem. 26, 700-714 (1983); EP-A-368 592; M. S. Malamas et al. J. Med. Chem. 39, 237-246 (1996); J. L. Collins et al. J. Med. Chem. 41, 5037-5054 (1998); NL-A-66 14 130;
b) Oxazolylacetic esters: K. Meguro et al., Chem. Pharm. Bull, 34, 2840-2851 (1986), M. Sehi et al., Chem. Pharm. Bull. 36, 4435-4440 (1988), Malmas et al., J. Med. Chem. 39, 237-245 (1996), EP 0 177 353 A2, WO 87/03 807, WO 95/18 125, B. Hulin, J. Med. Chem. 35, 1853-1864 (1992), EP 0 389 699 A1.
c) The N-pyrazolylacetic esters of the formula (XVI) are known (DE-A 10 152 005). They can be prepared by processes known in principle (Nam, N. L. et. al, Chemistry of Heterocyclic Compounds 34, 382, (1998); L. K. Kulihova, L. V. Cherkesova, Khimiko-Farmateseyticheskii Zhurnal, 8, 18-21, (1974)).
d) Some of the C-pyrazolylacetic esters of the formula (XVI) are commercially available, some are known, or they can be prepared by processes known in principle (U.S. Pat. No. 4,146,721, JP-A-48 028 914, DE-A-1 946 370).

Some of the hydrazines, required as starting materials for the process (A-α) and (A-β) according to the invention, of the formula (II)

A-NH—NH-D (II)

in which
A and D are as defined above are commercially available, some are known from the literature cited at the outset, and/or they can be prepared by methods known from the literature (cf., for example, Liebigs Ann. Chem. 585, 6 (1954); Reaktionen der organischen Synthese, C. Ferri, page 212, 513; Georg Thieme Verlag Stuttgart, 1978; Liebigs Ann. Chem. 443, 242 (1925); Chem. Ber. 98, 2551 (1965), EP-A-508 126, WO 92/16510, WO 99/47 525, WO 01/17 972).

The compounds, required for the process (A-γ) according to the invention, of the formula (V)

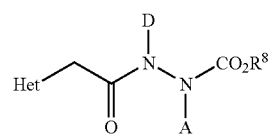
(V)

in which
A, D, Het and $R^8$ are as defined above are novel.

The hetaryl carbazates of the formula (V) are obtained, for example, when carbazates of the formula (XVII)

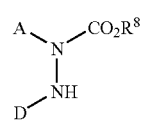
(XVII)

in which
A, $R^8$ and D are as defined above are reacted according to generally known methods of organic chemistry with substituted hetarylacetic acid derivatives of the formula (XVIII)

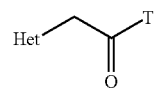
(XVIII)

in which
Het is as defined above and
T represents a leaving group introduced by reagents for activating carboxylic acids, such as carbonyldiimidazole, carbonyldiimides (such as, for example, dicyclohexylcarbondiimide), phosphorylating agents (such as, for example, $POCl_3$, BOP-Cl), halogenating agents, for example thionyl chloride, oxalyl chloride, phosgene or chloroformic esters, or represents $OR^8$ in which $R^8$ is as defined above.

Some of the compounds of the formula (XVIII) are novel. They can be prepared by processes known in principle and as is evident from the Preparation Examples (see, for example, Henecka, Houben-Weyl, Methoden der Organischen Chemie [Methods of Organic Chemistry], Vol. 8, pp. 467-469 (1952)).

The compounds of the formula (XVIII) are obtained, for example, by reacting substituted hetarylacetic acids of the formula (XIX)

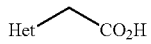

(XIX)

in which
Het is as defined above with halogenating agents (for example thionyl chloride, thionyl bromide, oxalyl chloride, phosgene, phosphorus trichloride, phosphorus tribromide or phosphorus pentachloride), phosphonylating agents, such as (for example, $POCl_3$, BOP-Cl), carbonyldiimidazole, carbonyldiimides (for example dicyclohexylcarbonyldiimide), if appropriate in the presence of a diluent (for example optionally chlorinated aliphatic or aromatic hydrocarbons, such as toluene or methylene chloride, or ethers, for example tetrahydrofuran, dioxane, methyl tert-butyl ether), at temperatures of from −20° C. to 150° C., preferably from −10° C. to 100° C.

Some of the hetarylacetic acids of the formula (XIX) are commercially available, some are known, or they can be prepared by processes known in principle which have also been mentioned for preparing the compounds of the formula (XVI).

Some of the carbazates of the formula (XVII) are commercially available compounds and some are known compounds, or they can be prepared by processes of organic chemistry known in principle.

The acyl halides of the formula (VI), carboxylic anhydrides of the formula (VII), chloroformic esters or chloroformic thioesters of the formula (VIII), chloromonothioformic esters or chlorodithioformic esters of the formula (IX), sulfonyl chlorides of the formula (X), phosphorus compounds of the formula (XI) and metal hydroxides, metal alkoxides or amines of the formulae (XII) and (XIII) and isocyanates of the formula (XIV) and carbamoyl chlorides of the formula (XV) furthermore required as starting materials for carrying out the processes (B), (C), (D), (E), (F), (G) and (H) according to the invention are generally known compounds of organic or inorganic chemistry.

Some of the compounds of the formulae (II), (XVI), (XVII) and (XIX) are commercially available, some are known, and/or they can be prepared by methods known in principle.

The process (A-α) according to the invention is characterized in that hydrazines of the formula (II) or salts of these compounds are reacted with ketene acid halides of the formula (III) in the presence of a diluent and, if appropriate, in the presence of an acid acceptor.

Suitable diluents for the process (A-α) according to the invention are all inert organic solvents. Preference is given to using optionally chlorinated hydrocarbons, such as, for example, mesitylene, chlorobenzene and dichlorobenzene, toluene, xylene, furthermore ethers, such as dibutyl ether, glycol dimethyl ether, diglycol dimethyl ether and diphenylethane, moreover polar solvents, such as dimethyl sulfoxide, sulfolane, dimethylformamide or N-methylpyrrolidone.

Suitable acid acceptors for carrying out the process variant (A-α) according to the invention are also customary acid acceptors.

Preference is given to using tertiary amines, such as triethylamine, pyridine, diazabicyclooctane (DABCO), diazabicycloundecane (DBU), diazabicyclononene (DBN), Hünig-Base and N,N-dimethylaniline.

When carrying out the process variant (A-α) according to the invention, the reaction temperatures can be varied within a relatively wide range. The process variant is expediently carried out at temperatures between 0° C. and 250° C., preferably between 50° C. and 220° C.

The process (A-α) according to the invention is expediently carried out under atmospheric pressure.

When carrying out the process (A-α) according to the invention, the reaction components of the formulae (II) and (III) in which A, D and Het are as defined above and Hal represents halogen and, if appropriate, the acid acceptors are generally employed in approximately equimolar amounts. However, it is also possible to use a relatively large excess (up to 5 mol) of one component or the other.

The process (A-β) is characterized in that hydrazines of the formula (II) or salts of this compound in which A and D are as defined above are subjected to a condensation with malonic acid derivatives of the formula (IV) in which Het and $R^8$ are as defined above, in the presence of a base.

Suitable diluents for the process (A-β) according to the invention are all inert organic solvents. Preference is given to using optionally halogenated hydrocarbons, such as toluene, xylene, mesitylene, chlorobenzene and dichlorobenzene, furthermore ethers, such as dibutyl ether, tetra-hydrofuran, dioxane, diphenyl ether, glycol dimethyl ether and diglycol dimethyl ether, moreover polar solvents, such as dimethyl sulfoxide, sulfolane, dimethylformamide, dimethylacetamide and N-methylpyrrolidone, and also alcohols, such as methanol, ethanol, propanol, isopropanol, butanol, isobutanol and tert-butanol.

Suitable bases (deprotonating agents) for carrying out the process (A-β) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be employed in the presence of phase transfer catalysts, such as, for example, triethylbenzylammonium chloride, tetrabutylammonium bromide, Adogen 464 (=methyltrialkyl($C_8$-$C_{10}$)ammonium chloride) or TDA 1 (=tris(methoxyethoxyethyl)amine). Alkali metals such as sodium or potassium can also be used. Furthermore, alkali metal and alkaline earth metal amides and hydrides, such as sodium amide, sodium hydride and calcium hydride, and additionally also alkali metal alkoxides, such as sodium methoxide, sodium ethoxide and potassium tert-butoxide can be employed.

It is also possible to use tertiary amines, such as triethylamine, pyridine, diazabicyclooctane (DABCO), diazabicycloundecane (DBU), diazabicyclononene (DBN), Hünig base and N,N-dimethylaniline.

When carrying out the process (A-β) according to the invention, the reaction temperatures can be varied within a relatively wide range. In general, the process is carried out at temperatures between 0° C. and 280° C., preferably between 50° C. and 180° C.

The process (A-β) according to the invention is generally carried out under atmospheric pressure.

When carrying out the process (A-β) according to the invention, the reaction components of the formulae (II) and (IV) are generally employed in approximately equimolar amounts. However, it is also possible to use a relatively large excess (up to 3 mol) of one component or the other.

The process (A-γ) is characterized in that compounds of the formula (V) in which A, D, Het and $R^8$ are as defined above are subjected to an intramolecular condensation in the presence of a base.

Suitable diluents for the process (A-γ) according to the invention are all inert organic solvents. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulfoxide, sulfolane, dimethylformamide and N-methylpyrrolidone, and also alcohols, such as methanol, ethanol, propanol, isopropanol, butanol, isobutanol and tert-butanol.

Suitable bases (deprotonating agents) for carrying out the process (A-γ) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be used in the presence of phase transfer catalysts, such as, for example, triethylbenzylammonium chloride, tetrabutylammonium bromide, Adogen 464 (=methyltrialkyl($C_8$-$C_{10}$)ammonium chloride) or TDA 1 (=tris(methoxyethoxyethyl)amine). It is furthermore possible to use alkali metals, such as sodium or potassium. Also suitable are alkali metal and alkaline earth metal amides and hydrides, such as sodium amide, sodium hydride and calcium hydride, and additionally also alkali metal alkoxides, such as sodium methoxide, sodium ethoxide and potassium tert-butoxide.

When carrying out the process (A-γ) according to the invention, the reaction temperatures can be varied within a relatively wide range. In general, the process is carried out at temperatures between 0° C. and 250° C., preferably between 50° C. and 150° C.

The process (A-γ) according to the invention is generally carried out under atmospheric pressure.

When carrying out the process (A-γ) according to the invention, the reaction components of the formula (V) and the deprotonating bases are generally employed in approximately doubly equimolar amounts. However, it is also possible to use a relatively large excess (up to 3 mol) of one component or the other.

The process (B-α) is characterized in that compounds of the formulae (I-1-a) to (I-4-a) are in each case reacted with carbonyl halides of the formula (VI), if appropriate in the presence of a diluent and if appropriate in the presence of an acid binder.

Suitable diluents for the process (B-α) according to the invention are all solvents which are inert to the acid halides. Preference is given to using hydrocarbons, such as benzine, benzene, toluene, xylene and tetralin, furthermore halogenated hydrocarbons, such as methylene chloride, chloroform, carbon tetrachloride, chlorobenzene and o-dichlorobenzene, moreover ketones, such as acetone and methylisopropyl ketone, furthermore ethers, such as diethyl ether, tetrahydrofuran and dioxane, additionally carboxylic esters, such as ethyl acetate, nitrites, such as acetonitrile, and also strongly polar solvents, such as dimethylformamide, dimethylacetamide, dimethyl sulfoxides and sulfolane. The hydrolytic stability of the acid halide permitting, the reaction can also be carried out in the presence of water.

Suitable acid binders for the reaction according to the process (B-α) according to the invention are all customary acid acceptors. Preference is given to using tertiary amines, such as triethylamine, pyridine, diazabicyclooctane (DABCO), diazabicycloundecene (DBU), diazabicyclononene (DBN), Hünig base and N,N-dimethylaniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

In the process (B-α) according to the invention, the reaction temperatures can be varied within a relatively wide range. In general, the process is carried out at temperatures between −20° C. and +150° C., preferably between 0° C. and 100° C.

When carrying out the process (B-α) according to the invention, the starting materials of the formulae (I-1-a) to (I-4-a) and the carbonyl halide of the formula (VI) are generally each employed in approximately equivalent amounts. However, it is also possible to use a relatively large excess (up to 5 mol) of the carbonyl halide. Work-up is carried out by customary methods.

The process (B-α) is characterized in that compounds of the formulae (I-1-a) to (I-4-a) are reacted with carboxylic anhydrides of the formula (VII), if appropriate in the presence of a diluent and if appropriate in the presence of an acid binder.

Suitable diluents for the process (B-β) according to the invention are preferably those diluents which are also preferably used when using acid halides. Furthermore, excess carboxylic anhydride may simultaneously act as diluent.

The acid binders which are added, if appropriate, in the process (B-β) are preferably those acid binders which are also preferred when using acid halides.

The reaction temperatures in the process (B-β) according to the invention may be varied within a relatively wide range. In general, the process is carried out at temperatures between −20° C. and +150° C., preferably between 0° C. and 100° C.

When carrying out the process (B-β) according to the invention, the starting materials of the formulae (I-1-a) to (I-4-a) and the carboxylic anhydride of the formula (VII) are generally each employed in approximately equivalent amounts. However, it is also possible to use a relatively large excess (up to 5 mol) of the carboxylic anhydride. Work-up is carried out by customary methods.

In general, diluents and excess carboxylic anhydride and the carboxylic acid formed are removed by distillation or by washing with an organic solvent or with water.

The process (C) is characterized in that compounds of the formulae (I-1-a) to (I-4-a) are in each case reacted with chloroformic esters or chloroformic thiolesters of the formula (VIII), if appropriate in the presence of a diluent and if appropriate in the presence of an acid binder.

Suitable acid binders for the process (C) according to the invention are all customary acid acceptors. Preference is given to using tertiary amines, such as triethylamine, pyridine, DABCO, DBU, DBA, Hünig base and N,N-dimethylaniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

Suitable diluents for the process (C) according to the invention are all solvents which are inert toward the chloroformic esters or chloroformic thiolesters. Preference is given to using hydrocarbons, such as benzine, benzene, toluene, xylene and tetralin, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, nitriles, such as acetonitrile, and also strongly polar solvents, such as dimethylformamide, dimethylacetamide, dimethyl sulfoxide and sulfolane.

When carrying out the process (C) according to the invention, the reaction temperatures can be varied within a relatively wide range. If the process is carried out in the presence of a diluent and an acid binder, the reaction temperatures are generally between −20° C. and +100° C., preferably between 0° C. and 50° C.

The process (C) according to the invention is generally carried out under atmospheric pressure.

When carrying out the process (C) according to the invention, the starting materials of the formulae (I-1-a) to (I-4-a) and the appropriate chloroformic ester or chloroformic thiolester of the formula (VIII) are generally each employed in approximately equivalent amounts. However, it is also possible to use a relatively large excess (up to 2 mol) of one component or the other. Work-up is carried out by customary methods. In general, precipitated salts are removed and the reaction mixture which remains is concentrated by removing the diluent under reduced pressure.

The process (D) according to the invention is characterized in that compounds of the formulae (I-1-a) to (I-4-a) are in each case reacted with compounds of the formula (IX) in the presence of a diluent and, if appropriate, in the presence of an acid binder.

In preparation process (D), about 1 mol of chloromonothioformic ester or chlorodithioformic ester of the formula (IX) is reacted per mole of starting material of the formulae (I-1-a) to (I-4-a), at from 0 to 120° C., preferably from 20 to 60° C.

Suitable diluents, which are added, if appropriate, are all inert polar organic solvents, such as nitriles, esters, ethers, amides, sulfones, sulfoxides, but also halogenated alkanes.

Preference is given to using acetonitrile, ethyl acetate, dimethyl sulfoxide, tetrahydrofuran, dimethylformamide or methylene chloride.

If, in a preferred embodiment, the enolate salt of the compounds (I-1-a) to (I-4-a) is prepared by adding strong deprotonating agents, such as, for example, sodium hydride or potassium tert-butoxide, the further addition of acid binders may be dispensed with.

If acid binders are used, these are customary inorganic or organic bases, for example sodium hydroxide, sodium carbonate, potassium carbonate, pyridine, triethylamine.

The reaction can be carried out at atmospheric pressure or under elevated pressure and is preferably carried out at atmospheric pressure. Work-up is carried out by customary methods.

The process (E) according to the invention is characterized in that compounds of the formulae (I-1-a) to (I-4-a) are in each case reacted with sulfonyl chlorides of the formula (X), if appropriate in the presence of a diluent and if appropriate in the presence of an acid binder.

In the preparation process (E), about 1 mol of sulfonyl chloride of the formula (X) is reacted per mole of starting material of the formulae (I-1-a) to (I-4-a), at from −20 to 150° C., preferably from 20 to 70° C.

Suitable diluents, which are added, if appropriate, are all inert polar organic solvents, such as nitriles, esters, ethers, amides, sulfones, sulfoxides or halogenated hydrocarbons, such as methylene chloride.

Preference is given to using acetonitrile, ethyl acetate, dimethyl sulfoxide, tetrahydrofuran, dimethylformamide, methylene chloride.

If, in a preferred embodiment, the enolate salt of the compounds (I-1-a) to (I-4-a) is prepared by adding strong deprotonating agents (such as, for example, sodium hydride or potassium tert-butoxide), the further addition of acid binders may be dispensed with.

If acid binders are used, these are customary inorganic or organic bases, for example sodium hydroxide, sodium carbonate, potassium carbonate, pyridine, triethylamine.

The reaction can be carried out at atmospheric pressure or under elevated pressure and is preferably carried out at atmospheric pressure. Work-up is carried out by customary methods.

The process (F) according to the invention is characterized in that compounds of the formulae (I-1-a) to (I-4-a) are in each case reacted with phosphorus compounds of the formula (XI), if appropriate in the presence of a diluent and if appropriate in the presence of an acid binder.

In preparation process (F), to obtain compounds of the formulae (I-1-e) to (I-4-e), 1 to 2, preferably 1 to 1.3, mol of the phosphorus compound of the formula (XI) are reacted per mole of the compounds (I-1-a) to (I-4-a), at temperatures between −40° C. and 150° C., preferably between −10 and 110° C.

Suitable diluents, which are added, if appropriate, are all inert polar organic solvents, such as ethers, amides, nitriles, alcohols, sulfides, sulfones, sulfoxides, etc.

Preference is given to using acetonitrile, dimethyl sulfoxide, tetrahydrofuran, dimethylformamide, methylene chloride.

Suitable acid binders, which are added, if appropriate, are customary inorganic or organic bases, such as hydroxides, carbonates or amines. Sodium hydroxide, sodium carbonate, potassium carbonate, pyridine, triethylamine may be mentioned by way of example.

The reaction can be carried out at atmospheric pressure or under elevated pressure and is preferably carried out at atmospheric pressure. Work-up is carried out by customary methods of organic chemistry. The end products obtained are preferably purified by crystallization, chromatographic purification or by "incipient distillation", i.e. removal of the volatile components under reduced pressure.

The process (G) is characterized in that compounds of the formulae (I-1-a) to (I-4-a) are reacted with metal hydroxides or metal alkoxides of the formula (XII) or amines of the formula (XIII), if appropriate in the presence of a diluent.

Suitable diluents for the process (G) according to the invention are, preferably, ethers, such as tetrahydrofuran, dioxane, diethyl ether, or else alcohols, such as methanol, ethanol, isopropanol, and also water.

The process (G) according to the invention is generally carried out under atmospheric pressure.

The reaction temperatures are generally between −20° C. and 100° C., preferably between 0° C. and 50° C.

The process (H) according to the invention is characterized in that compounds of the formulae (I-1-a) to (I-4-a) are in each case (H-α) reacted with compounds of the formula (XIV), if appropriate in the presence of a diluent and if appropriate in the presence of a catalyst, or (H-β) with compounds of the formula (XV), if appropriate in the presence of a diluent and if appropriate in the presence of an acid binder.

In preparation process (H-α), about 1 mol of isocyanate of the formula (XIV) are reacted per mole of starting material of the formulae (I-1-a) to (I-4-a), at from 0 to 100° C., preferably at from 20 to 50° C.

Suitable diluents, which are added, if appropriate, are all inert organic solvents, such as ethers, amides, nitriles, sulfones, sulfoxides.

If appropriate, catalysts may be added to accelerate the reaction. Suitable for use as catalysts are, very advantageously, organic tin compounds, such as, for example, dibutyltin dilaurate. The reaction is preferably carried out at atmospheric pressure.

In preparation process (H-β), about 1 mol of carbamoyl chloride of the formula (XV) is reacted per mole of starting material of the formulae (I-1-a) to (I-4-a), at from −20 to 150° C., preferably at from 0 to 70° C.

Suitable diluents, which are added, if appropriate, are all inert polar organic solvents, such as nitriles, esters, ethers, amides, sulfones, sulfoxides or halogenated hydrocarbons.

Preference is given to using acetonitrile, ethyl acetate, dimethyl sulfoxide, tetrahydrofuran, dimethylformamide or methylene chloride.

If, in a preferred embodiment, the enolate salt of the compound (I-1-a) to (I-4-a) is prepared by adding strong deprotonating agents (such as, for example, sodium hydride or potassium tert-butoxide), the further addition of acid binders may be dispensed with.

If acid binders are used, these are customary inorganic or organic bases, for example sodium hydroxide, sodium carbonate, potassium carbonate, triethylamine or pyridine.

The reaction can be carried out at atmospheric pressure or under elevated pressure and is preferably carried out at atmospheric pressure. Work-up is carried out by customary methods.

The active compounds are suitable for protecting plants and plant organs, for increasing the harvest yields, for improving the quality of the harvested material and for controlling animal pests, in particular insects, arachnids and nematodes, which are encountered in agriculture, in forests, in gardens and leisure facilities, in the protection of stored products and of materials, and in the hygiene sector, and have good plant tolerance and favorable toxicity to warm-blooded animals and are tolerated well by the environment. They may be preferably employed as plant protection agents. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera* spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Acheta domesticus, Gryllotalpa* spp., *Locusta migratoria migratorioides, Melanoplus* spp. and *Schistocerca gregaria.*

From the order of the Blattaria, for example, *Blatta orientalis, Periplaneta americana, Leucophaea maderae, Blattella germanica.*

From the order of the Dermaptera, for example, *Forficula auricularia.*

From the order of the Isoptera, for example, *Reticulitermes* spp.

From the order of the Phthiraptera, for example, *Pediculus humanus corporis, Haematopinus* spp., *Linognathus* spp., *Trichodectes* spp. and *Damalinia* spp.

From the order of the Thysanoptera, for example, *Hercinothrips femoralis, Thrips tabaci, Thrips palmi* and *Frankliniella accidentalis.*

From the order of the Heteroptera, for example, *Eurygaster* spp., *Dysdercus intermedius, Piesma quadrata, Cimex lectularius, Rhodnius prolixus, Triatoma* spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhiopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.

From the order of the Lepidoptera, for example, *Pectinophora gossypiella, Bupalus piniarius, Chematobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusia* ni, *Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus* spp. and *Oulema oryzae.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica* and *Lissorhoptrus oryzophilus.*

From the order of the Hymenoptera, for example, *Diprion* spp., *Hoplocampa* spp., *Lasius* spp., *Monomorium pharaonis* and *Vespa* spp.

From the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp. and *Liriomyza* spp.

From the order of the Siphonaptera, for example, *Xenopsylla cheopis* and *Ceratophyllus* spp.

From the class of the Arachnida, for example, *Scorpio maurus, Latrodectus mactans, Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp. and *Brevipalpus* spp.

The phytoparasitic nematodes include, for example, *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp. and *Bursaphelenchus* spp.

If appropriate, the compounds according to the invention can, at certain concentrations or application rates, also be used as herbicides or microbicides, for example as fungicides, antimycotics and bactericides. If appropriate, they can also be employed as intermediates or precursors for the synthesis of other active compounds.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds.

Treatment according to the invention of the plants and plant parts with the active compounds is carried out directly or by allowing the compounds to act on the surroundings, environment or storage space by the customary treatment methods, for example by immersion, spraying, evaporation, fogging, scattering, painting on, injecting and, in the case of propagation material, in particular in the case of seeds, also by applying one or more coats.

The active compounds can be converted to the customary formulations, such as solutions, emulsions, wettable powders, suspensions, powders, dusts, pastes, soluble powders, granules, suspension-emulsion concentrates, natural and synthetic materials impregnated with active compound and microencapsulations in polymeric substances.

These formulations are produced in a known manner, for example by mixing the active compounds with extenders, that is liquid solvents, and/or solid carriers, optionally with the use of surfactants, that is emulsifiers and/or dispersants, and/or foam-formers.

If the extender used is water, it is also possible to employ for example organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethylformamide and dimethyl sulfoxide, and also water.

As solid carriers there are suitable:

for example ammonium salts and ground natural minerals such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; as emulsifiers and/or foam-formers there are suitable: for example nonionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates and also protein hydrolysates; as dispersants there are suitable: for example lignosulfite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95% by weight of active compound, preferably between 0.5 and 90%.

The active compound according to the invention can also be used as such or in its formulations as a mixture with known fungicides, bactericides, acaricides, nematicides or insecticides in order to broaden the spectrum of activity for example or prevent the development of resistance. Thus, in many cases, synergistic effects are obtained, i.e. the effectiveness of the mixture is greater than the effectiveness of the individual components.

Particularly favorable mixing components are, for example, the following compounds:

Fungicides:

2-phenylphenol; 8-hydroxyquinoline sulfate; acibenzolar-5-methyl; aldimorph; amidoflumet; ampropylfos; ampropylfos-potassium; andoprim; anilazine; azaconazole; azoxystrobin; benalaxyl; benodanil; benomyl; benthiavalicarb-isopropyl; benzamacril; benzamacril-isobutyl; bilanafos; binapacryl; biphenyl; bitertanol; blasticidin-S; bromuconazole; bupirimate; buthiobate; butylamine; calcium polysulphide; capsimycin; captafol; captan; carbendazim; carboxin; carpropamid; carvone; chinomethionat; chlobenthiazone; chlorfenazole; chloroneb; chlorothalonil; chlozolinate; clozylacon; cyazofamid; cyflufenamid; cymoxanil; cyproconazole; cyprodinil; cyprofuram; Dagger G; debacarb; dichlofluanid; dichlone; dichlorophen; diclocymet; diclomezine; dicloran; diethofencarb; difenoconazole; diflumetorim; dimethirimol; dimethomorph; dimoxystrobin; diniconazole; diniconazole-M; dinocap; diphenylamine; dipyrithione; ditalimfos; dithianon; dodine; drazoxolon; edifenphos; epoxiconazole; ethaboxam; ethirimol; etridiazole; famoxadone; fenamidone; fenapanil; fenarimol; fenbuconazole; fenfuram; fenhexamid; fenitropan; fenoxanil; fenpiclonil; fenpropidin; fenpropimorph; ferbam; fluazinam; flubenzimine; fludioxonil; flumetover; flumorph; fluoromide; fluoxastrobin; fluquinconazole; flurprimidol; flusilazole; flusulfamide; flutolanil; flutriafol; folpet; fosetyl-Al; fosetyl-sodium; fuberidazole; furalaxyl; furametpyr; furcarbanil; furmecyclox; guazatine; hexachlorobenzene; hexaconazole; hymexazole; imazalil; imibenconazole; iminoctadine triacetate; iminoctadine tris(albesilate); iodocarb; ipconazole; iprobenfos; iprodione; iprovalicarb; irumamycin; isoprothiolane; isovaledione; kasugamycin; kresoxim-methyl; mancozeb; maneb; meferimzone; mepanipyrim; mepronil; metalaxyl; metalaxyl-M; metconazole; methasulfocarb; methfuroxam; metiram; metominostrobin; metsulfovax; mildiomycin; myclobutanil; myclozolin; natamycin; nicobifen; nitrothal-isopropyl; noviflumuron; nuarimol; ofurace; orysastrobin; oxadixyl; oxolinic acid; oxpoconazole; oxycarboxin; oxyfenthiin; paclobutrazole; pefurazoate; penconazole; pencycuron; phosdiphen; phthalide; picoxystrobin; piperalin; polyoxins; polyoxorim; probenazole; prochloraz; procymidone; propamocarb; propanosine-sodium; propiconazole; propineb; proquinazid; prothioconazole; pyraclostrobin; pyrazophos; pyrifenox; pyrimethanil; pyroquilon; pyroxyfur; pyrrolenitrine; quinconazole; quinoxyfen; quintozene; simeconazole; spiroxamine; sulfur; tebuconazole; tecloftalam; tecnazene; tetcyclacis; tetraconazole; thiabendazole; thicyofen; thifluzamide; thiophanate-methyl; thiram; tioxymid; tolclofos-methyl; tolylfluanid; triadimefon; triadimenol; triazbutil; triazoxide; tricyclamide; tricyclazole; tridemorph; trifloxystrobin; triflumizole; triforine; triticonazole; uniconazole; validamycin A; vinclozolin; zineb; ziram; zoxamide; (2S)-N-[2-[4-[[3-(4-chlorophenyl)-2-propynyl]oxy]-3-methoxyphenyl]ethyl]-3-methyl-2-[(methylsulphonyl)amino]butanemide; 1-(1-naphthalenyl)-1H-pyrrole-2,5-dione; 2,3,5,6-tetrachloro-4-(methylsulfonyl)pyridine; 2-amino-4-methyl-N-phenyl-5-thiazolecarboxamide; 2-chloro-N-(2,3-dihydro-1,1,3-trimethyl-1H-inden-4-yl)-3-pyridinecarboxamide; 3,4,5-trichloro-2,6-pyridinedicarbonitrile; actinovate; cis-1-(4-chlorophenyl)-2-(1H-1,2,4-triazol-1-yl)cycloheptanol; methyl 1-(2,3-dihydro-2,2-dimethyl-1H-inden-1-yl)-1H-imidazole-5-carboxylate; monopotassium carbonate; N-(6-methoxy-3-pyridinyl)cyclopropanecarboxamide; N-butyl-8-(1,1-dimethylethyl)-1-oxaspiro[4.5]decane-3-amine; sodium tetrathiocarbonate;

and copper salts and preparations, such as Bordeaux mixture; copper hydroxide; copper naphthenate; copper oxychloride; copper sulfate; cufraneb; copper oxide; mancopper; oxine-copper.

Bactericides:

bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulfate and other copper preparations.

Insecticides/Acaricides/Nematicides:

abamectin, ABG-9008, acephate, acequinocyl, acetamiprid, acetoprole, acrinathrin, AKD-1022, AKD-3059, AKD-3088, alanycarb, aldicarb, aldoxycarb, allethrin, alpha-cypermethrin (alpha-methrin), amidoflumet, aminocarb, amitraz, avermectin, AZ-60541, azadirachtin, azamethiphos, azinphos-methyl, azinphos-ethyl, azocyclotin,

*Bacillus popilliae, Bacillus sphaericus, Bacillus subtilis, Bacillus thuringiensis, Bacillus thuringiensis* strain EG-2348, *Bacillus thuringiensis* strain GC-91, *Bacillus thuringiensis* strain NCTC-11821, baculoviruses, *Beauveria bassiana, Beauveria tenella*, benclothiaz, bendiocarb, benfuracarb, bensultap benzoximate, beta-cyfluthrin, beta-cypermethrin, bifenazate, bifenthrin, binapacryl, bioallethrin, bioallethrin-5-cyclopentyl-isomer, bioethanomethrin, biopermethrin, bioresmethrin, bistrifluron, BPMC, brofenprox, bromophos-ethyl, bromopropylate, bromfenvinfos (-methyl), BTG-504, BTG-505, bufencarb, buprofezin, butathiofos, butocarboxim, butoxycarboxim, butylpyridaben, cadusafos, camphechlor, carbaryl, carbofuran, carbophenothion, carbosulfan, cartap, CGA-50439, chinomethionat, chlordane, chlordimeform, chloethocarb, chlorethoxyfos, chlorfenapyr, chilorfenvinphos, chlorfluazuron, chlormephos, chlorobenzilate, chloropicrin, chliorproxyfen, chlorpyrifos-methyl, chlorpyrifos (-ethyl), chlovaporthrin, chromafenozide, cis-cypermethrin, cis-resmethrin, cis-permethrin, clocythrin, cloethocarb, clofentezine, clothianidin, clothiazoben, codlemone, coumaphos, cyanofenphos, cyanophos, cycloprene, cycloprothrin, *Cydia pomonella, cyfluthrin, cyhalothrin, cyhexatin, cypermethrin, cyphenothrin* (1R-trans-isomer), cyromazine, DDT, deltamethrin, demeton-5-methyl, demeton-5-methylsulfone, diafenthiuron, dialifos, diazinon, dichlofenthion, dichlorvos, dicofol, dicrotophos, dicyclanil, diflubenzuron, dimefluthrin, dimethoate, dimethylvinphos, dinobuton, dinocap, dinotefuran, diofenolan, disulfoton, docusatsodium, dofenapyn, DOWCO-439, eflusilanate, emamectin, emamectin-benzoate, empenthrin (1R-isomer), endosulfan, *Entomopthora* spp., EPN, esfenvalerate, ethiofencarb, ethiprole, ethion, ethoprophos, etofenprox, etoxazole, etrimfos, famphur, fenamiphos, fenazaquin, fenbutatin oxide, fenfluthrin, fenitrothion, fenobucarb, fenothiocarb, fenoxacrim, fenoxycarb, fenpropathrin, fenpyrad, fenpyrithrin, fenpyroximate, fensulfothion, fenthion, fentrifanil, fenvalerate, fipronil, flonicamid, fluacrypyrim, fluazuron, flubenzimine, flubrocythrinate, flucycloxuron, flucythrinate, flufenerim, flufenoxuron, flufenprox, flumethrin, flupyrazofos, flutenzin (flufenzine), fluvalinate, fonofos, formetanate, formothion, fosmethilan, fosthiazate, fubfenprox (fluproxyfen), furathiocarb, gamma-cyhalothrin, gamma-HCH, gossyplure, grandlure, granulosis viruses, halfenprox, halofenozide, HCH, HCN-801, heptenophos, hexaflumuron, hexythiazox, hydramethylnone, hydroprene, IKA-2002, imidacloprid, imiprothrin, indoxacarb, iodofenphos, iprobenfos, isazofos, isofenphos, isoprocarb, isoxathion, ivermectin, japonilure, kadethrin, nuclear polyhedrosis viruses, kinoprene, lambda-cyhalothrin, lindane, lufenuron, malathion, mecarbam, mesulfenfos, metaldehyde, metamsodium, methacrifos, methamidophos, *Metharhizium anisopliae, Metharhizium flavoviride*, methidathion, methiocarb, methomyl, methoprene, methoxychlor, methoxyfenozide, metofluthrin, metolcarb, metoxadiazone, mevinphos, milbemectin, milbemycin, MKI-245, MON-45700, monocrotophos, moxidectin, MTI-800, naled, NC-104, NC-170, NC-184, NC-194, NC-196, niclosamide, nicotine, nitenpyram, nithiazine, NNI-0001, NNI-01011, NNI-0250, NNI-9768, novaluron, noviflumuron, OK-5101, OK-5201, OK-9601, OK-9602, OK-9701, OK-9802, omethoate, oxamyl, oxydemeton-methyl,

*Paecilomyces fumosoroseus*, parathion-methyl, parathion (-ethyl), permethrin (cis-, trans-), petroleum, PH-6045, phenothrin (1R-trans isomer), phenthoate, phorate, phosalone, phosmet, phosphamidon, phosphocarb, phoxim, piperonyl butoxide, pirimicarb, pirimiphos-methyl, pirimiphos-ethyl, potassium oleate, prallethrin, profenofos, profluthrin, promecarb, propaphos, propargite, propetamphos, propoxur, prothiofos, prothoate, protrifenbute, pymetrozine, pyraclofos, pyresmethrin, pyrethrum, pyridaben, pyridalyl, pyridaphenthion, pyridathion, pyrimidifen, pyriproxyfen, quinalphos, resmethrin, RH-5849, ribavirin, RU-12457, RU-15525, S-421, S-1833, salithion, sebufos, SI-0009, silafluofen, spinosad, spirodiclofen, spiromesifen, sulfluramid, sulfotep, sulprofos, SZI-121, tau-fluvalinate, tebufenozide, tebufenpyrad, tebupirimfos, teflubenzuron, tefluthrin, temephos, temivinphos, terbam, terbufos, tetrachlorvinphos, tetradifon, tetramethrin, tetramethrin (1R-isomer), tetrasul, theta-cypermethrin, thiacloprid, thiamethoxam, thiapronil, thiatriphos, thiocyclam hydrogenoxalate, thiodicarb, thiofanox, thiometon, thiosultap-sodium, thuringiensin, tolfenpyrad, tralocythrin, tralomethrin, transfluthrin, triarathene, triazamate, triazophos, triazuron, trichlophenidine, trichlorfon, *Trichoderma atroviride*, triflumuron, trimethacarb, vamidothion, vaniliprole, verbutin, *Verticillium lecanii*, WL-108477, WL-40027,

YI-5201, YI-5301, YI-5302,

XMC, xylylcarb,

ZA-3274, zeta-cypermethrin, zolaprofos, ZXI-8901, the compound 3-methylphenyl propylcarbamate (tsumacide Z), the compound 3-(5-chloro-3-pyridinyl)-8-(2,2,2-trifluoroethyl)-8-azabicyclo[3.2.1]octane-3-carbonitrile (CAS-Reg. No. 185982-80-3) and the corresponding 3-endo-isomer (CAS-Reg. No. 185984-60-5) (cf. WO-96/37494, WO-98/25923), and preparations which comprise insecticidally active plant extracts, nematodes, fungi or viruses.

A mixture with other known active compounds, such as herbicides, fertilizers, growth regulators, safeners and/or semiochemicals is also possible.

When used as insecticides, the active compounds according to the invention can furthermore be present in their commercially available formulations and in the use forms, prepared from these formulations, as a mixture with synergistic agents. Synergistic agents are compounds, which increase the action of the active compounds, without it being necessary for the synergistic agent added to be active itself.

When used as insecticides, the active compounds according to the invention can furthermore be present in their commercially available formulations and in the use forms, prepared from these formulations, as a mixture with inhibitors which reduce degradation of the active compound after use in the vicinity of the plant, on the surface of parts of plants or in plant tissues.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compound is distinguished by an excellent residual action on wood and clay as well as a good stability to alkali on limed substrates.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering, if appropriate in combination with conventional methods (Genetic Modified Organisms), and parts thereof are treated. The term "parts" or "parts of plants" or "plant parts" has been explained above.

Particularly preferably, plants of the plant cultivars which are in each case commercially available or in use are treated according to the invention. Plant cultivars are to be understood as meaning plants having certain properties ("traits") which have been obtained by conventional breeding by mutagenesis or by recombinant DNA techniques. These can be cultivars, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions to be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant cultivars (i.e. those obtained by genetic engineering) which are preferably to be treated according to the invention include all plants which, in the genetic modification, received genetic material which imparted particularly advantageous useful traits to these plants. Examples of such traits are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such traits are a better defense of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized are in particular increased defense of the plants against insects, arachnids, nematodes and worms by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (hereinbelow referred to as "Bt plants"). Traits that are also particularly emphasized are the increased defense of the plants against fungi, bacteria and viruses by systemic acquired resistance (SAR), systemin, phytoalexius, elicitors and resistance genes and correspondingly expressed proteins and toxins. Traits that are furthermore particularly emphasized are the increased tolerance of the plants to certain herbicidally active compounds, for example imidazolinones, sulfonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plants will be developed and/or marketed in the future.

The plants listed can be treated according to the invention in a particularly advantageous manner with the compounds of the general formula I and/or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The active compounds according to the invention act not only against plant, hygiene and stored product pests, but also in the veterinary medicine sector against animal parasites (ectoparasites), such as hard ticks, soft-ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp. *Lutzomyia* spp., *Culicoides* spp., *Chrysops* spp., *Hybomitra* spp., *Atylotus* spp. *Tabanus* spp. *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example *Pulex* spp., *Ctenocephalides* spp., *Xenopsylla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example *Blatta orientalis*, *Periplaneta americana*, *Blattella germanica* and *Supella* spp.

From the subclass of the Acaria (Acarida) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

From the order of the Actinedida (Prostigmata) und Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of molded articles containing the active compound, such as collars, ear marks, tail marks, limb bands, halters, marking devices and the like.

When used for cattle, poultry, pets and the like, the active compounds of the formula (I) can be used as formulations (for example powders, emulsions, free-flowing compositions), which comprise the active compounds in an amount of 1 to 80% by weight, directly or after 100 to 10 000-fold dilution, or they can be used as a chemical bath.

It has furthermore been found that the compounds according to the invention also have a strong insecticidal action against insects which destroy industrial materials.

The following insects may be mentioned as examples and as preferred—but without a limitation:

Beetles, such as

*Hylotrupes bajulus*, *Chlorophorus pilosis*, *Anobium punctatum*, *Xestobium rufovillosum*, *Ptilinus pecticornis*, *Dendrobium pertinex*, *Ernobius mollis*, *Priobium carpini*, *Lyctus brunneus*, *Lyctus africanus*, *Lyctus planicollis*, *Lyctus linearis*, *Lyctus pubescens*, *Trogoxylon aequale*, *Minthes rugicollis*, *Xyleborus* spec., *Tryptodendron* spec., *Apate monachus*, *Bostrychus capucins*, *Heterobostrychus brunneus*, *Sinoxylon* spec., *Dinoderus minutus*;

Hymenopterons, such as

*Sirex juvencus*, *Urocerus gigas*, *Urocerus gigas taignus*, *Urocerus augur*;

Termites, such as

*Kalotermes flavicollis*, *Cryptotermes brevis*, *Heterotermes indicola*, *Reticulitermes flavipes*, *Reticulitermes santonensis*, *Reticulitermes lucifugus*, *Mastotermes darwiniensis*, *Zootermopsis nevadensis*, *Coptotermes formosanus*;

Bristletails, such as *Lepisma saccharina*.

Industrial materials in the present connection are to be understood as meaning non-living materials, such as, preferably, plastics, adhesives, sizes, papers and cards, leather, wood and processed wood products and coating compositions.

Wood and processed wood products are materials to be protected, especially preferably, from insect infestation.

Wood and processed wood products which can be protected by the agents according to the invention or mixtures comprising these are to be understood as meaning, for example:

building timber, wooden beams, railway sleepers, bridge components, boat jetties, wooden vehicles, boxes, pallets, containers, telegraph poles, wood paneling, wooden windows and doors, plywood, chipboard, joinery or wooden products which are used quite generally in house-building or in building joinery.

The active compounds can be used as such, in the form of concentrates or in generally customary formulations, such as powders, granules, solutions, suspensions, emulsions or pastes.

The formulations mentioned can be prepared in a manner known per se, for example by mixing the active compounds with at least one solvent or diluent, emulsifier, dispersing agent and/or binder or fixing agent, a water repellent, if appropriate siccatives and UV stabilizers and if appropriate dyestuffs and pigments, and also other processing auxiliaries.

The insecticidal compositions or concentrates used for the preservation of wood and wood-derived timber products comprise the active compound according to the invention in a concentration of 0.0001 to 95% by weight, in particular 0.001 to 60% by weight.

The amount of the compositions or concentrates employed depends on the nature and occurrence of the insects and on the medium. The optimum amount employed can be determined for the use in each case by a series of tests. In general, however, it is sufficient to employ 0.0001 to 20% by weight, preferably 0.001 to 10% by weight, of the active compound, based-on the material to be preserved.

Solvents and/or diluents which are used are an organic chemical solvent or solvent mixture and/or an oily or oil-like organic chemical solvent or solvent mixture of low volatility and/or a polar organic chemical solvent or solvent mixture and/or water, and if appropriate an emulsifier and/or wetting agent.

Organic chemical solvents which are preferably used are oily or oil-like solvents having an evaporation number above 35 and a flashpoint above 30° C., preferably above 45° C. Substances which are used as such oily or oil-like water-insoluble solvents of low volatility are appropriate mineral oils or aromatic fractions thereof, or solvent mixtures containing mineral oils, preferably white spirit, petroleum and/or alkylbenzene.

Mineral oils having a boiling range from 170 to 220° C., white spirit having a boiling range from 170 to 220° C., spindle oil having a boiling range from 250 to 350° C., petroleum and aromatics having a boiling range from 160 to 280° C., turpentine oil and the like, are advantageously employed.

In a preferred embodiment, liquid aliphatic hydrocarbons having a boiling range from 180 to 210° C. or high-boiling mixtures of aromatic and aliphatic hydrocarbons having a boiling range from 180 to 220° C. and/or spindle oil and/or monochloronaphthalene, preferably α-monochloronaphthalene, are used.

The organic oily or oil-like solvents of low volatility which have an evaporation number above 35 and a flashpoint above 30° C., preferably above 45° C., can be replaced in part by organic chemical solvents of high or medium volatility, provided that the solvent mixture likewise has an evaporation number above 35 and a flashpoint above 30° C. preferably above 45° C., and that the insecticide/fungicide mixture is soluble or emulsifiable in this solvent mixture.

According to a preferred embodiment, some of the organic chemical solvent or solvent mixture is replaced by an aliphatic polar organic chemical solvent or solvent mixture. Aliphatic organic chemical solvents containing hydroxyl and/or ester and/or ether groups, such as, for example, glycol ethers, esters or the like, are preferably used.

Organic chemical binders which are used in the context of the present invention are the synthetic resins and/or binding drying oils which are known per se, are water-dilutable and/or are soluble or dispersible or emulsifiable in the organic chemical solvents employed, in particular binders consisting of or comprising an acrylate resin, a vinyl resin, for example polyvinyl acetate, polyester resin, polycondensation or polyaddition resin, polyurethane resin, alkyd resin or modified alkyd resin, phenolic resin, hydrocarbon resin, such as indene-cumarone resin, silicone resin, drying vegetable oils and/or drying oils and/or physically drying binders based on a natural and/or synthetic resin.

The synthetic resin used as the binder can be employed in the form of an emulsion, dispersion or solution. Bitumen or bituminous substances can also be used as binders in an amount of up to 10% by weight. Dyestuffs, pigments, water-repelling agents, odor correctants and inhibitors or anticorrosive agents and the like which are known per se can additionally be employed.

It is preferred according to the invention for the composition or concentrate to comprise, as the organic chemical binder, at least one alkyd resin or modified alkyd resin and/or a drying vegetable oil. Alkyd resins having, an oil content of more than 45% by weight, preferably 50 to 68% by weight, are preferably used according to the invention.

All or some of the binder mentioned can be replaced by a fixing agent (mixture) or a plasticizer (mixture). These additives are intended to prevent evaporation of the active compounds and crystallization or precipitation. They preferably replace 0.01 to 30% of the binder (based on 100% of the binder employed).

The plasticizers originate from the chemical classes of phthalic acid esters, such as dibutyl, dioctyl or benzyl butyl phthalate, phosphoric acid esters, such as tributyl phosphate, adipic acid esters, such as di-(2-ethylhexyl)adipate, stearates, such as butyl stearate or amyl stearate, oleates, such as butyl, oleate, glycerol ethers or higher molecular weight glycol ethers, glycerol esters and p-toluenesulfonic acid esters.

Fixing agents are based chemically on polyvinyl alkyl ethers, such as, for example, polyvinyl methyl ether or ketones, such as benzophenone or ethylenebenzophenone.

Possible solvents or diluents are, in particular, also water, if appropriate as a mixture with one or more of the abovementioned organic chemical solvents or diluents, emulsifiers and dispersing gents.

Particularly effective preservation of wood is achieved by impregnation processes on a large industrial scale, for example vacuum, double vacuum or pressure processes.

The ready-to-use compositions can also comprise other insecticides, if appropriate, and also one or more fungicides, if appropriate.

Possible additional mixing partners are, preferably, the insecticides and fungicides mentioned in WO 94/29 268. The compounds mentioned in this document are an explicit constituent of the present application.

Especially preferred mixing partners which may be mentioned are insecticides, such as chlorpyriphos, phoxim, silafluofin, alphamethrin, cyfluthrin, cypermethrin, deltamethrin, permethrin, imidacloprid, NI-25, flufenoxuron, hexaflumuron, transfluthrin, thiacloprid, methoxyfeniozide, triflumuron, clothianidin, spinosad, tefluthrin, and also fungicides, such as epoxyconazole, hexaconazole, azaconazole, propiconazole, tebuconazole, cyproconazole, metconazole, imazalil, dichlorfluanid, tolylfluanid, 3-iodo-2-propinylbutyl carbamate, N-octyl-isothiazolin-3-one and 4,5-dichloro-N-octylisothiazolin-3-one.

The compounds according to the invention can at the same time be employed for protecting objects which come into contact with saltwater or brackish water, such as hulls, screens, nets, buildings, moorings and signalling systems, against fouling.

Fouling by sessile Oligochaeta, such as Serpulidae, and by shells and species from the Ledamorpha group (goose barnacles), such as various *Lepas* and *Scalpellum* species, or by species from the Balanomorpha group (acorn barnacles), such as *Balanus* or *Pollicipes* species, increases the frictional drag of ships and, as a consequence, leads to a marked increase in operational costs owing to higher energy consumption and additionally frequent residence in the dry dock.

Apart from fouling by algae, for example *Ectocarpus* sp. and *Ceramium* sp., fouling by sessile Entomostraka groups, which come under the generic term Cirripedia (cirriped crustaceans), is of particular importance.

Surprisingly, it has now been found that the compounds according to the invention, alone or in combination with other active compounds, have an outstanding antifouling action.

Using the compounds according to the invention, alone or in combination with other active compounds, allows the use of heavy metals such as, for example, in bis(trialkyltin) sulfides, tri-n-butyltin laurate, tri-n-butyltin chloride, copper(I) oxide, triethyltin chloride, tri-n-butyl(2-phenyl-4-chlorophenoxy)tin, tributyltin oxide, molybdenum disulphide, antimony oxide, polymeric butyl titanate, phenyl(bispyridine) bismuth chloride, tri-n-butyltin fluoride, manganese ethylenebisthiocarbamate, zinc dimethyldithiocarbamate, zinc ethylenebisthiocarbamate, zinc salts and copper salts of 2-pyridinethiol 1-oxide, bisdimethyldithiocarbamoylzinc ethylene-bisthiocarbamate, zinc oxide, copper(I) ethylene-bisdithiocarbamate, copper thiocyanate, copper naphthenate and tributyltin halides to be dispensed with, or the concentration of these compounds to be substantially reduced.

If appropriate, the ready-to-use antifouling paints can additionally comprise other active compounds, preferably algaecides, fungicides, herbicides, molluscicides, or other antifouling active compounds.

Preferably suitable components in combinations with the antifouling compositions according to the invention are:

algaecides such as 2-tert-butylamino-4-cyclopropylamino-6-methylthio-1,3, 5-triazine; dichlorophen, diuron, endothal, fentin acetate, isoproturon, methabenzthiazuron, oxyfluorfen, quinoclamine and terbutryn;

fungicides such as benzo[b]thiophenecarboxylic acid cyclohexylamide S,S-dioxide, dichlofluanid, fluorfolpet, 3-iodo-2-propinyl butyl-carbamate, tolylfluanid and azoles such as azaconazole, cyproconazole, epoxyconazole, hexaconazole, metconazole, propiconazole and tebuconazole;

molluscicides such as fentin acetate, metaldehyde, methiocarb, niclosamid, thiodicarb and trimethacarb, iron chelates;

or conventional antifouling active compounds such as 4,5-dichloro-2-octyl-4-isothiazolin-3-one, diiodomethylparatryl sulphone, 2-(N,N-dimethyl-thiocarbamoylthio)-5-nitrothiazyl, potassium, copper, sodium and zinc salts of 2-pyridinethiol 1-oxide, pyridine-triphenylborane, tetrabutyldistannoxane, 2,3,5,6-tetrachloro-4-(methylsulfonyl)-pyridine, 2,4,5,6-tetrachloroisophthalonitrile, tetramethylthiuram disulphide and 2,4,6-trichlorophenylmaleiimide.

The antifouling compositions used comprise the active compound according to the invention of the compositions according to the invention in a concentration of 0.001 to 50% by weight, in particular 0.01 to 20% by weight.

Moreover, the antifouling compositions according to the invention comprise the customary components such as, for example, those described in Ungerer, Chem. Ind. 1985, 37, 730-732 and Williams, Antifouling Marine Coatings, Noyes, Park Ridge, 1973.

Besides the algicidal, fungicidal, molluscicidal active compounds and insecticidal active compounds according to the invention, antifouling paints comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/acrylonitrile rubbers, drying oils such as linseed oil, resin esters or modified hardened resins in combination with tar or bitumens, asphalt and epoxy compounds, small amounts of chlorine rubber, chlorinated polypropylene and vinyl resins.

If appropriate, paints also comprise inorganic pigments, organic pigments or colorants which are preferably insoluble in salt water. Paints may furthermore comprise materials such as colophonium to allow controlled release of the active compounds. Furthermore, the paints may comprise plasticizers, modifiers which affect the rheological properties and other conventional constituents. The compounds according to the invention or the abovementioned mixtures may also be incorporated into self-polishing antifouling systems.

The active compounds according to the invention are also suitable for controlling animal pests, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all developmental stages. These pests include:

From the order of the Scorpionidea, for example, *Buthus occitanus*.

From the order of the Acarina, for example, *Argas persicus, Argas reflexus, Bryobia* spp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae*.

From the order of the Araneae, for example, *Aviculariidae, Araneidae*.

From the order of the Opiliones, for example, *Pseudoscorpiones chelifer, Pseudoscorpiones cheiridium, Opiliones phalangium*.

From the order of the Isopoda, for example, *Oniscus asellus, Porcellio scaber*.

From the order of the Diplopcda, for example, *Blaniulus guttulatus, Polydesmus* spp.

From the order of the Chilopoda, for example, *Geophilus* spp.

From the order of the Zygentoma, for example, *Ctenolepisma*, spp., *Lepisma saccharina, Lepismodes inquilinus*.

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fulliginosa, Supella longipalpa*.

From the order of the Saltatoria, for example, *Acheta domesticus*.

From the order of the Dermaptera, for example, *Forficula auricularia*.

From the order of the Isoptera, for example, *Kalotermes* spp., *Reticulitermes* spp.

From the order of the Psocoptera, for example, *Lepinatus* spp., *Liposcelis* spp.

From the order of the Coleptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum*.

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga camaria, Simulium* spp., *Stomoxys calcitrans, Tipula paludosa*.

From the order of the Lepidoptera, for example, *Achroia grisella, Galleria mellonella, Plodia interpunctella, Tinea cloacella, Tinea pellionella, Tineola bisselliella*.

From the order of the Siphonaptera, for example, *Ctenocephalides canis, Ctenocephalides felis, Pulex irritans, Tunga penetrans, Xenopsylla cheopis*.

From the order of the Hymenoptera, for example, *Camponotus herculeanus, Lasius fuliginosus, Lasius niger, Lasius umbratus, Monomorium pharaonis, Paravespula* spp., *Tetramorium caespitum*.

From the order of the Anoplura, for example, *Pediculus humanus capitis, Pediculus humanus corporis, Phthirus pubis*.

From the order of the Heteroptera, for example, *Cimex hemipterus, Cimex lectularius, Rhodinus prolixus, Triatoma infestans*.

In the field of household insecticides, they are used alone or in combination with other suitable active compounds, such as phosphoric acid esters, carbamates, pyrethroids, growth regulators or active compounds from other known classes of insecticides.

They are used as aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

The active compounds according to the invention can also be used as defoliants, desiccants, haulm killers and, in particular, as weed killers. Weeds in the broadest sense are understood as meaning all plants which grow at locations where they are undesired. Whether the substances according to the invention act as nonselective or selective herbicides depends essentially on the application rate.

The active compounds according to the invention can be used for example in the following plants:

Dicotyledonous weeds of the genera: *Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Ervsimum, Euphorbia, Galeopsis, Galinsoga, Galium, Hibis-* cus, *Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

Dicotyledonous crops of the genera: *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia.*

Monocotyledonous weeds of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Monocotyledonous crops of the genera: *Allium, Ananas, Asparagus, Avena, Hordeum, Oryza, Panicum, Saccharum, Secale, Sorghum, Triticale, Triticum, Zea.*

However, the use of the active compounds according to the invention is in no way restricted to these genera, but extends in the same manner to other plants.

Depending on the concentration, the active compounds according to the invention are suitable for the nonselective weed control on, for example, industrial terrains and railway tracks and on paths and locations with and without trees. Likewise the active compounds according to the invention can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantings and hop fields, on lawns, turf and pastureland, and for the selective control of weeds in annual crops.

The compounds of the formula (I) according to the invention have strong herbicidal activity and a broad activity spectrum when used on the soil and on aerial plant parts. To a certain extent, they are also suitable for the selective control of monocotyledonous and dicotyledonous weeds in monocotyledonous and dicotyledonous crops, both pre- and postemergence.

At certain concentrations or application rates, the active compounds according to the invention can also be employed for controlling animal pests and fungal or bacterial plant diseases. If appropriate, they can also be used as intermediates or precursors for the synthesis of other active compounds.

The active compounds can be converted into the customary formulations, such as solutions, emulsions, wettable powders, suspensions, powders, dusts, pastes, soluble powders, granules, suspoemulsion concentrates, natural and synthetic materials impregnated with active compound, and microencapsulations in polymeric materials.

These formulations are produced in a known manner, for example by mixing the active compounds with extenders, that is, liquid solvents and/or solid carriers, optionally with the use of surfactants, that is, emulsifiers and/or dispersants and/or foam formers.

If the extender used is water, it is also possible, for example, to use organic solvents as cosolvents. The following are essentially suitable as liquid solvents: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulfoxide, or else water.

Suitable solid carriers are: for example ammonium salts and ground natural minerals such as kaolinsi clays, talc, chalk, quartz, attapulgite, montmorillonite or diatomaceous earth, and ground synthetic minerals such as highly disperse silica, alumina and silicates, suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, corn cobs and tobacco stalks; suitable emulsifiers and/or foam-formers are: for example nonionic and anionic emulsifiers such as polyoxyethylene fatty acid esters, polyoxyethylene fatty alcohol ethers, for example alkylaryl polyglycol ethers, alkylsulfonates, alkyl sulfates, arylsulfonates or else protein hydrolyzates; suitable dispersants are: for example lignosulfite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids, can be used in the formulations. Other possible additives are mineral and vegetable oils.

It is possible to use colorants such as inorganic pigments, for example iron oxide, titanium oxide and Prussian Blue, and organic colorants, such as alizarin colorants, azo colorants and metal phthalocyanine colorants, and trace nutrients such as salts of iron, manganese, boron, copper, cobalt, molybdenum and zinc.

The formulations generally comprise between 0.1 and 95 percent by weight of active compound, preferably between 0.5 and 90%.

The active compounds according to the invention, as such or in their formulations, can also be used for weed control purposes as a mixture with known herbicides and/or with substances which improve crop plant compatibility ("safeners"), ready mixes or tank mixes being possible. Mixtures with herbicide products which contain one or more known herbicides and a safener are hence also possible.

Herbicides which are suitable for the mixtures are known herbicides, for example acetochlor, acifluorfen (-sodium), aclonifen, alachlor, alloxydim (-sodium), ametryne, amicarbazone, amidochlor, amidosulfuron, anilofos, asulam, atrazine, azafenidin, azimsulfuron, beflubutamid, benazolin (-ethyl), benfuresate, bensulfuron (-methyl), bentazone, benzfendizone, benzobicyclon, benzofenap, benzoylprop (-ethyl), bialaphos, bifenox, bispyribac (-sodium), bromobutide, bromofenoxim, bromoxynil, butachlor, butafenacil (-allyl), butroxydim, butylate, cafenstrole, caloxydim, carbetamide, carfentrazone (-ethyl), chlomethoxyfen, chloramben, chloridazon, chlorimuron (-ethyl), chlornitrofen, chlorsulfuron, chlortoluron, cinidon (-ethyl), cinmethylin, cinosulfuron, clefoxydim, clethodim, clodinafop (-propargyl), clomazone, clomeprop, clopyralid, clopyrasulfuron (-methyl), cloransulam (-methyl), cumyluron, cyanazine, cybutryne, cycloate, cyclosulfamuron, cycloxydim, cyhalofop (-butyl), 2,4-D, 2,4-DB, desmedipham, diallate, dicamba, dichlorprop (-P), diclofop (-methyl), diclosulam, diethatyl (-ethyl), difenzoquat, diflufenican, diflufenzopyr, dimefuron, dimepiperate, dimethachlor, dimetharnetryn, dimethenamid, dimexyflam, dinitramine, diphenamid, diquat, dithiopyr, diuron, dymron, epropodan, EPTC, esprocarb, ethalfluralin, ethametsulfuron (-methyl), ethofumesate, ethoxyfen, ethoxysulfuron, etobenzanid, fenoxaprop (-P-ethyl), fentrazamide, flamprop (-isopropyl, -isopropyl-L, -methyl), flazasulfuron, florasulam, fluazifop (-P-butyl), fluazolate, flucarbazone (-sodium), flufenacet, flumetsulam, flumiclorac (-pentyl), flumioxazin, flumipropyn, flumetsulam, fluometuron, fluorochloridone, fluoroglycofen (-ethyl), flupoxam, flupropacil, flurpyrsulfuron (-methyl, -sodium), flurenol (-butyl), fluridone, fluroxypyr (-butoxypropyl, -meptyl), flurprimidol, flurtamone, fluthiacet (-methyl), fluthiamide, fomesafen, foramsulfuron, glufosinate (-ammonium), glyphosate (-isopropylammonium); halosafen, haloxyfop (-ethoxyethyl, -P-methyl), hexazinone, imazamethabenz (-methyl), imazamethapyr, imazamox, imazapic, imazapyr, imazaquin, imazethapyr, imazosulfuron, iodosulfuron (-methyl, -sodium), ioxynil, isopropalin, isoproturon, isouron, isoxaben, isoxachlortole, isoxaflutole, isoxapyrifop, lactofen, lenacil, linuron, MCPA, mecoprop, mefenacet, mesotrione, metamitron, metazachlor, methabenzthiazuron, metobenzuron, metobromuron, (alpha-) metolachlor, metosulam, metoxuron, metribuzin, metsulfuron (-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pendralin, pentoxazone, phenmedipham, picolinafen, piperophos, pretilachlor, primisulfuron (-methyl), profluazol, prometryn, propachlor, propanil, propaquizafop, propisochlor, propoxycarbazone (-sodium), propyzamide, prosulfocarb, prosulfuron, pyraflufen (-ethyl), pyrazogyl, pyrazolate, pyrazosulfuron (-ethyl), pyrazoxyfen, pyribenzoxim, pyributicarb, pyridate, pyridatol, pyriftalide, pyriminobac (-methyl), pyrithiobac (-sodium), quinchlorac, quinmerac, quinoclamine, quizalofop (-P-ethyl, -P-tefuryl), rimsulfuron, sethoxydim, simazine, simetryn, sulcotrione, sulfentrazone, sulfometuron (-methyl), sulfosate, sulfosulfuron, tebutam, tebuthiuron, tepraloxydim, terbuthylazine, terbutryn, thenylchlor, thiafluamide, thiazopyr, thidiazimin, thifensulfuron (-methyl), thiobencarb, tiocarbazil, tralkoxydim, triallate, triasulfuron, tribenuron (-methyl), triclopyr, tridiphane, trifluralin, trifloxysulfuron, triflusulfuron (-methyl), tritosulfuron.

Furthermore suitable for the mixtures are known safeners, for example:

AD-67, BAS-145138, benoxacor, cloquintocet (-mexyl), cyometrinil, 2,4-D, DKA-24, dichliormid, dymron, fenclorim, fenchloroazole (-ethyl), flurazole, fluxofenim, furilazole, isoxadifen (-ethyl), MCPA, mecoprop (-P), mefenpyr (-diethyl), MG-191, oxabetrinil, PPG-1292, R-29148.

A mixture with other known active compounds, such as fungicides, insecticides, acaricides, nematicides, bird repellents, plant nutrients and soil conditioners, is also possible.

The active compounds can be applied as such, in the form of their formulations or the use forms prepared therefrom by further dilution, such as ready-to-use solutions, suspensions, emulsions, powders, pastes and granules. They are applied in the customary manner, for example by watering, spraying, atomizing, scattering.

The active compounds according to the invention can be applied both before and after plant emergence. They can also be incorporated into the soil prior to sowing.

The application rate of active compound can vary within a substantial range. Essentially, it depends on the nature of the desired effect. In general, the application rates are between 1 g and 10 kg of active compound per hectare of soil area, preferably between 5 g and 5 kg per ha.

Preparation and use of the active compounds according to the invention are illustrated in the examples below.

PREPARATION EXAMPLES

Example I-1-a-1

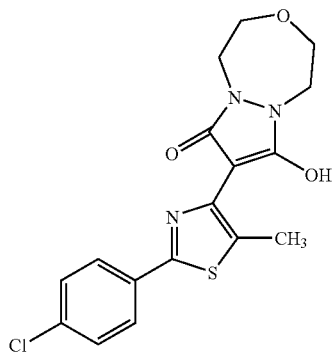

1.3 g (0.003 mol) of the compound of Example V-1-1 are initially charged in 54 ml of N,N-dimethylacetamide, 0.723 g (0.006 mol) of potassium tert-butoxide is added and the mixture is stirred at room temperature for 1 hour. Ice-water is then added, and the pH is adjusted to pH=1 using concentrated hydrochloric acid. Since there is no precipitation, the reaction solution is extracted with toluene and the solvent is removed using a rotary evaporator.

Crystallization is carried out using heptane.

Yield: 0.38 g (33% of theory), m.p. 233° C.

Example I-1-b-1

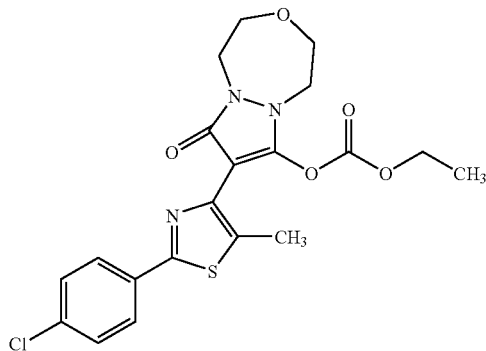

0.2 g of the compound of Example I-1-a-1 and 0.063 g of ethyl chloroformate are initially charged in 10 ml of tetrahydrofuran and stirred for 15 min, then 1 mg of N,N-dimethylaminopyridine and 0.04 ml of triethylamine are added. The mixture is stirred at room temperature for 1 hour, and 50 ml of water are then added. The mixture is extracted with dichloromethane, the extract is dried and the solvent is removed using a rotary evaporator. A little ethyl acetate is added and the product is precipitated using n-heptane. The precipitate is filtered off with suction and washed with water. The produce is dried in a drying cabinet.

Yield: 0.086 g (36% of theory), m.p. 167° C.

Example I-3-a-1

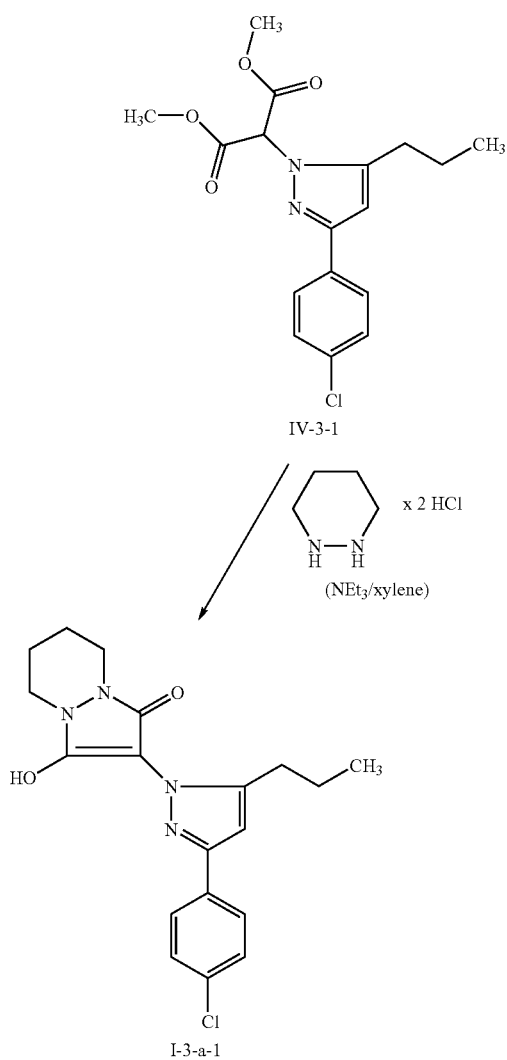

1. Example (IV-3-1)

108 mg (4.2 mmol) of sodium hydride are initially charged in dry toluene and heated at 100° C., 784 mg (2.7 mmol) of the compound of Example XXIV-A-3 (DE-A-10 152 005) are taken up in 724 mg (8 mmol) of dimethyl carbonate and added to the initial charge. The mixture is then heated under reflux for 1.5 h and cooled to 0° C., methanol is slowly added dropwise and the mixture is concentrated under reduced pressure. The residue obtained from the rotary evaporator is taken up in 10% strength ammonium chloride solution and extracted with toluene. The toluene phase is dried, concentrated and chromatographed on 300 ml of silica gel KG 60 using cyclohexane/ethyl acetate 10:1.

Yield: 620 mg (64%, 98% pure by HPLC)

2. Example (I-3-a-1)

The compound of Preparation Example (IV-3-1) (50 mg, 0.14 mmol), hexahydropyrazine ×2 HCL (23 mg 0.14 mmol) and triethylamine (29 mg, 0.29 mmol) are stirred in 25 ml of xylene overnight, with exclusion of atmospheric humidity and under reflux. The mixture is concentrated under reduced pressure, taken up in methylene chloride and extracted with dilute HCl, the organic phase is dried and concentrated under reduced pressure: 45 mg. The residue was then separated on a chromatotron using the mobile phase cyclohexane/ethyl acetate=10:1 to 1:1.

Yield: 18 mg (34%), m.p.: 83-86° C.

Example I-3-a-2

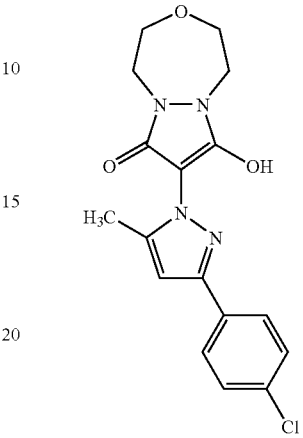

3.2 g (0.008 mol) of the compound of Example V-3-1 are initially charged in 40 ml of N,N-dimethylacetamide, 1.85 g of potassium tert-butoxide are added and the mixture is stirred at 50° C. for 1 hour. After cooling, 80 g of ice are added. Using concentrated hydrochloric acid, the pH is adjusted to pH-1. The precipitate is filtered off with suction, washed with water and suspended in n-heptane. It is then dried.

Yield: 2 g (71% of theory), m.p. 224° C.

The following compounds of the formula (I-3-a) are obtained analogously to Examples (I-3-a-1) and (I-3-a-2) and in accordance with the general statements on the preparation

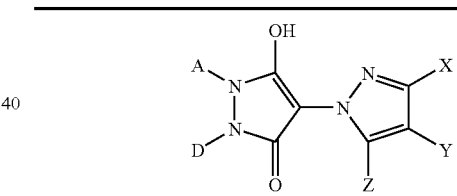

| Ex. No. | A | D | X | Y | Z | m.p. ° C. |
|---|---|---|---|---|---|---|
| I-3-a-3 | | —(CH$_2$)$_4$— | 4-ClC$_6$H$_4$ | H | CH$_3$ | 199 |

Example I-3-b-1

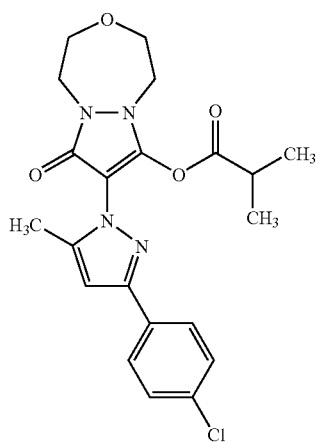

0.2 g of the compound of Example I-3-a-2 and 0.06 ml of 2-methylpropionyl chloride in 10 ml of tetrahydrofuran are stirred for 15 minutes. 1 mg of N,N-dimethylaminopyridine and 0.04 ml of triethylamine are added, and the mixture is stirred at room temperature for 1 hour. 50 ml of water are added, and the mixture is extracted with dichloromethane. The extract is dried and the solvent is removed using a rotary evaporator. A little ethyl acetate is added to the reaction solution, and the product is precipitated using n-heptane. The precipitate is filtered off with suction, washed with water and dried in a drying cabinet.

Yield: 0.2 g (94% of theory), m.p. 166° C.

The following compounds of the formula (I-3-b) are obtained analogously to Example (I-3-b-1) and in accordance with the general statements on the preparation

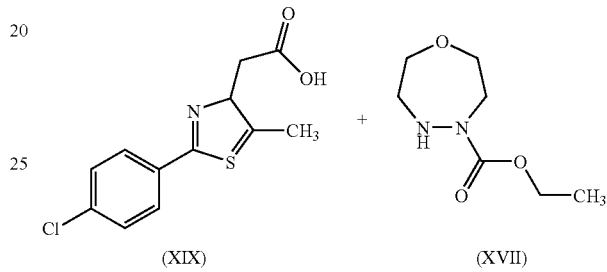

| Ex. No. | A | D | X | Y | Z | $R^1$ | m.p. ° C. |
|---|---|---|---|---|---|---|---|
| I-3-b-2 | —$(CH_2)_4$— | | 4-$ClC_6H_4$ | H | $CH_3$ | $t-C_4H_9$ | 86 |
| I-3-b-3 | —$(CH_2)_2$-O-$(CH_2)_2$— | | 4-$ClC_6H_4$ | H | $CH_3$ | $t-C_4H_9$ | 182 |

Example I-3-c-1

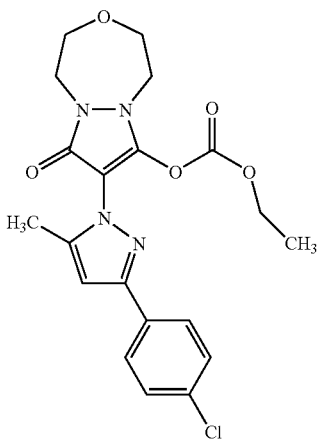

0.2 g of the compound of Example (I-3-a-2) and 0.06 ml of ethyl chloroformate are initially charged in 10 ml of tetrahydrofuran and stirred for 15 minutes. 1 mg of N,N-dimethylaminopyridine and 0.04 ml of triethylamine are added. The mixture is stirred at room temperature for 1 hour, 50 ml of water are added and the mixture is extracted with dichloromethane. The extract is dried and the solvent is removed using a rotary evaporator. A little ethyl acetate is added and the product is precipitated using n-heptane. The precipitate is filtered off with suction and washed with water. It is dried in a drying cabinet.

Yield: 0.19 g (79% of theory), m.p. 128° C.

Example V-1-1

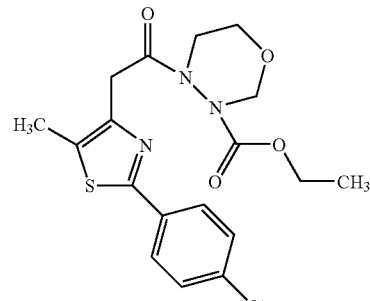

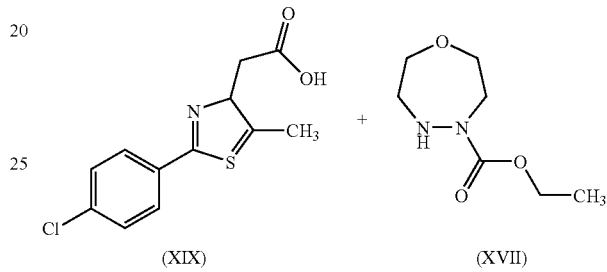

(XIX)  (XVII)

1.1 g (0.006 mol) of ethyl oxdiazepincarbamate are initially charged in 40 ml of tetrahydrofuran, 3.6 ml of triethylamine and 1.7 g (0.006 mol) of 2-(4-chlorophenyl)-5-methylthiazolylacetic acid are added and the mixture is stirred for 10 minutes. 0.6 ml of phosphoryl chloride are added dropwise and the mixture is stirred under reflux, the reaction being monitored by thin-layer chromatography. The mixture is concentrated using a rotary evaporator and the residue is taken up in ethyl acetate, washed with water, dried and concentrated using a rotary evaporator.

Yield: 1.4 g (52% of theory), oil

Without further purification, the oil was used for the synthesis of Example I-1-a-1.

$^1$H-NMR data (CDCl$_3$, 300 MHz): δ=7.8 (d, 2H, Ar—H), 7.35 (d, 2H, Ar—H), 2.4 (s, 3H, CH$_3$-thiazolyl), 1.3 (tr, 3H, CH$_3$—CH$_2$—O) ppm.

The following compounds of the formula (V-3) are obtained analogously to Example (V-1-1) and in accordance with the general statements on the preparation of compounds of the formula (V)

(V-3)

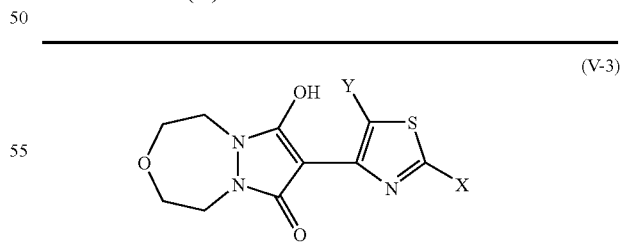

| Ex. No. | A | D | X | Y | Z | $R^8$ | m.p. ° C. |
|---|---|---|---|---|---|---|---|
| V-3-1 | —$(CH_2)_2$—O—$(CH_2)_2$— | | 4-$ClC_6H_4$ | H | $CH_3$ | $C_2H_5$ | 120 |
| V-3-2 | —$(CH_2)_4$— | | 4-$ClC_6H_4$ | H | $CH_3$ | $C_2H_5$ | *Oil |

*$^1$H-NMR (300 MHz, CDCl$_3$): δ = 1.3 (t, 3H, O-CH$_2$CH$_3$), 2.25 (s, 3H, pyrazolyl-CH$_3$), 4.8, 5.1 (2d, 2H, N-CH$_2$-CO), 6.35 (s, 1H, pyrazolyl-H) ppm.

USE EXAMPLES

Example A

Critical concentration test/soil insects—treatment of transgenic plants

Test insect: *Diabrotica balteata*—larvae in soil
Solvent: 7 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is poured onto the solvent. Here, the concentration of active compound in the preparation is virtually immaterial, only the amount of weight of active compound per volume unit of soil, which is stated in ppm (mg/l), matters. The soil is filled into 0.25 l pots, and these are allowed to stand at 20° C.

Immediately after the preparation, 5 pregerminated maize corns of the cultivar YIELD GUARD (trade mark of Monsanto Comp., USA) are placed into each pot. After 2 days, the appropriate test insects are placed into the treated soil. After a further 7 days, the efficacy of the active compound is determined by counting the maize plants that have emerged (1 plant 20% activity).

Example B

*Heliothis virescens* test—treatment of transgenic plants
Solvent: 7 parts by weight of acetone
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Soybean shoots (*Glycine max*) of the cultivar Roundup Ready (trade mark of Monsanto Comp. USA) are treated by being dipped into the preparation of active compound of the desired concentration and are populated with the tobacco butt worm *Heliothis virescens* while the leaves are still moist.

After the desired period of time, the kill of the insects is determined.

Example C

1. Herbicidal Pre-emergence Action

Seeds of monocotyledonous and dicotyledonous weed and crop plants are placed into sandy loam and covered with soil. The test compounds, formulated in the form of emulsion concentrates (EC), are, in various dosages with a water application rate of 800 l/ha (converted), with wetting agent added, applied to the surface of the covering soil.

After the treatment, the pots are placed in a greenhouse and kept under good growth conditions for the test plants. The visual assessment of the emergence damage on the test plants is carried out after a trial period of 2 to 3 weeks by comparison with untreated controls (herbicidal effect in percent (%): 100% effect=the plants have died, 0% effect=like control plants).

2. Herbicidal Post-emergence Action

Seeds of monocotyledonous and dicotyledonous weed and crop plants are placed into sandy loam, covered with soil and cultivated in a greenhouse under good growth conditions. About 2 weeks after sowing, the test plants are treated at the one-leaf stage. The test compounds, formulated as emulsion concentrates (EC), are, in various dosages with a water application rate of 800 l/ha (converted), with wetting agents added, sprayed onto the green parts of the plants. After the test plants have, been kept in the greenhouse under optimum growth conditions for 2 weeks, the effect of the preparations is rated visually in comparison to untreated controls (herbicidal effect in percent (%): 100% effect=the plants have died, 0% effect=like control plants).

| Pre-emergence greenhouse | g a.i./ha | Lolium | Setaria |
|---|---|---|---|
| Ex. I-3-a-1 | 1000 | 100 | 100 |

| Post-emergence greenhouse | g a.i./ha | Echinoclora | Lolium | Setaria |
|---|---|---|---|---|
| Ex. I-3-a-1 | 1000 | 100 | 90 | 100 |

Example D

Myzus Test—(Spray Treatment)

Solvents: 78 parts by weight of acetone 1.5 parts by weight of dimethylformamide Emulsifier: 0.5 part by weight of alkylaryl polyglycol ether To produce a suitable preparation of active compound, 1 part by weight of active compound is mixed with the stated amount of solvents and the stated amount of emulsifier, and the concentrate is diluted with emulsifier-containing water to the desired concentration.

Discs of Chinese cabbage (*Brassica pekinensis*) which are infested by all stages of the green peach aphid (*Myzus persicae*) are sprayed with a preparation of active compound of the desired concentration.

After the desired period of time, the effect in % is determined. 100% means that all aphids have been killed; 0% means that none of the aphids have been killed.

In this test, for example, the following compounds of the preparation examples show good efficacy:

TABLE D

| | Plant-damaging insects Myzus test (spray treatment) | |
|---|---|---|
| Active compounds | Concentration of active compounds in g/ha | Kill rate in % after 5 d |
| Example I-3-a-1 | 100 | 100 |

The invention claimed is:

1. A compound of formula (I)

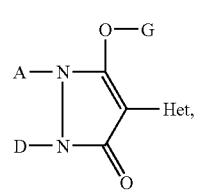

in which

Het represents

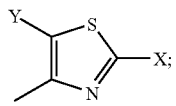 (I-1)

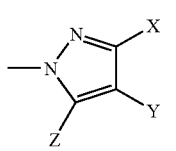 (I-3)

or

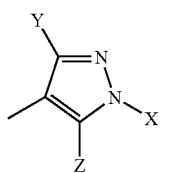 (I-4)

X represents $C_1$-$C_6$-alkyl, $C_1$-$C_4$-haloalkyl, optionally halogen-, $C_1$-$C_6$-alkyl-, $C_1$-$C_6$-alkoxy-, $C_1$-$C_4$-haloalkyl-, $C_1$-$C_4$-haloalkoxy-, or nitro- or cyano-substituted phenyl;

Y represents hydrogen, $C_1$-$C_6$-alkyl, chlorine or bromine;

Z represents $C_1$-$C_4$-alkyl;

A represents $C_1$-$C_4$-alkyl;

D represents $C_1$-$C_4$-alkyl; or

A and D together represent $C_3$-$C_5$-alkanediyl in which optionally one methylene group is replaced by oxygen G represents hydrogen (a) or

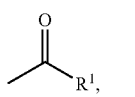 (b)

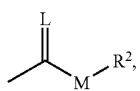 (c)

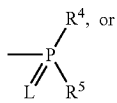 (e)

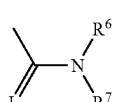 (g)

in which

L represents oxygen or sulfur;

M represents oxygen;

$R^1$ represents $C_1$-$C_4$-alkyl;

$R^2$ represents $C_1$-$C_4$-alkyl;

$R^4$ and $R^5$ independently of one another represent $C_1$-$C_4$-alkoxy;

$R^6$ and $R^7$ independently of one another represent hydrogen; $C_1$-$C_4$-alkyl.

2. The compound of the formula (I) as claimed in claim 1 in which

Het represents

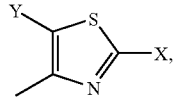 (I-1)

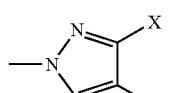 (I-3)

or

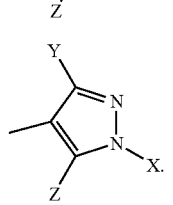 (I-4)

X represents $C_1$-$C_4$-alkyl, $C_1$-$C_2$-haloalkyl; phenyl which is optionally mono- to trisubstituted by fluorine, chlorine, bromine, $C_1$-$C_4$-alkyl, $C_1$-$C_4$-alkoxy, $C_1$-$C_2$-haloalkyl, $C_1$-$C_2$-haloalkoxy, nitro or cyano, Y represents hydrogen, $C_1$-$C_4$-alkyl or, chlorine or bromine;

Z represents $C_1$-$C_4$-alkyl,

A represents $C_1$-$C_4$-alkyl;

D represents $C_1$-$C_4$-alkyl; or

A and D together represent $C_3$-$C_5$-alkenediyl in which optionally one methylene group may be replaced by oxygen G represents hydrogen (a) or

 (b)

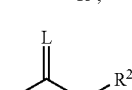 (c)

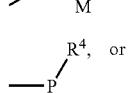 (e)

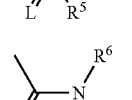 (g)

in which

L represents oxygen or sulfur;

M represents oxygen;

$R^1$ represents $C_1$-$C_4$-alkyl;

$R^2$ represents $C_1$-$C_4$-alkyl;

$R^4$ represents $C_1$-$C_4$-alkoxy;

$R^5$ represents $C_1$-$C_4$-alkoxy;

$R^6$ represents $C_1$-$C_4$-alkyl;

$R^7$ represents hydrogen, $C_1$-$C_4$-alkyl.

3. The compound of the formula (I) as claimed in claim 1 in which

Het represents

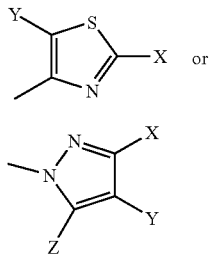

X represents methyl, ethyl, propyl, trifluoromethyl; phenyl which is optionally mono- or disubstituted by fluorine, chlorine, bromine, methyl, ethyl, trifluoromethyl, isopropyl, tert-butyl, trifluoromethoxy, methoxy, ethoxy, isopropoxy, tert-butoxy, cyano or nitro;

Y represents hydrogen in the case of Het (I-3); or methyl, ethyl, propyl, chlorine or bromine in the case of Het (I-1);

Z represents methyl, ethyl, propyl, isopropyl;

A represents methyl or ethyl;

D represents methyl, ethyl, allyl;

or

A and D together represent optionally substituted $C_3$-$C_5$-alkanediyl in which optionally one carbon atom is replaced by oxygen;

G represents hydrogen (a) or

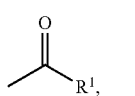
(b),

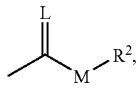
(c),

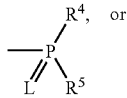
(e),

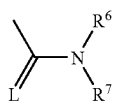
(g)

in which

L represents oxygen or sulfur;

M represents oxygen;

$R^1$ represents $C_1$-$C_4$-alkyl;

$R^2$ represents $C_1$-$C_4$-alkyl;

$R^4$ represents $C_1$-$C_4$-alkoxy;

$R^5$ represents methoxy, ethoxy;

$R^6$ represents $C_1$-$C_4$-alkyl;

$R^7$ represents hydrogen, methyl, ethyl, propyl.

4. The compound of the formula (I) as claimed in claim 1 in which

Het represents

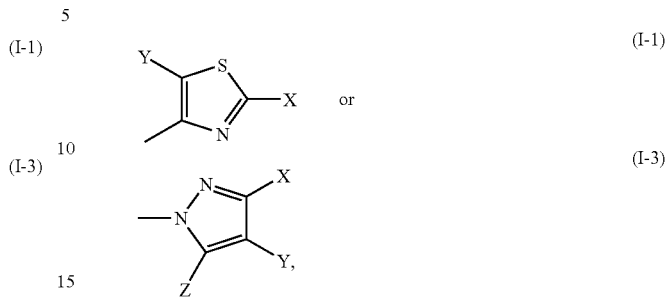

X represents phenyl which is optionally mono- or disubstituted by fluorine, chlorine, bromine, methyl, trifluoromethyl, methoxy or trifluoromethoxy;

Y represents hydrogen in the case of Het (I-3) or methyl, ethyl or propyl in the case of Het (I-1);

Z represents methyl, ethyl, propyl or isopropyl;

A represents methyl or ethyl;

D represents methyl or ethyl;

A and D represent $C_3$-$C_5$-alkanediyl in which optionally one carbon atom is replaced by an oxygen atom;

G represents hydrogen (a) or represents

(b)

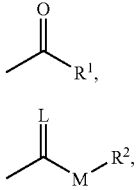
(C)

in which

L represents oxygen;

M represents oxygen;

$R^1$ represents $C_1$-$C_4$-alkyl; and $R^2$ represents $C_1$-$C_4$-alkyl.

5. The compound of the formula (I) as claimed in claim 1 in which

Het represents

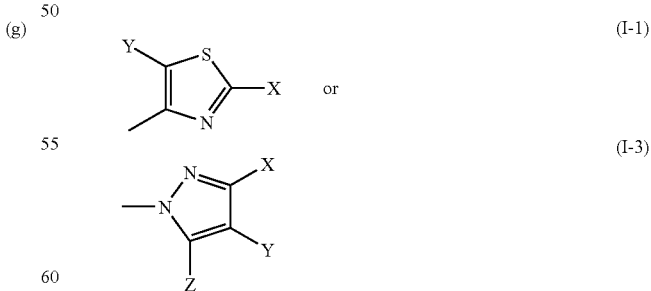

X represents phenyl which is optionally monosubstituted by chlorine;

Y represents hydrogen in the case of Het (I-3); or methyl or propyl in the case of Het (I-1);

Z represents methyl or propyl;

A and D represent $C_3$-$C_5$-alkanediyl in which optionally one carbon atom is replaced by an oxygen atom;
G represents hydrogen (a) or one of the groups

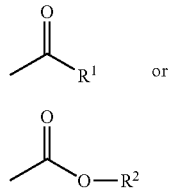 (b) or

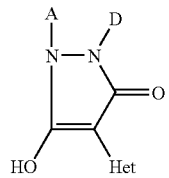 (c)

$R^1$ represents $C_1$-$C_4$-alkyl; and
$R^2$ represents $C_1$-$C_4$-alkyl.

6. A process for preparing compounds of the formula (I) as claimed in claim 1, comprising
A) obtaining a compound of the formula

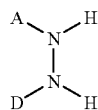

in which
A, D and Het are as defined in claim 2, by contacting a compound of the formula (II)

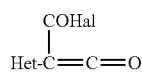 (II)

in which
A and D are as defined above
a) with a compound of the formula (III)

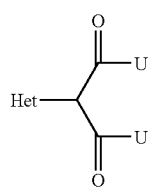 (III)

in which
Het is as defined above, optionally in the presence of a diluent and optionally in the presence of an acid acceptor, or
b) with a compound of the formula (IV)

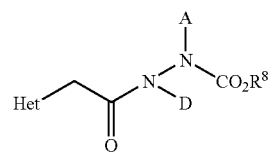 (IV)

in which
Het is as defined above and U represents O—$R^8$, where $R^8$=$C_{1\text{-}1\text{-}C4}$-alkyl, optionally in the presence of a diluent and optionally in the presence of a base, or
c) with a compound of the formula (V)

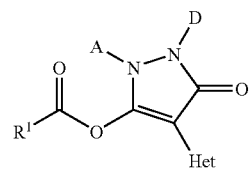 (V)

in which
A, D, Het and $R^8$ are as defined above, optionally in the presence of a diluent and optionally in the presence of a base, (B) obtaining a compound of the formula

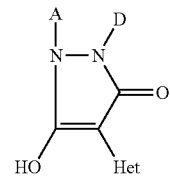

in which A, D, $R^1$ and Het are as defined above,
by contacting a compound of the formula

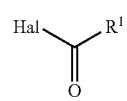

in which A, D and Het are as defined above
(a) with an acid halide of the formula (VI)

 (VI)

in which
$R^1$ is represents $C_1$-$C_4$-alkyl and
Hal represents halogen
or
(b) with a carboxylic anhydride of the formula (VII)

$R^1$—CO—O—CO—$R^1$ (VII)

in which
$R^1$ is as defined above, optionally in the presence of a diluent and optionally in the presence of an acid binder;

(C) obtaining a compound of the formula

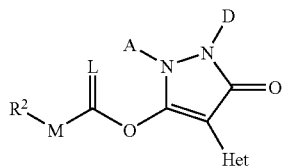

in which A, D, and Het are as defined above,
L represents oxygen,
M represents oxygen, and
$R^2$ represents $C_1$-$C_4$-alkyl,
by contacting a compound of the formula

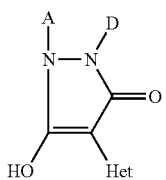

in which A, D and Het are as defined above with a chloroformic ester or chloroformic thioester of the formula (VIII)

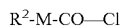 (VIII)

in which
$R^2$ and M are as defined above, optionally in the presence of a diluent and optionally in the presence of an acid binder;

(D) obtaining a compound of the formula

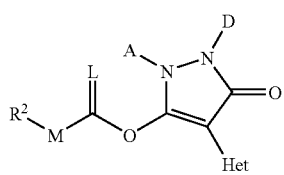

in which A, D, $R^2$, M and Het are as defined above and L represents sulfur,
by contacting a compound of the formula

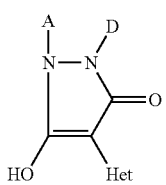

in which A, D and Het are as defined above with A chloromonothioformic ester or A chlorodithioformic ester of the formula (IX)

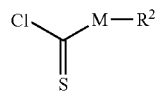 (IX)

in which
M and $R^2$ are as defined above, optionally in the presence of a diluent and optionally in the presence of an acid binder, (F) obtaining a compound of the formula

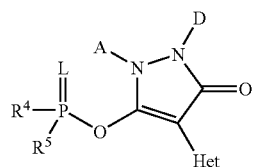

in which A, D, L, and Het are as defined above,
$R^4$, $R^5$ are as defined in claim 2, by contacting a compound of the formula

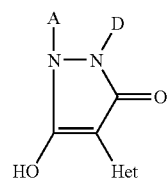

in which A, D and Het are as defined above with a phosphorus compound of the formula (XI)

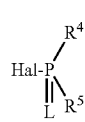 (XI)

in which
L, $R^4$ and $R^5$ are as defined above and
Hal represents halogen, optionally in the presence of a diluent and optionally in the presence of an acid binder, (H) obtaining a compound of the formula

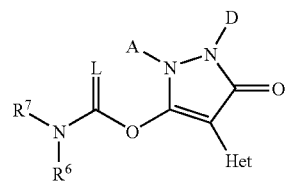

in which A, D, L, and Het are as defined above,
$R^6$, $R^7$ are as defined in claim 2, by contacting a compound of the formula

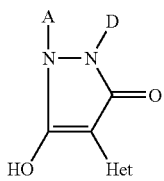

in which A, D and Het are as defined above (a) with an isocyanate or an isothiocyanate of the formula (XIV)

 (XIV)

in which

R⁶ and L are as defined above, optionally in the presence of a diluent and optionally in the presence of a catalyst, or (b) with a carbamide chloride or a thiocarbamide chloride of the formula (XV)

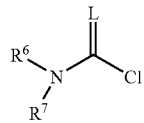 (XV)

in which

L, R⁶ and R⁷ are as defined above, optionally in the presence of a diluent and optionally in the presence of an acid binder.

7. A pesticide or herbicide or both, comprising at least one compound of the formula (I) as claimed in claim 1.

8. A method for controlling animal pests and/or unwanted vegetation, comprising: allowing compounds of the formula (I) as claimed in claim 1 to act on the vegetation, the pests and/or their habitat.

9. A process for preparing pesticides or herbicides, comprising: mixing compounds of the formula (I) as claimed in claim 1 with extenders or surfactants.

10. A composition, comprising an effective amount of an active compound combination comprising, as components
 (a') at least one compound of the formula (I) in which A, D, G and Het are as defined in claim 1, and
 (b') at least one crop plant compatibility-improving compound.

11. A method for controlling unwanted vegetation, comprising: allowing a composition as claimed in claim 10 to act on the vegetation or the vegetation's habitat.

12. A method for controlling unwanted vegetation, comprising allowing the composition of claim 10 to act on the vegetation or the vegetation's habitat separately, one soon after the other, or together.

* * * * *